United States Patent [19]
Martin et al.

[11] Patent Number: 6,054,478
[45] Date of Patent: *Apr. 25, 2000

[54] ANTIFUNGAL SORDARIDIN DERIVATIVES

[75] Inventors: Jose J. Martin; Jesus Chicharro Gonzalo; Jose R. R. Gomez; Silvestre Garcia-Ochoa Dorado; Federico Gomez De Las Heras, all of Madrid, Spain; Michael V. Hayes; Michael J. Dawson, both of Stevenage, United Kingdom; Howard G. Wildman, Richmond, Australia; Richard M. Hall, Stevenage, United Kingdom

[73] Assignee: Glaxo Wellcome S.A., Madrid, Spain

[*] Notice: This patent issued on a continued prosecution application filed under 37 CFR 1.53(d), and is subject to the twenty year patent term provisions of 35 U.S.C. 154(a)(2).

[21] Appl. No.: 08/836,284
[22] PCT Filed: Nov. 6, 1995
[86] PCT No.: PCT/EP95/04332
  § 371 Date: Jul. 16, 1997
  § 102(e) Date: Jul. 16, 1997
[87] PCT Pub. No.: WO96/14327
  PCT Pub. Date: May 17, 1996

[30] Foreign Application Priority Data

Nov. 8, 1994 [EP] European Pat. Off. ............. 94500174

[51] Int. Cl.$^7$ .................... A61K 31/35; C07D 315/00
[52] U.S. Cl. ................... 514/460; 549/416; 549/417; 549/418
[58] Field of Search ................... 549/416, 418, 549/417; 514/460

[56] References Cited

PUBLICATIONS

Alarcon, B. et al 'Screening for New Compounds with Antiherpes Activity'. CA 102:39536, 1984.
Hauser, D et al 'Sordarin 1. Isolation and Degradation of Sordarin' CA 75:49503, 1971.

*Primary Examiner*—Amelia Owens
*Attorney, Agent, or Firm*—Nixon & Vanderhye P.C.

[57] ABSTRACT

Compounds of the formula (I)

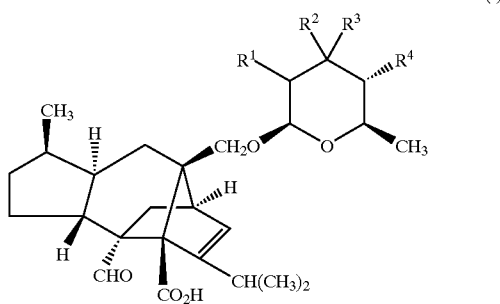

and pharmaceutically acceptable salts or metabolically labile derivatives thereof, processes for their preparation, their use as antifungal agents and intermediates for use in their preparation.

10 Claims, No Drawings

ANTIFUNGAL SORDARIDIN DERIVATIVES

This invention relates to novel sordarin derivatives having antifungal activity, to processes for their preparation, to pharmaceutical compositions containing them and to their use in medicine, more particularly in the prevention or treatment of diseases in animals, including humans, caused by fungal infection.

British Patent Specification No. 1,162,027 describes the preparation of an antibiotic, SL2266, by the cultivation of the strain NRRL 3196 of the fungus species *Sordaria araneosa*. SL 2266, later named sordarin, is reported to have fungistatic activity. The same research group also described in Helvetica Chimica Acta (1971), 51, 119–120 the degradation of sordarin to sordaricin. Published Japanese Patent Application No. J6 2040292A describes the preparation of an antibiotic, zofimarin, which is reported to have antifungal activity.

Sordarin, sordaricin and zofimarin may be represented by formula (A) below

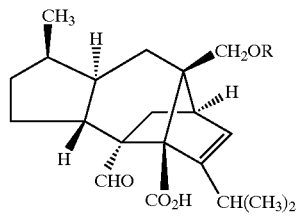

where OR as

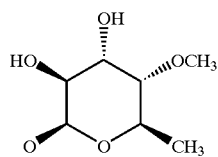

describes sordarin;

OR as OH describes sordaricin; and
OR as

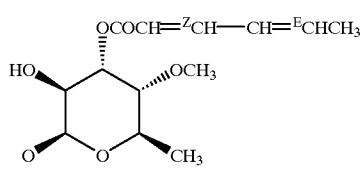

describes zofimarin.

Although sordarin and zofimarin exhibit antifungal activity, both compounds are only moderately active and have limited spectra of action when tested against a battery of fungal organisms. We now describe hereinafter a novel group of fungicidal sordarin derivatives which exhibit excellent antifungal activity and a broad spectrum of action. Thus, according to a first aspect of the present invention, we provide compounds of formula (I)

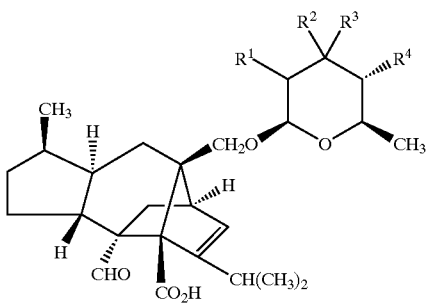

and pharmaceutically acceptable salts and solvates (e.g. hydrates) or metabolically labile derivatives thereof,
wherein $R^1$ represents hydrogen, halogen, hydroxyl or $C_{1-4}$alkoxy;
$R^2$ represents hydrogen, halogen, hydroxyl, $C_{1-10}$alkoxy, $C_{1-10}$alkylthio, $C_{1-6}$alkoxy$C_{1-4}$alkoxy, aryl$C_{1-6}$alkyloxy, aryl$C_{3-6}$alkenyloxy, azido, $NR^5COR^5$ (where each $R^5$ is independently hydrogen or $C_{1-6}$alkyl), $OR^6$ (where $R^6$ is a cyclic ether containing 4 to 8 atoms linked to the oxygen atom via a ring carbon atom adjacent to the ring oxygen atom) or a group

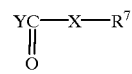

where Y is oxygen, sulphur or NH, X is either a bond, an oxygen atom or a moiety $NR^8$ in which $R^8$ is hydrogen or $C_{1-6}$alkyl, and $R^7$ is $C_{1-10}$alkyl optionally containing one or two double bonds, aryl, aryl$C_{1-4}$alkyl, aryl$C_{2-4}$alkenyl, halo$C_{1-6}$alkyl or $C_{1-6}$alkoxy$C_{1-4}$alkyl), and $R^3$ represents hydrogen, or $R^2$ and $R^3$ may together with the carbon atom to which they are attached represent C=O or C=$NOR^9$ (where $R^9$ is $C_{1-6}$alkyl); and
$R^4$ represents hydroxyl, $C_{1-6}$alkoxy or

(where $R^7$ is as defined above); with the proviso that when $R^1$ represents a hydroxyl group in the axial configuration and $R^4$ is methoxy then $R^2$ cannot represent a group in the axial configuration selected from hydroxyl and OCOCH=$^Z$CH—CH=$^E$CHCH$_3$.

Suitable pharmaceutically acceptable salts of the compounds of formula (I) include inorganic base salts such as alkali metal salts (for example sodium and potassium salts) and ammonium salts and organic base salts. Suitable organic base salts include amine salts such as trialkylamine (e.g. triethylamine), dialkylamine (e.g. dicyclohexylamine), optionally substituted benzylamine (e.g. phenylbenzylamine or p-bromobenzylamine), procaine, ethanolamine, diethanolamine, N-methylglucosamine and tri (hydroxymethyl)methylamine salts and amino acid salts (e.g. lysine and arginine salts).

References hereinafter to a compound of formula (I) includes that compound and its pharmaceutically acceptable salts.

Other salts which are not pharmaceutically acceptable may be useful in the preparation of compounds of formula (I) and these form a further aspect of the invention.

Metabolically labile derivatives of compounds of formula (I) are compounds which are converted in the body into compounds of formula (1). Examples of such derivatives include conventional metabolically labile esters formed from the free carboxylic acid in the molecule.

It is to be understood that the present invention encompasses any individual isomers, including optical isomers, of compounds represented by formula (I) above as well as mixtures thereof, including wholly or partially racemic mixtures thereof.

As used herein, the term "alkyl" as a group or part of a group means a straight or branched chain alkyl moiety comprising, for example, 1 to 8 carbon atoms. Suitable examples include methyl, ethyl, n-propyl, i-propyl, n-butyl, s-butyl, t-butyl, n-hexyl and n-octyl.

As used herein, the term "aryl" as a group or part of a group means phenyl or heteroaryl each optionally substituted by one or more (e.g. 1, 2 or 3) atoms or groups selected from halogen, hydroxyl, $C_{1-6}$alkyl, $C_{1-6}$alkoxy or $C_{1-4}$alkoxycarbonyl. The heteroaryl group may be a 5- or 6-membered heteroaromatic ring containing one or more heteroatoms selected from nitrogen, oxygen and sulphur. Suitable examples of heteroaryl groups include pyridyl, furyl, thienyl and pyrrolyl.

The term "halogen" or "halo" means herein fluorine, chlorine, bromine or iodine.

A halo$C_{1-6}$alkyl group within $R^7$ means a $C_{1-6}$alkyl group containing one or more (e.g. 1, 2 or 3) halogen atoms.

When $R^1$ represents a $C_{1-4}$alkoxy group it may be, for example, a methoxy group. $R^1$ may particularly represent hydrogen, fluorine, hydroxyl or methoxy.

When $R^1$ is a halogen atom or a hydroxyl or $C_{1-4}$alkoxy group, the $R^1$ moiety is preferably sited in the axial configuration. Particularly preferred are compounds of formula (I) in which $R^1$ is hydrogen or hydroxyl (especially when sited in the axial configuration).

Examples of the group $R^2$ include halogen (e.g. fluorine), $C_{1-10}$alkoxy (for example a $C_{1-6}$alkoxy group such as methoxy, ethoxy, n-propoxy or n-hexyloxy), $C_{1-6}$alkylthio (for example a $C_{1-4}$alkylthio group such as methylthio), $C_{1-4}$alkoxy$C_{1-4}$alkoxy (for example a $C_{1-4}$alkoxymethoxy group such as methoxymethoxy), aryl$C_{1-4}$alkyloxy (for example a phenyl$C_{1-4}$alkyloxy group such as benzyloxy), phenyl$C_{3-6}$alkenyloxy (for example OCH$_2$CH=$^E$CHPh), azido, NR$^5$COR$^5$ (where each R$^5$ is independently hydrogen or a $C_{1-4}$alkyl group such as methyl), OR$^6$ (where R$^6$ is, for example, a 2-tetrahydropyranyl group), OCOR$^7$ where R$^7$ is $C_{1-10}$alkyl (e.g. methyl, ethyl, n-propyl, i-propyl, n-butyl, s-butyl, t-butyl, 1-methylpentyl or n-heptyl), $C_{2-10}$alkyl containing one or two double bond (for example a $C_3$alkenyl group such as —C(CH$_3$)=CH$_2$, a $C_6$alkenyl group such as —C(CH$_3$)=C(CH$_2$)$_2$CH$_3$ or a $C_5$diene such as —CH=$^Z$CH—CH=$^E$CHCH$_3$), aryl (e.g. phenyl or p-tolyl), aryl$C_{1-4}$alkyl (for example an arylmethyl group such as benzyl), aryl$C_{2-4}$alkenyl (for example an arylethenyl group such as PhCH=CH—), monohalo$C_{1-4}$alkyl (for example a halopropyl group such as 3-chloropropyl), $C_{1-6}$alkoxymethoxy (e.g. methoxymethoxy or n-butoxymethoxy), OCO$_2$R$^7$ where R$^7$ is $C_{1-10}$alkyl (e.g. n-octyl),

where R$^7$ is $C_{1-10}$ alkyl (for example methyl or n-octyl) or aryl$C_{1-4}$alkyl (for example an arylmethyl group such as benzyl) and R$^8$ is hydrogen or $C_{1-4}$alkyl (e.g. methyl), NHCO$_2$R$^7$ where R$^7$ is $C_{1-6}$alkyl e.g. t-butyl or SCOR$^7$ where R$^7$ is $C_{1-6}$alkyl e.g. methyl.

Alternatively, CR$^2$R$^3$ may represent, for example, C=O or C=NOR$^9$ (where R$^9$ is a $C_{1-4}$alkyl group, e.g. n-propyl).

$R^4$ may particularly represent a $C_{1-4}$alkoxy group such as methoxy or n-propoxy.

A particular group of compounds of the invention are compounds of formula (Ia)

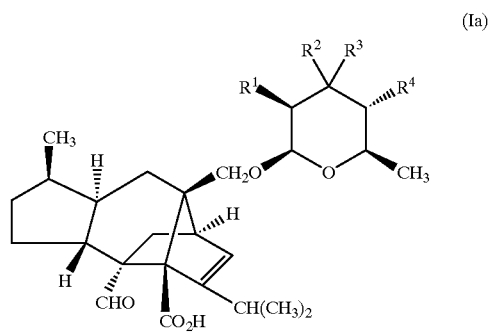

(Ia)

and pharmaceutically acceptable salts and solvates (e.g. hydrates) thereof, wherein $R^1$ to $R^4$ are as defined in formula (I) above.

Preferred compounds of the invention are those compounds of formula (I) or (Ia) in which $R^1$ represents hydrogen or hydroxyl.

Further preferred compounds are those in which $R^2$ is in the axial configuration and $R^3$ is hydrogen. Particular $R^2$ groups include $C_{1-6}$alkoxy, e.g. $C_{1-4}$alkoxy such as methoxy or propoxy, $C_{1-4}$alkoxymethoxy e.g. methoxymethoxy, $C_{1-6}$alkylthio (e.g. $C_{1-4}$alkylthio such as methylthio) azido, or OCOR$^7$ wherein R$^7$ is as defined herein above or more particular $C_{5-8}$ alkyl (e.g. n-heptyl, 1-methylpentyl), phenyl, p-tolyl, 2-phenylethenyl, 1-methylethenyl or 1-methylpent-1-enyl.

Further preferred compounds are those in which $R^4$ is $C_{1-4}$alkoxy (e.g. methoxy or propoxy).

Particularly preferred compounds are those wherein R1 is hydrogen and $R^2$ is $C_{1-4}$alkoxy or methoxymethoxy.

Further particularly preferred compounds are those wherein $R^1$ is hydroxyl and $R^2$ is azido, $C_{1-4}$alkylthio e.g. thiomethyl, or OCOR$^7$ wherein R$^7$ is $C_{4-8}$alkyl, phenyl, tolyl, 2-phenylethenyl, 1-methylethenyl or 1-methylpent-1-enyl.

It is to be understood that the present invention covers all combinations of particular and preferred groups described hereinabove.

The compounds of formula (I) are very active fungicides useful in combatting fungal infections in animals, including humans. For example, they may be used in the treatment of fungal infections caused by organisms such as species of Candida (e.g. *Candida albicans, Candida alabrata, (Torulorsis glabrata), Candida tropicalis, Candida parapsilosis* and *Candida pseudotropicalis*), *Cryptococcus neoformans, Pneumocystis carinii, Asperalilius Sp* (e.g. *Aspergillus flavus* and *Asperaillus fumipatus*), Coccidioides (e.g. *Coccidioides immitis*), Paracoccidioides (e.g. *Paracoccidioides brasiliensis*), Histoplasma (e.g. *Histoplasma capsulatum*) or Blastomyces (e.g. *Blastomyces dermatitidis*). They may also be used to treat other fungal infections caused by species of Candida, Trichophyton, Microsporum or Epidermorhyton (e.g. *Trichophyton mentographytes, Trichophyton rubrum, Microsporum canis* or *Epidermorhyton floccosum*), or in mucosal infections caused by *Candida albicans*.

Compounds of formula (I) may also be used to treat other infections caused by species of filamentous fungi such as Geotrichum (e.g. *Geotrichum clavatum*), Trichosporon (e.g. *Trichosporon beigelii*), Blastoschizomyces (e.g. *Blastoschizomyces capitatus*), Sporothrix (e.g. *Sporothrix schenckii*), Scedosporium (e.g. *Scedosoorium apiosperum*), Cladosporium (e.g. *Cladosporium carrionii*) and *Pityrosporum ovale*.

The compounds of formula (I) may also be used to treat infections caused by protozoa such as Toxoplasma, Cryptosporidium, Leishmania, Tripanosoma, Giardia and Trichomonas.

The in vitro evaluation of the anti-fungal activity of compounds of the invention was performed on liquid or solid medium by the anti-fungal two-fold serial dilution technique of determining the minimum inhibitory concentration (MIC) of anti-fungal agent that inhibited development of growth after 24 to 48 hours of incubation at 37° C. In practice, a series of agar plates or broth microdilution panels containing two-fold dilutions of anti-fungal agent tested were inoculated with a standard culture of a clinically relevant pathogen, for example, *candida albicans*. The agar plates or broth microdulution panels were then examined for the presence or absence of growth of the fungus and the appropriate MIC values were noted.

MFC values (defined as the lowest anti-fungal concentration that killed at least 99.9% of the initial inoculum in liquid medium) may also be determined by sub-culturing 0.01 and 0.1 μl of broth from the drug-free control well, the first well containing growth and each clear well on agar plates.

The in vivo evaluation of compounds of formula (I) can be carried out at a series of dose levels by administration (e.g. subcutaneously, orally, intraperitoneally or intravenously) to mice or rats inoculated with a strain of *Candida albicans*. Untreated animals die within 3 to 9 days and the dose level at which the test compound provides 50% protection against the lethal effect of the infection is noted.

In view of their antifungal activity, compounds of formula (I) recommend themselves for the treatment of a variety of fungal infections in human beings and animals. Such infections include superficial, cutaneous, subcutaneous and systemic mycotic infections such as respiratory tract infections, gastrointestinal tract infections, cardiovascular infections, urinary tract infections, CNS infections, candidiasis and chronic mucocandidiasis (e.g. thrush and vaginal candidiasis) and skin infections caused by fungi, cutaneous and mucocutaneous candidiasis, dermatophytoses including ringworm and tinea infections, athletes foot, paronychia, pityriasis versicolor, erythrasma, intertrigo, fungal nappy rash, candida vulvitis, candida balanitis and otitis extema. They may also be used as prophylactic agents to prevent systemic and topical fungal infections. Use as prophylactic agents may, for example, be appropriate as part of a selective gut decontamination regimen in the prevention of infection in immunocompromised patients (e.g. AIDS patients, patients receiving cancer therapy or transplant patients). Prevention of fungal overgrowth during antibiotic treatment may also be desirable in some disease syndromes or iatrogenic states.

While it is possible that, for use in therapy, compounds of the invention may be administered as the raw chemical, it is preferable to present the active ingredient as a pharmaceutical formulation. The invention thus further provides a pharmaceutical formulation comprising compounds of formula (I) and physiologically acceptable salts thereof together with one or more pharmaceutically acceptable carriers thereof and, optionally, other therapeutic and/or prophylactic ingredients. The carrier(s) must be 'acceptable' in the sense of being compatible with the other ingredients of the formulation and not deleterious to the recipient thereof.

The compositions of the invention include those in a form especially formulated for oral, buccal, parenteral, implant, rectal, topical, ophthalmic or genito-urinary administration or in a form suitable for administration by inhalation or insufflation.

Tablets and capsules for oral administration may contain conventional excipients such as binding agents, for example, syrup, acacia, gelatin, sorbitol, tragacanth, mucilage of starch or polyvinylpyrrolidone; fillers, for example, lactose, sugar, microcrystalline cellulose, maize-starch, calcium phosphate or sorbitol; lubricants, for example, magnesium stearate, stearic acid, talc, polyethylene glycol or silica; disintegrants, for example, potato starch or sodium starch glycollate or crosscarmellose sodium; or wetting agents such as sodium lauryl sulphate. The tablets which include as chewable, dispersible or effervescent tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methyl cellulose, glucoselsugar syrup, gelatin, hydroxyethylcellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example, almond oil, fractionated coconut oil, oily esters, propylene glycol or ethyl alcohol; and preservatives, for example, methyl or propyl p-hydroxybenzoates or sorbic acid.

For buccal administration the composition may take the form of tablets or lozenges formulated in conventional manner.

The composition according to the invention may be formulated for parenteral administration by injection or continuous infusion. Formulations for injection may be presented in unit dose form in ampoules, or in multi-dose containers with an added preservative. The compositions may take such forms as suspensions, solutions, or emulsions in oily or aqueous vehicles, and may contain formulatory agents such as suspending, stabilising and/or dispersing agents. Alternatively the active ingredient may be in powder form for constitution with a suitable vehicle, e.g. sterile, pyrogen-free water, before use.

For administration by inhalation the compositions according to the invention are conveniently delivered in the form of an aerosol spray presentation from pressurised packs with the use of a suitable propellant, e.g. dichlorodifluoromethane, trichlorofluoromethane, dichlorotetrafluoroethane, carbon dioxide or other suitable gas, or from a nebuliser. In the case of a pressurised aerosol the dosage unit may be determined by providing a valve to deliver a metered amount.

Alternatively, for administration by inhalation the compositions according to the invention may take the form of a dry powder composition, for example a powder mix of the compound and a suitable powder base such as lactose or starch or as a modified physical form of the drug substance alone. The powder composition may be presented in unit dosage form in, for example, capsules or cartridges of e.g. gelatin, or blister packs from which the powder may be administered with the aid of an inhaler or insufflator.

The compositions may take the form of a suppository, e.g. containing a conventional suppository base, or a pessary, e.g. containing a conventional pessary base.

The compositions may also be formulated for topical administration in the form of ointments, creams, gels, lotions, shampoos, powders (including spray powders), pessaries, tampons, sprays, dips, aerosols, drops (e.g. eye, ear or nose drops) or pour-ons. Ointments and creams may, for example, be formulated with an aqueous or oily base with the addition of suitable thickening and/or gelling agents. Ointments for administration to the eye may be manufactured in a sterile manner using sterilised components. Pour-ons may, for example, be formulated for veterinary use in oils containing organic solvents, optionally with formulatory agents, e.g. stabilising and solubilising agents. Pessaries and tampons for vaginal insertion may be formulated using conventional techniques and, where appropriate, may contain an effervescent vehicle. Such compositions may also contain other active ingredients such as corticosteroids, antibiotics or antiparasitics as appropriate.

Liquid preparations for intranasal delivery may take the form of solutions or suspensions and may contain conventional excipients such as tonicity adjusting agents, for example, sodium chloride, dextrose or mannitol; preservatives, for example benzalkonium chloride, thiomersal, phenylelklyl alcohol; and other formulating agents such as suspending, buffering, stabilising, dispersing and or flavouring agents.

Transdermal administration may be affected by the design of a suitable system which promotes absorption of the active compound through the skin and would typically consist of a base formulation enclosed within an adhesive stick-on patch comprising backing films, membranes and release liners. Such systems may include absorption enhancers such as alcohols or work by promoting ionotophoresis.

The composition according to the invention may also be formulated as a depot preparation. Such long acting formulations may be administered by implantation (for example subcutaneously or intramuscularly) or by intramuscular injection. Thus, for example, a compound of the invention may be formulated with suitable polymeric or hydrophobic materials (for example as an emulsion in an acceptable oil) or ion exchange resins, or as sparingly soluble derivatives, for example, as a sparingly soluble salt.

When the compositions comprise dosage units, each unit will preferably contain 0.001 mg to 1000 mg, advantageously 0.01 mg to 400 mg, of active ingredient where a compound of the invention is to be administered orally. The daily dosage as employed for adult human treatment will preferably range from 0.001 mg to 5000 mg of active ingredient, most preferably from 0.01 mg to 2000 mg which may be administered in 1 to 4 daily doses, for example, depending on the route of administration and on the condition of the patient and the disease to be treated.

The compound may be administered by intravenous infusion using, for example, up to 50 mg/kg/day of the active ingredient. The duration of treatment will be dictated by the rate of response rather than by arbitrary numbers of days.

Compounds of the invention may also be used in combination with other therapeutic agents, and the invention thus provides, in a further aspect, a combination comprising a compound of the invention together with another therapeutically active agent.

Thus for example the compounds of the invention may be used in combination with one or more other antifungal agents, such as a polienic derivative e.g. (Amphotericin B, Nystatin, a lipid formulation of Amphotericin B) an azole derivative e.g. (Fluconazole, Intraconazole, Ketoconazole, Miconazole, Clotrimazole, ZD-08070, UK-109496), 5-Fluorocytosine, a Pneumocandin or Echinocandin derivative such as Cilofungin, LY-303366, L-733560, and/or one or more immunomodulating agents such as an interferon e.g. (IFN-$\gamma$). interleukine e.g. (IL-1, IL-2, IL-3 and IL-8) and colony stimulating factors, [(G)-CSF, (M)-CSF and (GM)-CSF] and defensines. Particularly advantageous compounds for use with compounds of the invention include Intraconazole, Flucytosine, Fluconazole or Amphotericin B.

When the compounds of the invention are administered in combination with another antifungal agent the compounds of the invention and the other fungal agent can be administered at the recommended maximum clinical dosage or at lower doses.

The combinations referred to above may conveniently be presented for use in the form of a pharmaceutical formulation and thus pharmaceutical formulations comprising a combination as defined above together with a pharmaceutically acceptable carrier thereof comprise a further aspect of the invention. The individual components of such combinations may be administered either sequentially or simultaneously in separate or combined pharmaceutical formulations.

When a compound of the invention is used in combination with a second therapeutic agent against the same condition the dose of each compound may differ from that when the compound is used alone. Appropriate doses will be readily appreciated by those skilled in the art.

According to another aspect of the present invention, we provide a compound of formula (I) or a physiologically acceptable salt thereof or a pharmaceutical composition comprising a compound of formula (I) or a physiologically acceptable salt thereof as defined above for use in therapy, particularly for the treatment of fungal infections in animals (especially humans).

According to another aspect of the present invention, we provide the use of a compound of formula (I) or a physiologically acceptable salt thereof in the manufacture of a medicament for the treatment of fungal infections in a human or non-human animal patient.

According to a further aspect of the present invention, we provide a method of treatment of the human or non-human animal body to combat fungal diseases, which method comprises administering to said body an effective amount of a compound of formula (I) or a physiologically acceptable salt thereof.

It will be appreciated by those skilled in the art that references herein to treatment extend to prophylaxis as well as the treatment of established conditions or infections.

The compounds of the invention may be prepared by the processes described below.

Thus, a general process (A) for the preparation of a compound of formula, (I) comprises reacting a compound of formula (II)

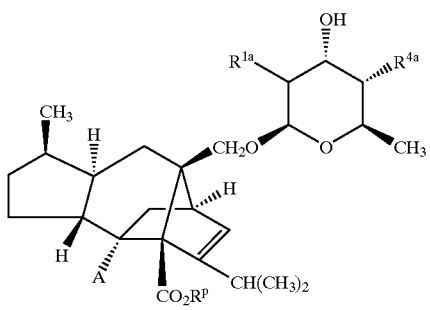

(II)

(in which $R^{1a}$ is as defined for $R^1$ in formula (I) above or is a protected hydroxyl group, $R^{4a}$ is as defined for $R^4$ in formula (I) above or is a protected hydroxyl group, A is a group CHO or a protected derivative thereof and $R^p$ is hydrogen or a carboxyl protecting group) to replace one or more of the free hydroxyl groups with one or more of $R^1$, $R^2/R^3$ and $R^4$, followed by the removal of any protecting groups present.

A first embodiment of process (A) comprises alkylating or alkenylating a compound of formula (II), followed by the removal of any protecting groups present to provide a compound of formula (I) in which $R^2$ is $C_{1-10}$alkoxy, $C_{1-6}$alkoxy$C_{1-4}$alkoxy, aryl$C_{1-6}$alkyloxy, aryl$C_{3-6}$alkenyloxy or $OR^6$ and $R^{1a}$ and $R^{4a}$ are as defined for $R^1$ and $R^4$ in formula (I) above. It will be appreciated that by using appropriate alkylation and alkenylation conditions and protecting groups where necessary, one is able to selectively alkylate or alkenylate the relevant free hydroxyl group(s) without affecting any other labile groups present in a compound of formula (II).

The alkylation or alkenylation reaction may be effected using standard methodology, for example by treating a compound of formula (II) with a strong base such as an alkali metal hydride (e.g. sodium hydride) in a solvent such as an ether (e.g. tetrahydrofuran), followed by the addition of a suitable alkyl or alkenyl halide, optionally in the presence of a tetraalkylammonium halide (e.g. tetra-n-butylammonium fluoride or iodide). The reaction may conveniently be effected at any suitable temperature, for example from room temperature to the reflux temperature of the solvent.

Alternatively, the reaction may be carried out by treating a compound of formula (II) with a tin oxide (e.g. dibutyltin oxide) in a hydrocarbon solvent (e.g. refluxing toluene), followed by the addition of an alkylhalide and a fluoride salt (e.g. tetra-n-butylammonium fluoride) in a suitable solvent such as an ether (e.g. tetrahydrofuran), and heating the mixture in the range of about 30° to 80° C.

The introduction of a $C_{1-6}$alkoxy$C_{1-6}$alkyl group may conveniently be effected using somewhat milder condition than those conditions described above. Thus, for example, a compound of formula (II) may be treated with a suitable alkoxyalkyl halide in the presence of a mild base such as a tertiary amine (e.g. diisopropylethylamine) at a temperature in the range of about 0° to 40° C. The base may also conveniently be the solvent for the reaction.

The introduction of a group $R^6$ may conveniently be effected by treating a compound of formula (II) with a cyclic ether containing one double bond in the ring 2,3-position. The reaction may conveniently be effected in a suitable solvent such as a halogenated hydrocarbon (e.g. dichloromethane) in the presence of a mild acid such as pyridinium p-toluenesulphonate at about room temperature.

According to a further embodiment of process (A), a compound of formula (I) in which $R^2$ represents a group

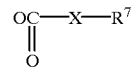

may be prepared by treating a suitably protected compound of formula (II) with an acylating agent, followed by the removal of any protecting groups present. Thus, when X represents a bond or an oxygen atom, the acylation reaction may be effected using any conventional method. For example, one method for preparing compounds in which X is a bond comprises treating a compound of formula (II) with a carboxylic acid $R^7CO_2H$ in the presence of an activating agent such as dicyclohexylcarbodiimide and a suitable base such as 4-dimethylaminopyridine in a solvent such as a halogenated hydrocarbon (e.g. dichloromethane) at about room temperature. Alternatively, the reaction with a carboxylic acid $R^7CO_2H$ may be effected in the presence of 2-chloro-1-methylpyridinium iodide and a suitable base system such as 4-dimethylaminopyridine optionally also comprising a tertiary amine such as triethylamine, conveniently in a halogenated hydrocarbon solvent (e.g. dichloromethane) at a temperature of from about 20° to the reflux temperature of the solvent. An activated acid such as a carboxylic acid halide (for example a carboxylic acid chloride $R^7COCl$) or a carboxylic anhydride such as acetic anhydride may also be used, whereby the acylation may be effected either by directly reacting a compound of formula (II) with the acid halide in the presence of a suitable base such as 4-dimethylaminopyridine, pyridine or a trialkylamine (e.g. triethylamine) or a mixture of suitable bases in a suitable solvent such as acetonitrile or dichloromethane or by addition of the acid halide $(R^7CO)_2O$ following pretreatment of a compound of formula (II) with a tin oxide (e.g. dibutyltin oxide) in a hydrocarbon solvent (e.g. refluxing toluene). Similar conditions using a haloformate (for example a chloroformate $R^7OCOCl$) may conveniently provide compounds in which $R^2$ represent $OCO_2R^7$.

When X represents NH, the acylation reaction may conveniently be effected using a suitable isocyanate $R^7NCO$ in the presence of a tin catalyst (e.g. a dialkyltin diacetate such as dibutyltin diacetate) and in a solvent such as an aromatic hydrocarbon (e.g. toluene) conveniently under reflux.

When X represents NAlkyl, the acylation reaction may conveniently be effected using a reagent $HalCONR^7R^8$ (where Hal is a halogen atom, e.g. chlorine) in the presence of a strong base such as an alkali metal amide (e.g. lithium diisopropylamide) and in a solvent such as an ether (e.g. tetrahydrofuran) conveniently at a temperature in the range of about 0° C. to room temperature.

In another embodiment of process (A), a compound of formula (I) in which $R^1$ is hydroxyl and $R^2$ is azido or $C_{1-10}$alkylthio may be prepared from a compound of formula (II) in which $R^{1a}$ is hydroxyl, $R^{4a}$ is $C_{1-6}$alkoxy, A is a group CHO or a protected derivative thereof and $R^p$ is a carboxyl protecting group via a compound of formula (III) or (IV)

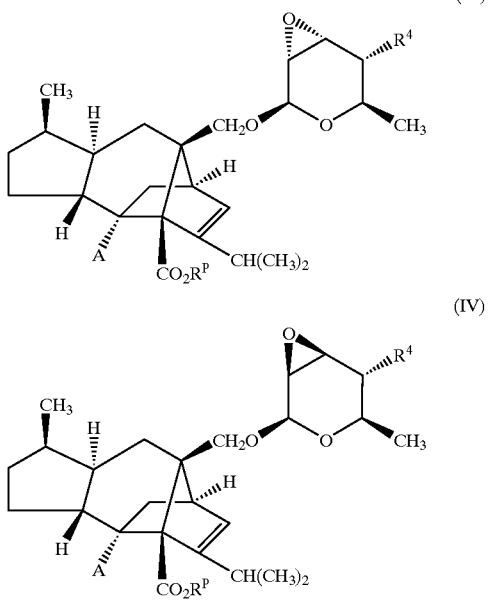

(wherein A and $R^p$ are as defined just above and $R^4$ is $C_{1-6}$alkoxy, e.g. methoxy), followed by the removal of any protecting groups present.

The nucleophilic ring opening of the epoxide in (III) or (IV) may conveniently be effected by the addition of an alkali metal azide (e.g. lithium azide) or an alkali metal thioalkoxide (e.g. sodium thiomethoxide) in a suitable solvent such as dimethylformamide. The reaction with an azide may conveniently be effected at an elevated temperature, for example within the range of about 80° to 120° C. The reaction with a thioalkoxide may conveniently be effected at about room temperature. It will be appreciated that the nucleophilic ring opening reaction provides compounds in which the $R^1$ hydroxyl group is in the opposite plane to the $R^2$ azido or $C_{1-10}$alkylthio group. The particular configuration will depend upon the choice of a compound of formula (III) or (IV) as the starting material.

In a further embodiment of process (A), a compound of formula (I) in which $R^1$ and $R^2$ both represent hydrogen atoms may conveniently be prepared from a suitably protected compound of formula (II) in which $R^{1a}$ is a hydroxyl group by treating said compound with a reducing system capable of converting the 2', 3'-diol group to a 2',3'-ene group and thereafter hydrogenating the unsaturated compound in the presence of a palladium catalyst (e.g. palladium-on-carbon), followed, where necessary, by the removal of any protecting groups remaining. The initial reaction may conveniently be effected by treating the diol with zinc and iodine following the addition of a triarylphosphine (e.g. triphenylphosphine) and imidazole. The reaction may be carried out, for example, in a solvent such as refluxing toluene.

Compounds of formulae (III) and (IV) may conveniently be prepared treating a compound of formula (II) in which $R^{1a}$ is hydroxyl, $R^{4a}$ is $C_{1-6}$alkoxy, A is a group CHO or a protected derivative hereof and $R^p$ is a carboxyl protecting group to convert the free hydroxyl groups to leaving groups such as alkyl- or arylsulphonyloxy groups followed by treatment with a strong base such as an alkali metal hydride (e.g. sodium hydride) in a suitable solvent such as dimethylformamide, conveniently at about room temperature. Alternatively, sodium in an alcoholic solvent (e.g. methanol) may be used to form the epoxide ring. In this instance the base system is added to a solution of the reactive intermediate in a suitable solvent such as a halogenated hydrocarbon (e.g. dichloromethane) and the reaction conveniently carried out at a temperature of from about room temperature to reflux. The reaction provides a mixture of compounds of formulae (III) and (IV) which may conveniently be separated by flash column chromatography.

The conversion of the free hydroxyl groups in appropriate compounds of formula (II) to leaving groups may be effected using conventional methodology. Thus, for example, alkyl- or arylsulphonyloxy groups may be introduced by reaction with an alkyl- or arylsulphonyl halide in the presence of a suitable solvent such as a halogenated hydrocarbon (e.g. dichloromethane) and optionally also comprising an amine base (e.g. 4-dimethylaminopyridine). The reaction may conveniently be carried out at about room temperature.

According to a further embodiment of process (A), one or more free hydroxyl groups in a compound of formula (II) may be converted to a halogen atom using conventional displacement methods. Thus, for example, replacement with iodine may conveniently be effected by treatment with iodine in the presence of triphenylphosphine and imidazole in a suitable solvent such as an aromatic hydrocarbon (e.g. toluene) at an elevated temperature, for example under reflux. Replacement with fluorine may conveniently be effected by treatment with a suitable fluorinating agent such as diethylaminosulfur, trifluoride (DAST) in the presence of a solvent such as a halogenated hydrocarbon (e.g. dichloromethane) or an aromatic hydrocarbon (e.g. toluene). The reaction may conveniently be effected about room temperature.

Another embodiment of process (A) comprises oxidising a compound of formula (II) followed by the removal of any protecting groups present to provide a compound of formula (I) in which $CR^2R^3$ represents C=O. The oxidation reaction may conveniently be effected using a suitable oxidising agent such as dimethylsulfoxide in the presence of trifluoroacetic anhydride. The oxidation conveniently taken place in the presence of a suitable solvent such as a halogenated hydrocarbon (e.g. dichloromethane), optionally comprising a suitable amine base (e.g. triethylamine), at a reduced temperature (e.g. from about −78° to 0° C.).

Another general process (B) comprises an interconversion reaction wherein a compound of formula (I) is prepared from a different compound of formula (I) or a protected derivative thereof.

According to a first embodiment of process (B), a protected derivative of a3 compound of formula (I) in which $R^2$ is azido may be converted to a compound of formula (I) in which $R^2$ is $NR^5COR^5$. The $R^2$ conversion may conveniently be effected by reducing the azido group to $NH_2$ by hydrogenation, for example in the presence of a suitable palladium catalyst (e.g. palladium on charcoal), and then acylating the amine under conventional conditions, for example by addition of a carboxylic acid anhydride in the presence of a suitable base (e.g. pyridine), followed, when $R^5$ is $C_{1-6}$alkyl, by alkylation by treating the amide with a suitable base (e.g. sodium hydride) in a solvent such as an ether (e.g. tetrahydrofuran) and then adding a suitable alkylating agent such as an alkyl halide.

In another embodiment of process (B), a compound of formula (I) in which $R^2$ is an azido group or the group $SCOR^7$ may be prepared by treating a protected derivative of a corresponding compound of formula (I) in which $R^2$ is a halogen atom (e.g. iodine) with an alkali metal azide (e.g.

lithium azide) or a salt e.g. sodium or cesium salt of the thiocarboxylic acid $R^7COSH$ in a solvent such as dimethylformamide at an elevated temperature (e.g. 50° to 120° C.), followed by the removal of any protecting groups present.

A further embodiment of process (B) comprises reducing a compound of formula (I) in which $R^2$ is a halogen atom (e.g. iodine) to provide, following the removal of any protecting groups present, a corresponding compound of formula (I) in which $R^2$ is hydrogen. The reduction may conveniently be effected using a suitable reducing agent such as a tin hydride (e.g. a trialkyltin hydride such as tributyltin hydride) in the presence of an activating agent such as azobis (isobutyronitrile) in a solvent such as refluxing toluene.

A further embodiment of process (B) comprises alkylating a protected derivative of a corresponding compound of formula (I) in which $R^1$ and/or $R^4$ is hydroxyl under the conditions described in the first embodiment of process (A) hereinabove.

In a further embodiment of process (B), a compound of formula (I) in which $CR^2R^3$ is a group $C=NOR^9$ may be prepared by treating a protected derivative of a corresponding compound of formula (I) in which $CR^2R^3$ is $C=O$ with a reagent $R^9ONH_2$ or a salt thereof (e.g. the hydrochloride salt) in a suitable solvent (e.g. pyridine) at an elevated temperature (e.g. from about 60° to 100° C.), followed by the removal of any protecting groups present.

In any of the aforementioned procedures where an alkyl moiety is introduced as a group or part of a group, it may be appropriate to first introduce the corresponding unsaturated moiety and thereafter reduce the alkenyl group to the desired alkyl group, for example by hydrogenation in the presence of a palladium catalyst (e.g. 10% palladium on charcoal) at about room temperature.

Many of the above-mentioned procedures require the removal of one or more protecting groups as a final step to provide the desired compound of formula (I). Thus, a further general process (C) comprises deprotecting a protected derivative of a compound of formula (I). Suitable carboxyl protecting groups and hydroxyl protecting groups for use herein include any conventional protecting group, for example as described in "Protective Groups in Organic Chemistry", Ed. J. F. W. McOmie (Plenum Press, 1973) or "Protective Groups in Organic Synthesis" by Theodora W. Greene (John Wiley and Sons, 1991). Examples of suitable carboxyl protecting groups include aralkyl groups such as diphenylmethyl and silyl groups (e.g. trimethylsilylethyl). Examples of suitable hydroxyl protecting groups include arylalkyl groups such as p-methoxybenzyl, acyl groups such as acetyl and ester group such as 2,2,2-trichloroethoxycarbonyl or benzyloxycarbonyl. Aldehyde groups may conveniently be protected in the form of cyclic ketals.

The protecting groups may be removed using conventional techniques. Thus, a diphenylmethyl group may conveniently be removed using trifluoroacetic acid or by hydrogenolysis in the presence of a palladium catalyst (e.g. 10% palladium on charcoal). Trifluoroacetic acid may conveniently be employed where other groups are present which are sensitive to hydrogenation. A p-methoxybenzyl group may conveniently be removed using 2,3-dichloro-5,6-dicyano-1,4-benzoquinone. Silyl groups such as trimethylsilylethyl may conveniently be removed using fluoride ions. Cyclic ketal groups may conveniently be converted to aldehyde group by the addition of a suitable acid such as hydrochloric acid. An acyl group such as acetyl may conveniently be removed under basic conditions, for example using an alkoxide (e.g. sodium methoxide). An ester group such as 2,2,2-trichloroethoxycarbonyl may conveniently be removed by adding zinc and potassium dihydrogen phosphate.

Compounds of formula (II) may conveniently be prepared from sordarin or 4'-demethylsordarin, a compound of formula (V)

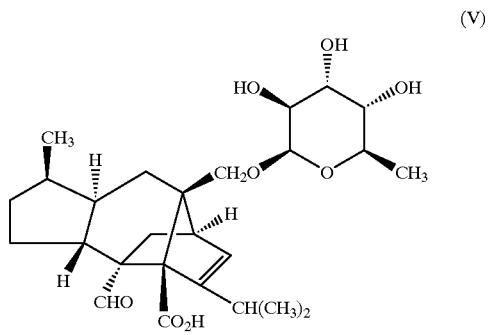

(V)

Thus, for example, compounds of formula (II) may be prepared from sordarin or 4'-demethylsordarin by appropriate protection using conventional methods as described above, followed where necessary by converting one or more of the hydroxyl groups to other groups specified in formula (II) above.

When the carboxyl group in sordarin or a compound of formula (V) is protected with a diphenylmethyl group the protection reaction may conveniently be carried out by treating a solution of sordarin or a compound of formula (V) in an alcoholic solvent (e.g. methanol) or a halogenated hydrocarbon (e.g. dichloromethane) or a mixture of such solvents with diphenyldiazomethane, conveniently added as a solution in a halogenated hydrocarbon solvent (e.g. dichloromethane).

When a hydroxyl group in a carboxyl protected derivative of sordarin or a compound of formula (V) is protected with a p-methoxybenzyl group this group may be introduced by reaction with a tin oxide (e.g. dibutyltin oxide) in a hydrocarbon solvent (e.g. refluxing toluene), followed by the addition of a p-methoxybenzyl halide in the presence of an fluoride salt (e.g. tetrabutylammonium fluoride). When protected with a benzyloxycarbonyl group, this group may be introduced by reaction with a benzylhaloformate in the presence of a suitable amine base such as 4-dimethylaminopyridine and in a solvent such as a halogenated hydrocarbon (e.g. dichloromethane) or acetonitrile.

When $R^{1a}$ in a compound of formula (II) is hydrogen such compounds may conveniently be prepared from sordarin or 4'-demethylsordarin by appropriate protection of labile groups followed by removal of the 2'-hydroxyl group. Removal of the hydroxyl group to provide a compound in which $R^{1a}$ is hydrogen may conveniently be effected in two steps comprising (i) forming an S-alkyldithiocarbonate by treatment with a strong alkali metal base (e.g. sodium hydride), in the presence of imidazole, and in a suitable solvent such as an ether (e.g. tetrahydrofuran) at a reduced temperature (e.g. about 0° C.), and then adding carbon disulphide and an alkylhalide (e.g. methyliodide) at about room temperature and (ii) removing this group by treating a solution of the intermediate compound in a hydrocarbon solvent (e.g. toluene) at an elevated temperature (e.g. about 80° to 120° C.) with a hydride reducing agent (e.g. a trialkyltin hydride such as tributyltin hydride), optionally in the presence of an activating agent [e.g. azobis (isobutyronitrile)].

Compounds of formulae (II), (III), (IV) and (V) are novel intermediates and form further individual aspects of the present invention. The compound of formula (V), 4'-demethylsordarin, represents a particular aspect of the present invention.

Base salts of compounds of formula (I) may be conveniently formed by treating a compound of formula (I) with an appropriate salt or base. Thus, for example, salts may conveniently be prepared by treating a compound of formula (I) with a salt or a base selected from sodium or potassium hydroxide, hydrogen carbonate, carbonate or acetate (e.g. potassium hydroxide, potassium hydrogen carbonate, sodium hydrogen carbonate or potassium acetate), ammonium acetate, calcium acetate and L-lysine as appropriate. The salt may, for example, be prepared by adding the appropriate salt or base (if necessary as an aqueous solution) to a solution or suspension of the compound of formula (I) in a suitable solvent such as an alcohol (e.g. methanol) or dioxane at temperatures of for example 0° C. to 80° C. and conveniently at about room temperature.

Pharmaceutically acceptable salts may also be prepared from other salts, including other pharmaceutically acceptable salts of the compounds of formula (I), using conventional methods.

The novel compound of formula (V) may conveniently be prepared according to the fermentation process described hereinafter or by demethylating sordarin using a biotransformation procedure. It is to be understood that such processes for the preparation of the compound of formula (V) represent further aspects of the present invention.

The fermentation process comprises cultivating a microorganism capable of producing the compound of formula (V) and thereafter isolating the compound of formula (V) from the culture.

Microorganisms capable of producing the compound of formula (V) will conveniently be mutant strains of *Sordaria araneosa* which can be identified by screening survivors of mutagenesis by analysing a test sample obtained from fermentation of the microorganism using standard methodology. In particular, the microorganism to be conveniently used is a mutant strain of *Sordairia araneosa* deposited in the permanent culture collection of the CAB International Mycological Institute, Genetic Resource Reference Collection, Bakeham Lane, Egham, Surrey TW20 9TY, England. The strain was received by the Institute on Jun. 10, 1994 and was subsequently given the accession number IMI 362184 and dates of acceptance and confirmation of viability of Jun. 13 and 21 1994 respectively. The Institute is an International Depository authority recognised under the Budapest Treaty. The characteristics thus far identified for IMI 362184 are given in Example 46.

The present invention provides in a further aspect the microorganism IMI 362184 per se and mutants thereof.

Mutants of the IMI 362184 may arise spontaneously or may be produced by a variety of methods including those outlined in Techniques for the Development of Microorganisms by H I Adler in "Radiation and Radioisotopes for Industrial Microorganisms", Proceedings of the Symposium, Vienna 1973, p241, International Atomic Energy authority. Such methods include ionising radiation, chemical methods, e.g. treatment with N-methyl-N'-nitro-N-nitrosoguanidine (NTG), heat, genetic techniques, such as recombination and transformation, and selective techniques for spontaneous mutants.

The preparation of the compound of formula (V) by fermentation may be effected by conventional means i.e. by culturing a suitable organism in the presence of assimilable sources of carbon, nitrogen and mineral salts, and thereafter isolating the desired product.

Assimilable sources of carbon, nitrogen and minerals may be provided by either simple or complex nutrients. Sources of carbon will generally include glucose, maltose, starch, glycerol, molasses, dextrin, lactose, sucrose, fructose, galactose, myo-inositol, D-mannitol, soya bean oil, carboxylic acids, amino acids, glycerides, alcohols, alkanes and vegetable oils. Sources of carbon will generally comprise from 0.5 to 10% by weight of the fermentation medium. Fructose, glucose and sucrose represent preferred sources of carbon.

Sources of nitrogen will generally include soya bean meal, corn steep liquors, distillers solubles, yeast extracts, cottonseed meal, peptones, ground nut meal, malt extract, molasses, casein, amino acid mixtures, ammonia (gas or solution), ammonium salts or nitrates. Urea and other amides may also be used. Sources of nitrogen will generally comprise from 0.1 to 10% by weight of the fermentation medium.

Nutrient mineral salts which may be incorporated into the culture medium include the generally used salts capable of yielding sodium, potassium, ammonium, iron, magnesium, zinc, nickel, cobalt, manganese, vanadium, chromium, calcium, copper, molybdenum, boron, phosphate, sulphate, chloride and carbonate ions.

Cultivation of the organism will generally be effected at a temperature of from 20° to 40° C., preferably from 20 to 35° C., especially about 25° C., and will desirably take place with aeration and agitation e.g. by shaking or stirring. The medium may initially be inoculated with a small quantity of mycelium and/or spores. The vegetative inoculum obtained may be transferred to the fermentation medium, or to one or more seed stages where further growth takes place before transfer to the principal fermentation medium. The fermentation will generally be carried out in the pH range 3.5 to 9.5, preferably 4.5 to 7.5. It may be necessary to add a base or an acid to the fermentation medium to keep the pH to within the desired range. Suitable bases which may be added include alkali metal hydroxides such as aqueous sodium hydroxide or potassium hydroxide. Suitable acids include mineral acids such as hydrochloric, sulphuric or phosphoric acid.

The fermentation may be carried out for a period of 4–30 days, preferably about 5–15 days. An antifoam may be present to control excessive foaming and added at intervals as required. Carbon and/or nitrogen sources may also be fed into the fermentation medium as required.

The compound of formula (V) is associated mainly with the cells and may be brought into solution either by addition of an acid and a water-miscible organic solvent, or more preferably by addition of a base (e.g. sodium hydroxide). Cells may be separated from these solutions either by centrifugation, conventional filtration or membrane filtration. The liquor may be optionally thereafter treated with an acid such as sulphuric acid until the pH is below 6 (e.g. about pH 4.5).

The compound of formula (V) may be isolated and purified by a variety of fractionation techniques, for example adsorption-elution, precipitation, fractional crystallisation, solvent extraction and liquid-liquid partition which may be combined in various ways.

Adsorption onto a solid support followed by elution has been found to be particularly suitable for isolating and purifying the compound of formula (V).

Suitable solid supports include silica; a non-functional macroreticular adsorption resin, for example cross-linked styrene divinyl benzene polymer resins such as CG161 and Amberlite XAD-2, XAD4, XAD-16 or XAD-1180 resins (Rohm & Haas Limited) or Kastell S112 (Montedison); a substituted styrene-divinyl benzene polymer such as Diaion SP207 (Mitsubishi); an anion exchanger [e.g. IRA-958 or MacroPrep High Q (BioRad)], an organic solvent-compatible cross-linked dextran such as Sephadex LH20 (Pharmacia UK Limited), or on reverse phase supports such as hydrocarbon linked silica, e.g. $C_{18}$-linked silica.

The compound of formula (V) may also be isolated and purified by the use of a liquid anion exchanger such as LA 2.

Suitable solvents for the elution of the compound of formula (V) will, of course, depend on the nature of the absorbent. When using a polymer resin such as XAD-16 water-miscible solvents such as methanol, acetone, isopropanol or acetonitrile in various proportions in water may be particularly suitable.

The presence of the compound of formula (V) during the extraction/isolation procedures may be monitored by conventional techniques such as high performance liquid chromatography (HPLC) or UV spectroscopy or by utilising the optical rotation or other property of the compound.

Where the compound of formula (V) is obtained in the form of a solution in an organic solvent, for example after purification by absorption/elution, the solvent may be removed by conventional procedures, e.g. by evaporation, to yield the required compound. If desired, the compound may be further purified by chromatographic techniques such as countercurrent chromatography using a coil extracter such as a multi-layer coil extracter or high performance liquid chromatography or supercritical fluid chromatography on adsorbents such as carbon, alumina, vanadium, polymeric resins or silica, with or without bonded phases. Suitable solvents/eluents for the chromatographic purification/ separation of the compound of formula (V) will of course depend on the nature of the adsorbent. When using a C8 bonded silica, mixtures of acetonitrile and water are particularly suitable. Alternatively, the compound may be further purified by solvent extraction, for example using an appropriate organic solvent such as a ketone (e.g. acetone or methyl ethyl ketone), a halogenated hydrocarbon, an alcohol (e.g. methanol), a diol (e.g. propane-1,2-diol or butane-1,3-diol) or an ester (e.g. methyl acetate or ethyl acetate). In a further alternative, solutions of compound (V) may be further purified by treatment with adsorbents that selectively remove impurities when added at appropriate levels (e.g. DEAE-cellulose) or by crystallisation (e.g. from a mixture of acetonitrile and water) or using a combination of the above procedures.

The biotransformation of sordarin to 4'-demethylsordarin, the compound of formula (V), may be effected by incubating sordarin in a culture comprising a suitable organism and sources of carbon and nitrogen, including those sources specified hereinabove, and thereafter isolating the compound of formula (V) from the culture.

Microorganisms capable of demethylating sordarin at the 4'-position may readily be identified by using a small scale test and analysing a test sample obtained using standard methodology, for example, using HPLC. Examples of microorganisms which have been identified as sordarin demethylators include *Streptomyces capreolus* ATCC 31963, *Streptomyces avermitilis* ATCC 31272, *Streptomyces armentosus* NRRL 3176, *Streptomyces antibioticus* ATCC 31771, *Streptomyces rimosus* ATCC 23955, *Streptomyces platensis* ATCC 29778, *Streptomyces mashuensis* ATCC 23934, *Streptomyces eurythermus* ATCC 14975, *Nocardia orientalis* ATCC 43491 and *Cunninghamella echinulata* var elegans ATCC 36112.

Cultivation of the organism will generally be effected at a temperature of from 20° to 40° C., preferably from 20° to 35° C., especially about 28° C., and will desirably take place with aeration and agitation, e.g. by shaking or stirring. The medium may initially be inoculated with a small quantity of mycelium and/or spores. The vegetative inoculum obtained may be transferred to the fermentation medium or to one or more seed stages where further growth (e.g. over about 1–3 days) takes place before transfer to the principal fermentation medium. The principal fermentation medium will also comprise sordarin and the fermentation will generally be carried out in a pH range of 3.5 to 9.5, preferably 4.5 to 7.5. It may be necessary to add a base or an acid to the fermentation medium to keep the pH to within the desired range. Suitable bases which may be added include alkali metal hydroxides such as aqueous sodium hydroxide or potassium hydroxide. Suitable acids include mineral acids such as hydrochloric, sulphuric or phosphoric acid. Fermentation may be carried out over a period of 2 to 5 days, preferably about 3 days. An antifoam may be present to control excess foaming and added at intervals as required. Carbon and/or nitrogen sources may also be fed into the fermentation medium as required.

The separation and isolation of the compound of formula (V) from the fermentation broth may be effected by the general procedures previously described. When it is desired to lower the pH of the liquor to below pH 6 (e.g. to about pH 2.5) this may conveniently be achieved by the addition of an acid such as orthophosphoric acid.

It will be appreciated that biotransformation may be effected according to a number of alternative methods. For example, cells may be grown and harvested prior to addition to a solution of sordarin in, for example, buffer, spent fermentation medium or water. It is also feasible that the appropriate enzymes could be isolated and used (with appropriate co-enzymes) or the enzymes cloned and overexpressed.

As stated hereinabove, sordarin is a known compound, which may be obtained using procedures described in the relevant art. Thus, for example, the preparation of sordarin by the cultivation of *Sordaria araneosa* NRRL 3196 (also deposited in the ATCC as ATCC 36386) is described in British Patent Specification No. 1,162,027. Specific examples of the preparation of sordarin using similar procedures are reported hereinafter.

Sordaricin may conveniently be prepared under fermentation conditions similar to those described for preparing sordarin using *Sordaria araneosa* NRRL 3196 or a suitable mutant thereof, with isolation of the desired compound using appropriate chromatographic means. One such mutant has been deposited in the permanent culture collection of the CAB International Mycological Institute, Genetic Resource Reference Collection, Bakeham Lane, Egham, Surrey TW20 9TY, England. The strain was received and accepted by the Institute on Aug. 11, 1994 and was subsequently given the accession number IMI 362947 and a date of confirmation of viability of Aug. 19, 1994. The Institute is an International Depository authority recognised under the Budapest Treaty. The characteristics thus far identified for IMI 362947 are given in Example 47.

The present invention provides in a further aspect the microorganism IMI 362947 per se and mutants therof.

Processes for obtaining mutants of IMI 362947 and its genetic material will be similar to those described hereinabove for the manipulation of IMI 362184.

Sordaricin may also be prepared from sordarin using a biotransformation procedure. The biotransformation may conveniently be effected by incubating sordarin in a culture comprising a suitable organism and sources of carbon and nitrogen, including those sources specified hereinabove, and thereafter isolating sordaricin from the culture.

Microorganisms capable of converting sordarin to sordaricin may readily be identified by using a small scale test and analysing a test sample obtained using standard methodology, for example, using HPLC. We have identified one such microorganism and deposited it with the National Collections of Industrial and Marine Bacteria Limited (NCIMB), 23 St. Machar Drive, Aberdeen AB2 1RY, Scotland. The strain was received by the NCIMB on Aug. 4, 1994 and was the same day accepted for deposit for patent purposes and the viability of the microorganism confirmed. The microorganism, which is a Coryneform species having the characteristics given in Example 48, has been assigned the accession number NCIMB 40675. The NCIMB is an International Depository authority recognised under the Budapest Treaty.

The invention thus provides in another aspect the microorganism NCIMB 40675 per se and mutants thereof.

According to another aspect of the present invention we provide the genetic material of NCIMB 40675 and mutants thereof that participates in the bioconversion of sordarin to sordaricin.

Processes for obtaining mutants of NCIMB 40675 and its genetic material will be similar to those described hereinabove for the manipulation of IMI 362184.

Cultivation of the NCIMB 40675 will generally be effected at a temperature of from 20° to 40° C., preferably from 20° to 35° C., especially about 28° C., and will desirably take place with aeration and agitation, e.g. by shaking or stirring. The medium may initially be inoculated with a small quantity of mycelium and/or spores. The vegetative inoculum obtained may be transferred to the fermentation medium or to one or more seed stages where further growth (e.g. over about 1–3 days) takes place before transfer to the principal fermentation medium. The principal fermentation medium will also comprise sordarin and the fermentation will generally be carried out in a pH range of 3.5 to 9.5, preferably about 7.5. It may be necessary to add a base or an acid to the fermentation medium to keep the pH to within the desired range. Suitable bases which may be added include alkali metal hydroxides such as aqueous sodium hydroxide or potassium hydroxide. Suitable acids include mineral acids such as hydrochloric, sulphuric or phosphoric acid. Fermentation may be carried out over a period of 4 to 8 days, preferably about 6 days. An antifoam may be present to control excess foaming and added at intervals as required. Carbon and/or nitrogen sources may also be fed into the fermentation medium as required.

It will be appreciated that biotransformation may be effected according to a number of alternative methods. For example cells may be grown and harvested prior to addition to a solution of sordarin in, for example, buffer, spent fermentation medium or water. It is also feasible that the appropriate enzymes could be isolated and used or the enzymes cloned and overexpressed.

The separation and isolation of sordaricin from the fermentation broth may be effected by the general procedures previously described. When it is desired to lower the pH of the liquor to about pH 6 this may conveniently be achieved by the addition of an acid such as orthophosphoric acid.

It is to be understood that the fermentation and bioconversion processes described hereinabove for preparing sordaricin represent further aspects of the present invention.

The examples hereinafter illustrate aspects of the present invention and are not intended to limit the invention in any way.

PREPARATION 1

Production of sordarin

A culture of *Sordaria araneosa* NRRL3196 (ATCC36386) was grown on an agar medium until mature growth occurred. 6 mm diameter plugs of the agar containing the growth were transferred to sterile water or Brain Heart Infusion broth (Oxoid)+10% glycerol and stored at ambient temperature or −140° C. respectively. A suspension containing 2 of these agar plugs was used to inoculate a 250 ml Erlenmyer flask containing 50 ml of medium FS.

| Medium FS | g/L |
| --- | --- |
| Peptone(Oxoid L34) | 10 |
| Malt extract (Oxoid L39) | 21 |
| Glycerol (Glycerine CP) | 40 |
| Junlon 110 (Honeywell & Stein) | 1 |
| Distilled water | |

The culture was incubated at 25° C. for 5 days on a rotary shaker operated at 250 rpm with a 50 mm diameter orbital motion. Aliquots (2 ml) of the developed inoculum were used to inoculate further 250 ml Erlenmyer flasks containing medium FS (50 ml) which were incubated as described above. 80 ml of the bulked shake flask developed inoculum was used to inoculate each of two 7L fermenters containing 5L of medium FS. The fermentations were controlled to a temperature of 25C. The culture was agitated at 400 rpm and aerated at 2 Lpm. After 3 days fermentation, 10L of culture was used to inoculate a 780L fermenter containing 500L of medium SM55VAR.

| SM55VAR | g/L |
| --- | --- |
| Glucidex 32D (Roquette Frere) | 74 |
| Peptone (Oxoid L37) | 10 |
| Proflo (Traders Protein) | 30 |
| Beet molasses | 15 |
| $MgSO_4.7H_2O$(BDH) | 5 |
| $CaCO_3$(BDH) | 5 |
| $FeSO_4.7H_2O$(Sigma) | 2 |
| $ZnSO_4.7H_2O$(BDH) | 0.04 |
| L-trytophan(Sigma) | 2 |
| PPG2000 (K & K Greef) | 0.5 |
| Silicone 1520 (Dow Corning) | 0.04 |
| Distilled water | |

The fermentation was controlled to a temperature of 25° C. The broth was agitated at 300–350 rpm and aerated at 200 Lpm. 70% (w/v) Meritose (Tunnel Refineries) solution was fed to the culture to maintain a positive residual glucose concentration. Distilled water was fed to maintain a culture volume of 500L. PPG2000 antifoam was added on demand to control foaming. Whole broth extracts (in aqueous acetonitrile +1% trifluoroacetic acid) were assayed for presence of sordarin by reverse phase HPLC. The culture was harvested after 11 days when the extract of a broth sample indicated a sordarin titre of 0.6 g/L. Fermentation broth was made 0.1M with respect to sodium hydroxide and after storage at ambient temperature overnight was filtered through Dicalite on a rotary vacuum filter (1% Dicalite was added to the broth as filter aid). The filtrate was adjusted to pH 6–7 with concentrated sulphuric acid and the solution was applied to XAD16 resin (10 volumes of filtrate/volume resin). The adsorbent was washed with water and acetone::water (1:3) in both cases to give a clear effluent before sordarin was eluted with acetone:water (3:1; 2 column volumes collected). Flow rate throughout the process was between 1–2 column volumes/hr. The eluate was concentrated to a small volume (8.5L). The concentrate was adjusted to pH 3 with phosphoric acid and stood overnight at ambient temperature to allow precipitated sordarin to settle. Supernatant was decanted then centrifuged and the supernatant was discarded. Centrifuge pellets and precipitate were taken up in 75% aqueous acetonitrile to give 3.9L of a dark brown solution. To this was added 1.0L 0.2M $NH_4H_2PO_4$ with stirring, and the solution was adjusted to pH 4.0 with phosphoric acid, to give a final volume of 5.0L with approximate composition 60% acetonitrile –0.1M $NH_4H_2PO_4$. The crude sordarin solution (5.0L) from above was subjected to preparative HPLC in 10 injections (450–550 ml each) on a column (15 cm ×25 cm) of 7 mm Kromasil C8 in mobile phase of 50% acetonitrile –0.1M $NH_4H_2PO4$, pH 4 (50L acetonitrile made up to 100 L with water containing 575 g $NH_4H_2PO_4$ and 40 ml $H_3PO_4$), flow-rate 600ml/min, detection by UV absorbance ($\lambda$210 nm). The fraction eluting between 15.4 and 19.2 min was collected. Pooled fractions from the 10 injections (23L) were diluted with water to 50L and this solution was pumped back through the Kromasil column at 28L/h. The column was washed with water (25L) then eluted with 90% acetonitrile (10L). The eluate was evaporated to a residue of 1300 ml which was freeze-dried to yield the title compound as a buff powder (105.6 g). MS and NMR analysis of the product showed equivalence with an authentic sample of sordarin.

PREPARATION 2
Production of sordarin potassium salt

*Sordaria araneosa* NRRL3196 (ATCC36386) was maintained in Brain Heart Infusion broth (Oxoid)+10% glycerol at –140° C. as described in Preparation 1. A suspension containing 2 agar plugs was used to inoculate a 250 ml Erlenmyer flask containing 50 ml of medium FS. The culture was incubated at 25° C. for 5 days on a rotary shaker operated at 250 rpm with a 50 mm diameter orbital motion. Aliquots (2 ml) of the developed inoculum were used to inoculate further 250 ml Erlenmyer flasks containing medium FS (50 ml) and incubated as described above. 80 ml of the bulked shake flask developed inoculum was used to inoculate each of two 7L fermenters containing 5L of medium FS. The fermentations were controlled to a temperature of 25° C. The culture was agitated at 400 rpm and aerated at 2 Lpm. After 3 days fermentation, 10L of culture was used to inoculate a 780L fermenter containing 500L of medium SD1.

| SD1 | g/L |
|---|---|
| Meritose (Tunnel refineries) | 22 |
| Lactose | 20 |
| Glucidex 32D (Roquette Frere) | 30 |
| Arkasoy (The British Arkady Co.) | 20 |
| CSL | 20 |
| $FeCl_3.6H_2O$ | 0.05 |
| $NH_4H_2PO_4$ | 5 |
| $ZnSO_4.7H_2O$(BDH) | 0.1 |
| PPG2000 | 0.5 |
| Distilled water | |

The fermentation was controlled to a temperature of 25° C. The broth was agitated at 350 rpm and aerated at 200 Lpm. Distilled water was fed to maintain a culture volume of 500L. Whole broth extracts were assayed for presence of sordarin by reverse phase HPLC. The culture was harvested after 6 days when the extract of a broth sample indicated a sordarin titre of 1.3 g/L. A 50L sample of harvest broth was made 0.1M with respect to sodium hydroxide and stored at 4° C. overnight. Cells were removed by vacuum filtration through a bed of Dicalite adding an additional 2% Dicalite to the broth as filter aid. The filtrate was adjusted to approximately pH 6 with concentrated sulphuric acid. Broth extract was pumped through a bed of Amberchrom CG161 resin at 320 ml/min (0.64 bed volumes per min). The effluent was monitored by HPLC. After 45 min (equivalent to a pumped volume of 14.4L) sordarin began to break through and pumping was halted. The adsorbent was washed with water (2L) then 25% v/v acetone in water (2L). Sordarin was eluted with 75% v/v acetone in water (1.5L). The 75% v/v acetone eluate was evaporated to about 200 ml by rotary evaporation at 40° C. 200 ml butan-1-ol was added and the evaporation continued until a viscous oil remained (containing some butan-1-ol). The oily residue was extracted with hot methanol (2×500 ml). Extracts were combined, filtered (Whatman no 1 paper) then evaporated at 40 to 45° C. to give a viscous oil. This was extracted with hot acetone (2×500 ml). Acetone extracts were combined, filtered and evaporated to a viscous oil. Propan-2-ol (350 ml) was added and the oil dissolved at 45° C. to give a clear brown solution. A solution of potassium-2-ethylhexanoate (39% wow solution in propan-2-ol, 54 g) was weighed into a 500 ml conical flask. The sordarin-containing solution in propan-2-ol was poured into the conical flask, the contents mixed, and left to stand for 4h at room temperature. The solution was seeded with sordarin potassium salt (about 5 mg) and the stoppered flask was stored for 3 days at 4° C. The off-white solid which formed was filtered under vacuum (No 4 sinter funnel) and the filter cake was washed with propan-2-ol (about 20–30 ml). The solid was transferred to a crystallising dish and dried in vacuo over $P_2O_5$ for 16h to give the titled compound (10.5 g).

PREPARATION 3

Production of sordarin potassium salt 500 litres of culture broth was prepared as in Preparation 1. The broth was made 0.1M with respect to sodium hydroxide and after 4 days at 0° C. was filtered through a bed of Dicalite on a rotary vacuum filter. 1% Dicalite was added to the broth as filter aid. The pH of the filtrate was adjusted from pH 9.16 to pH 7.5 with concentrated sulphuric acid. Filtrate (10L) was adjusted to pH 6 with $H_3PO_4$ and applied to a bed (200 ml) of XAD-16 resin packed in water at a flow-rate of 1–1.5 bed volumes/h. The resin bed was washed with water (1 bed volume) then with 25% aqueous isopropanol (2.5 bed volumes) before elution with neat isopropanol. After a fore-run of 50 ml the isopropanol eluate was collected as 100 ml fractions. Sordarin-rich fractions 2–6 inclusive were pooled and evaporated to half volume. Isopropanol was added to bring the volume back to 500 ml, then the evaporation to half volume repeated to remove residual water by azeotropic distillation. After a third evaporation to half volume the residue was filtered and the filter was washed with isopropanol. To the combined filtrate and washings (400 ml) was added a solution of potassium 2-ethylhexanoate (8 g) in isopropanol (100 ml). The mixture was seeded with sordarin potassium salt and stood for several days at 4° C. whilst a slow crystallisation took place. Crystals were filtered on a No. 3 sinter, washed with a little ice-cold isopropanol and dried in vacuo to yield the title compound as a pale brown powder (4.85 g).

PREPARATION 4

Production of 4'-demethylsordarin (i) IMI 362184 was maintained in Brain Heart Infusion broth (Oxoid)+10% glycerol at −140° C. as described in Preparation 1. A suspension containing 2 agar plugs was used to inoculate a 250 ml Erlenmyer flash containing 50 ml of medium FS. The culture was incubated at 25° C. for 5 days on a rotary shaker operated at 250 rpm with a 5 mm diameter orbital motion. Aliquots (2 ml) of the developed inoculum were used to inoculate further 250 ml Erlenmyer flasks containing medium FS (50 ml) and incubated as described above. 80 ml of the bulked shake flask developed inoculum was used to inoculate each of two 7L fermenters containing 5L of medium FS. The fermentations were controlled to a temperature of 25° C. The culture was agitated at 400 rpm and aerated at 2 Lpm. After 3 days fermentation, 10L of culture was used to inoculate a 780L fermenter containing 500L of medium SM55VAR (as described in Preparation 1). The fermentation was controlled to a temperature of 25° C. The broth was agitated at 350 rpm and aerated at 500 Lpm. 70% w/v Meritose (Tunnel Refineries) solution was fed to the culture to maintain a positive residual glucose concentration. Distilled water was fed to maintain a culture volume of 500L. Whole broth extracts were assayed for presence of 4'-demethylsordarin by reverse phase HPLC. The culture was harvested after 10 days when the extract of a broth sample indicated a 4'-demethylsordarin titre of 0.8 g/L. Fermentation broth was made 0.1M with respect to sodium hydroxide and after 1 hour at ambient temperature was filtered through Dicalite on a rotary vacuum filter (1% Dicalite was added to the broth as filter aid). The filtrate was adjusted to pH 4.5 with concentrated sulphuric acid and the solution was applied to XAD16 resin (20 g product/L resin). The adsorbent was washed with 0.1% phosphoric acid (10 column volumes) and acetonitrile:water 1:4 (6 column volumes) before the product was eluted with acetonitrile::water (1:1; 2 column volumes). Flow rate throughout the process was between 1–2 column volumes/hr. The eluate was concentrated to dryness with the addition of butan-1-ol and the solid was extracted with methanol (12L) followed by acetone (10L) at 60° C. Insoluble material was removed at each stage by filtration through a no 3 glass sinter and the extracts concentrated to dryness as before. The solid was crystallised from acetonitrile:water (3:7) before being recrystallised from the same solvent and dried to constant weight over $P_2O_5$ to give the title compound (244.0 g), which by proton NMR analysis showed equivalence with an authentic sample of 4'-demethylsordarin.

(ii) The fermentation procedure in (i) above was followed, and after the broth was made 0.1M with respect to sodium hydroxide this was ultrafiltered through ETNA 10A membrane (10 kDalton cut-off). After diafiltration with water the bulked permeate was a clear solution. After adjustment to pH 5.2, using concentrated sulphuric acid, the permeate was loaded to a column of XAD16 resin at a rate of 2 column volumes per hour to give a final loading of 32 g 4'-demethylsordarin per litre of resin. The column was washed at a rate of 2 column volumes per hour, first with 0.1% v/v phosphoric acid and then with 20% v/v acetonitrile/water (10 column volumes of each). The column was eluted with 65% acetonitrile/water at 2 column volumes per hour. A forerun of 0.75 column volumes was discarded. 85% of the loaded 4'-demethylsordarin was recovered in the next 1.6 column volumes of eluate. The rich eluate was treated by stirring for 5 minutes with 2% w/v of DE52 cellulose, which was removed by filtration. An aliquot of DE52 treated eluate was concentrated to 62% of the original volume (43% acetonitrile) using a rotary evaporator. The concentrated eluate was held at 4° C. for 15 hours to crystallise and the solids formed collected by filtration through a glass sinter. The crystals were washed with four cake volumes of 30% v/v acetonitrile/water and dried at 30° C. in vacuo. The title compound (1.94 g) was recovered from the concentrated eluate as a pale grey solid.

PREPARATION 5

Screen for microorganisms capable of demethylating sordarin at the 4' position

Microorganisms capable of demethylating sordarin at the 4'-position could be identified by growing them at 28° C. (bacteria) or 25° C. (fungi) in 10 ml volumes of SB1 (bacteria) or FB1 (fungi) in 50 ml conical flasks shaken at 250 rpm. After 2 days, sordarin was added to a final concentration of 0.5 mg/ml (from a 200 mg/ml stock solution in 80% ethanol) and the flasks were then incubated for a further 3 days. A 500 $\mu$l sample of whole culture was mixed in an Eppendorf tube with 500 $\mu$l of 80% acetonitrile/2% trifluoroacetic acid and left to extract at room temperature for 30 minutes. The extract supernatant, obtained by centrifuging samples in a microfuge was assayed by isocratic HPLC for the presence of 4'-demethylsordarin. 4'-demethyl sordarin eluted at 3.35 mins with a mobile phase of 35% acetonitrile in water, flow rate 2 ml/min, using a Spherisorb $C_6$ column (5 $\mu$m, 15 cm ×4.6 mm). By this method, the following microorganisms were identified as sordarin demethylators:

| | |
|---|---|
| *Streptomyces capreolus* | ATCC 31963 |
| *Streptomyces avermitilis* | ATCC 31272 |
| *Streptomyces armentosus* | NRRL 3176 |
| *Streptomyces antibioticus* | ATCC 31771 |
| *Streptomyces rimosus* | ATCC 23955 |
| *Streptomcyes platensis* | ATCC 29778 |
| *Streptomyces mashuensis* | ATCC 23934 |
| *Streptomyces eurythermus* | ATCC 14975 |
| *Nocardia orientalis* | ATCC 43491 |
| *Cunninghamella echinulata* var *elegans* | ATCC 36112 |

| | g/L |
|---|---|
| SB1 Medium | |
| Arkasoy | 25 |
| Yeast extract | 5 |
| $KH_2PO_4$ | 5 |
| Glucose | 20 |
| Distilled Water | |
| pH 7 | |
| FB1 Medium | |
| Soya oil | 30 |
| Arkasoy | 10 |
| Yeast extract | 5 |
| $K_2HPO_4$ | 5 |
| Glucose | 20 |
| Distilled Water | |
| pH 5.5 | |

PREPARATION 6

Production of 4'-demethylsordarin by biotransformation of sordarin 0.3ml of a spore suspension of *Streptomyces capreolus* ATCC 31963 (in 15%, v/v glycerol stored at −20° C.) was inoculated into 30 ml SB1 medium in a 250 ml Erlenmeyer flask to give a seed culture which was incubated at 28° C. and 250 rpm on a rotary shaker. After 4 days, 0.5 ml of this was used to inoculator 35 ml SB1 in a 250 ml flask which was grown for 48 hours at 28° C., 250 rpm. At this stage, the culture was aliquoted as 10 ml amounts into 50 ml Erlenmeyer flasks which were fed with 5 mg sordarin (from a 200 mg/ml stock solution in ethanol). Incubation was continued for a further 3 days. 80% v/v acetonitrile in water (14 ml) was added to whole broth (14 ml) and the mixture was kept at room temperature and occasionally agitated. After 30 minutes, the cells were removed by centrifugation. Acetonitrile was removed by evaporation and the pH of the aqueous solution was adjusted to 2.5 with orthophosphoric acid. The solution was passed through a column containing Amberlite XAD-16 resin (bed volume 5 ml). The adsorbent was washed sequentially with water (10 ml), 10% v/v acetonitrile in water (20 ml), 30% v/v acetonitrile in water (10 ml), 50% v/v acetonitrile in water (20 ml) and 90% v/v acetonitrile in water (10 ml). Fractions were monitored by HPLC; 4'-demethylsordarin was located in the 50% v/v acetonitrile in water eluate. The fraction containing 4'-demethylsordarin was evaporated to dryness in vacuo at the room temperature and the residue was re-dissolved in 35% v/v acetonitrile in water (15 ml). 4'-demethylsordarin was purified by preparative HPLC:

| | |
|---|---|
| Column | Spherisorb 5 micron C6 25 cm × 2.5 cm |
| Flow rate | 25 ml/min |
| Detection | UV at 210 nm |
| Mobile Phase | 350 ml acetonitrile made up to 1000 ml with 0.05M ammonium dihydrogen phosphate in water. pH adjusted to 2.5 with orthophosphoric acid |
| Injection volume | 4.5 ml |

4'-Demethylsordarin was eluted after 10.0 minutes under these conditions. The pooled fractions from four HPLC runs were diluted 1:1 with water then pumped back onto the silica (after washing this with acetonitrile and re-equilibrating with water). The adsorbent was washed with water (200 ml) and adsorbed product was eluted with 95% v/v acetonitrile in water (200 ml). The acetonitrile/water eluate was evaporated to remove organic solvent, and the aqueous solution freeze dried to yield 4'-demethylsordarin (1.5 mg) as a white powder.

δ ($^1$H,CDCl$_3$); 9.74(s,1H); 6.08(brd,3,1H); 4.70(d,1.5,1H); 4.16(d,9.5,1H); 4.08(dd,4.5,3.5,1H); 3.88(dd,4.5,1.5,1H); 3.75(dq,8.5,6,1H); 3.62(d,9.5,1H); 3.68(dd,8.5,3.5,1H); 2.65(m,1H); 2.34(m,1H); 1.32(d,6,3H); 1.30(d,12.5,1H); 1.23(m,1H); 1.04(d,7,3H); 0.99(d,7,3H); 0.81(d,7,3H)

INTERMEDIATE 1

[1R-(1α,3aβ, 4β, 4aβ, 7β, 7aα, 8aβ)] 8a[(6-deoxy-4-O-methyl-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester A solution of sordarin (10.0 g) in dichloromethane (150 ml) was treated dropwise with a solution of diphenyldiazomethane in dichloromethane (0.35M, 85 ml). The resulting solution was stirred at room temperature for 24 hours. The solvent was removed under reduced pressure and the residue was purified by flash column chromatography on silica gel eluting with hexane:ethyl acetate (4:1) and (2:1). The fractions were combined and evaporated to yield the title compound (11.8 g) as a white foam.

δ ($^1$H, CDCl$_3$): 10.00 (s, 1H, CHO), 7.63 (m, 10H, 2Ph), 7.26 (s, 1H, CHPh$_2$), 6.30 (dd, 1H, H-2, J=1.2 and 3.3 Hz), 4.92 (d, 1H, H-1', J=0.9 Hz), 4.84 (t, 1H, H-3', J=3.3 Hz),4.03 and 4.35 (2d, 2H, 8aCH$_2$, J=9 Hz), 3.88 (m, 1H, H-2'), 3.70 (dq, 1H, H-5', J=6.3 and 9.3 Hz), 3.41 (s, 3H, 4'—OMe), 3.20 (dd, 1H, H4', J=3.3 and 9 Hz), 2.75 (t, 1H, H-1).

INTERMEDIATE 2

[1R-(1α, 3aβ, 4β, 4aβ, 7β, 7aα, 8aβ)] 8a-[(3-O-Benzyl-6-deoxy-4-O-methyl-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester A solution of Intermediate 1 (0.6 mmol) in dry tetrahydrofuran (15 ml) under nitrogen was treated with sodium hydride (1.5 mmol). After 30 minutes, a solution of benzyl bromide (0.7 mmol) in dry tetrahydrofuran (5 ml) was added. The mixture was stirred under reflux for 4.5 hours and then poured into water:ethyl acetate (1:1;100 ml). The organic phase was evaporated and the residue purified by flash chromatography using hexane:ethyl acetate (3:1) as eluent. Appropriate fractions were concentrated to give the title compound (249 mg).

δ ($^1$H, CDCl$_3$): 9.76 (s, 1H, CHO), 7.33 (m, 15H, 3×Ph), 6.99 (s, 1H, CHPh$_2$), 6.03 (dd, 1H, H-2, J=1.2 and 3.3 Hz), 4.84 and 4.64 (AB system, 1H, 1H, CHPh$_2$, J=12.6 Hz), 4.62 (d, 1H, H-1', J=1.2 Hz), 4.12 (m, 2H, H-3' and 8a-CHa), 3.66 (m, 3H, H-2', H-5' and 8a-CHb), 3.21 (dd, 1H, H4', J=3.3 and 9.3 Hz), 2.70 (t, 1H, H-1, J=3.9 Hz), 2.92 (d, 1H, OH, J=9.9 Hz), 2.21 (m, 1H, CH(CH$_3$)$_2$).

INTERMEDIATE 3

[1R-(1α, 3aβ, 4β, 4aβ, 7β, 7aα, 8aβ)] 8a-[(6-Deoxy-3-O-hexyl-4-O-methyl-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester A solution of Intermediate 1 (0.6 mmol) in dry tetrahydrofuran (15 ml) under nitrogen was treated with sodium hydride (1.5 mmol). After 30 minutes, a solution of hexyl iodide (0.7 mmol) in dry tetrahydrofuran (5 ml) was added. The mixture was stirred under reflux for 36 hours and then poured into water:ethyl acetate (1:1;100 ml). The organic phase was evaporated and the residue purified by flash chromatography using hexane:ethyl acetate (2:1) as eluent to give the title compound (124 mg).

δ ($^1$H, CDCl$_3$): 10.01 (s, 1H, CHO), 7.60 (m, 10H, 2×Ph), 7.26 (s, 1H, CH-Ph$_2$), 6.31 (dd, 1H, H-2, J=1.5 and 3.3 Hz), 4.87 (s, 1H, H-1', J=1.2 Hz), 4.40 (t, 1H, H-3', J=3.3 Hz), 4.35 and 3.94 (d,d, 1H, 1H, 8a-CH$_2$, J=9 Hz), 4.04 (m, 2H, H-2' and H-5'), 3.80 (m, 2H, OCH$_2$CH$_2$), 3.44 (dd, 1H, H-4', J=3.3 and 9 Hz), 3.01 (t, 1H, H-1, J=3.6 Hz).

INTERMEDIATE 4

[1R-(1α, 3aβ, 4β, 4aβ, 7β, 7aα, 8aβ)] 8a-[(6-Deoxy-2,3,4-tri-O-methyl-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester A solution of Intermediate 1 (0.6 mmol) in dry tetrahydrofuran (20 ml) under nitrogen was treated with sodium hydride (1.5 mmol). After 30 minutes, methyl iodide (112 μl) was added. The mixture was stirred at room temperature for 4 hours and poured into ethyl acetate:water (1:1;100 ml). The organic phase was evaporated and the residue purified by flash chromatography using hexane:ethyl acetate (3:1) as eluent. Appropriate fractions were concentrated to give the title compound (195 mg).

δ ($^1$H, CDCl$_3$): 9.77 (s, 1H, CHO), 7.37 (m, 10H, 2×Ph), 6.99 (s, 1H, CHPh$_2$), 6.05 (dd, 1H, H-2, J=1.5 and 3.6 Hz), 4.55 (d, 1H, H-1', J=0.9 Hz), 4.07 and 3.69 (d,d, 1H, 1H, 8a-CH$_2$, J=8.7 Hz), 3.71 (m, 2H, H-2' and H-3'), 3.43 (dd, 1H, H-5', J=0.6 and 3.9 Hz), 3.57 (s, 3H, 2'—OCH$_3$), 3.51 (s, 3H, 3'—OCH$_3$), 3.16 (dd, 1H, H4', J=3 and 9.3 Hz), 2.75 (t,1H, H-1, J=3.9 Hz).

INTERMEDIATE 5

[1R-(1α, 3aβ, 4β, 4aβ, 7β, 7aα, 8aβ)] 8a-[(6-Deoxy-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester To a solution of 4'-demethylsordarin (10 g) in methanol (20 ml) was added dropwise at room temperature a solution of diphenyldiazomethane (90 ml) in methylene chloride, and the mixture was stirred for 6 hours. The solvent was evaporated to dryness and the residue chromatographed in a silica gel flash column with n-hexane:ethyl acetate (3:1) as eluent to give the title compound (12.6 g) as a pale yellow foam.

δ ($^1$H, CDCl$_3$): 9.73 (s, 1H, CHO), 6.98 (s, 1H, CHPh$_2$), 6.05 (dd, 1H, H-2, J=1.5 and 3.6 Hz), 4.65 (d, 1H, H-1', J=1.5 Hz), 4.09, 3.76 (2d, 2H, 8a-CH$_2$, J=9 Hz), 4.01 (m, 1H, H-2'), 3.84 (m, 1H, H-3'), 3.75 (m, 1H, H-5'), 3.69 (m, 1H, H-4'), 2.73 (t, 1H, H-1, J-4.2 Hz).

INTERMEDIATE 6

[1R-(1α, 3aβ, 4β, 4aβ, 7β, 7aα, 8aβ)] 8a-[(6-Deoxy-3,4-O-isopropylidene-β-D-altropyranosyloxy)methyl]-4-formyl-4,4a,5,6,7,7a,8,8a-octahydro-7-methyl-3-(1-methylethyl)-(1H)-1,4-methano-s-indacene-3a(1H)-carboxylic acid, diphenylmethyl ester To a solution of Intermediate 5 (650 mg) in 15 ml of 2,2-dimethoxypropane:acetone (1:2) was added p-toluensulphonic acid (10 mg). The solution was stirred at room temperature for 1.5 hours, then potassium carbonate (1.0 g) was added, the stirring continued for 30 minutes and the solvent evaporated to dryness. The crude mixture was partitioned between ethyl acetate (50 ml) and water (25 ml), the aqueous phase was extracted with ethyl acetate (2×50 ml), the organic phase was washed with brine, dried over magnesium sulphate and evaporated to dryness. The residue was flash chromatographed on silica gel eluting with ethyl acetate:hexane (1:3) to give the title compound (600 mg) as a white foam.

δ ($^1$H, CDCl$_3$): 9.73 (s, 1H, CHO), 7.45-7.24 (m, 10H, 2Ph), 6.98 (s, 1H, CHPh$_2$), 6.06 (dd, 1H, H-2, J=1.5 and 3.3 Hz), 4.57 (d, 1H, H-1', J=3.0 Hz), 4.30 (dd, 1H, H-3', J=3.6 and 5.7 Hz), 4.07 (d, 1H, 8aCH$_2$, J=9.0 Hz), 3.95-3.93 (m, 1H, H-2'), 3.85 (dd, 1H, H4', J=5.7 and 9.3 Hz), 3.75 (d, 1H, 8aCH$_2$, J=9.0 Hz), 3.44 (dq, 1H, H-5', J$_d$=9.3 Hz, J$_q$=6.3 Hz), 2.73 (t, 1H, H-1, J=3.6 Hz).

INTERMEDIATE 7

[1R-(1α, 3aβ, 4β, 4aβ, 7β, 7aα, 8aβ)] 8a-[(6-Deoxy-3,4-O-isopropylidene-2-O-(methylthio)thiocarbonyl-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester Intermediate 6 (100 mg) and imidazole (1 mg) were dissolved in dry tetrahydrofuran (4 ml) under nitrogen atmosphere. Sodium hydride (5 mg) was added and the suspension was stirred at room temperature for 0.5 hours Carbon disulfide (2.7 ml) was added, the stirring continued for 20 minutes and methyl iodide (18 ml) was added. After 2 hours the reaction was stopped by addition of 1N ammonium chloride (20 ml). The mixture was extracted with ethyl acetate (3×25 ml), the organic phase was washed with brine, dried over magnesium sulphate and the solvent evaporated to dryness. The residue was purified in a flash chromatography column on silica gel eluting with ethyl acetate:hexane (1:9) to give the title compound (110 mg).

δ ($^1$H, CDCl$_3$): 9.71 (s, 1H, CHO), 7.44-7.25 (m, 10H, 2Ph), 6.96 (s, 1H, CHPh$_2$), 6.01 (dd, 1H, H-2, J=1.2 and 3.6 Hz), 6.90 (dd, 1H, H-2', J-2.4 and 5.4 Hz), 4.85 (d, 1H, H-1', J=2.4 Hz), 4.53 (dd, 1H, H-3', J=5.4 and 6.3 Hz), 4.00 (dd, 1H, H-4', J=6.3 and 8.7 Hz), 3.93 (d, 1H, 8aCH$_2$, J=9.3 Hz), 3.65 (dq, 1H, H-5', J$_d$=8.7, J$_q$=6.3 Hz), 2.68 (t, $_1$H, H-1, J=3.9 Hz), 2.59 (s, 3H, CH$_3$S).

INTERMEDIATE 8

[1R-(1α, 3aβ, 4β, 4aβ, 7β, 7aα, 8aβ)] 8a-[(2,6-Dideoxy-3,4-O-isopropylidene-β-D-allopyranosyloxy)methyl]-formyl-4,4a,5,6,7,7a,8,8a-octahydro-7-methyl-3-(1-methylethyl)-1,4-methano-s-indacene-3a(1H)-carboxylic acid, diphenylmethyl ester Intermediate 7 (95 mg) was dissolved in dry toluene (5 ml) under nitrogen atmosphere and heated at 110° C. A solution of tributyltin hydride (64 ml) in dry toluene (5 ml) was added dropwise over 1.5 hours with stirring. The heating was continued for another 1.5 hours, methanol (2 ml) was added and the solvent evaporated to dryness. Flash chromatography of the residue on silica gel eluting with ethyl acetate:hexane (1:9) gave the title compound (42 mg).

δ ($^1$H, CDCl$_3$): 9.73 (s, 1H, CHO), 7.44-7.25 (m, 10H, 2Ph), 6.98 (1H, s, CHPh$_2$), 6.05 (dd, 1H, H-2, J=1.2 and 3.3 Hz), 4.54 (dd, 1H, H-1', J=2.7 and 9.3 Hz), 4.39 (dt, 1H, H-3', J$_d$=2.7 Hz, J$_t$=3.6 Hz), 4.04 (d, 1H, 8aCH$_2$, J=9.0 Hz), 3.67 (d, 1H, 8aCH$_2$, J=9.0 Hz), 3.65 (dd, 1H, H4', J=3.6 and 8.7 Hz), 3.44 (dq, 1H, H-5', J$_d$=6.3 Hz, J$_q$=8.7 Hz), 2.75 (t, 1H, J=3.9 Hz).

INTERMEDIATE 9

[1R-(1α, 3aβ, 4β, 4aβ, 7β, 7aα, 8aβ)] 8a-[(2,6-Dideoxy-β-D-allopyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester To a solution of Intermediate 8 (1.5 g) in a mixture of tetrahydrofuran (30 ml) and methanol (15 ml) was added dropwise at room temperature a 1N solution of hydrochloric acid (15 ml) with vigorous stirring. Once the reaction was concluded (TLC control), saturated sodium bicarbonate (50 ml) and ethyl acetate (200 ml) were added and the mixture partitioned. The organic layer was washed with water (2×100 ml) and dried over magnesium sulfate. Elimination of the solvent gave a residue which was flash chromatographed over silica gel eluting with hexane:ethyl acetate (5:1) and (2:1) to give the title compound (1.1 g) as a white foam.

δ ($^1$H, CDCl$_3$): 9.73 (s, 1H, CHO), 7.5-7.2 (m, 10H, 2Ph), 6.99 (s, 1H, CHPh$_2$), 6.05 (dd, 1H, H-2, J=1.2 and 3.3 Hz), 4.64 (dd, 1H, H-1', J=2.1 and 9.6 Hz), 4.11 (m, 1H, H-3'), 4.06 (d, 1H, 8aCH$_2$, J$_{AB}$=9.3 Hz), 3.70 (m, 2H, H-5' and 8aCH$_2$), 3.34 (m, 1H, H-4'), 2.75 (t, 1H, H-1, J=3.6 Hz).

INTERMEDIATE 10

[1R-(1α, 3aβ, 4β, 4aβ, 7β, 7aα, 8aβ)] 8a-[(2,6-Dideoxy-4-O-methyl-β-D-allopyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester A suspension of Intermediate 9 (380 mg) and dibutyltin oxide (225 mg) in dry toluene (15 ml) was refluxed for 2 hours in a flask fitted with a Dean Stark condenser, under nitrogen. The mixture was allowed to stand at room temperature and methyl iodide (200 μl) and a 1M solution of tetrabutylammonium fluoride in tetrahydrofuran (3 ml, 3 mmol) were added consecutively in several portions. The mixture was heated at 40° C. for 24 hours, under nitrogen. The solvent was then evaporated in vacuo and the residue purified by silica gel flash chromatography eluting with hexane:acetone (10:1) to afford the title compound (220 mg)

together with the corresponding 3-O-methyl compound which eluted with a lower Rf.

δ ($^1$H, CDCl$_3$): 9.72 (s, 1H, CHO), 7.32 (m, 10H, 2Ph), 6.98 (s, 1H, CHPh2), 6.05 (dd, 1H, H-2, J=1.5 and 3.6 Hz), 4.64 (dd, 1H, H-1', J-1.8 and 9.6 Hz), 4.25 (q, 1H, H-3', J=3.3 Hz), 4.52 and 3.67 (2d, 2H, 8a-CH$_2$, J=9.3 Hz), 3.69 (m, 1H, H-5'), 3.41 (s, 3H, OCH$_3$), 2.87 (dd, 1H, H4', J=3.3 and 9.3 Hz), 2.75 (t, 1H, H-1).

INTERMEDIATE 11

[1R-(1α, 3aβ, 4β, 4aβ, 7β, 7aα, 8aβ)] 8a-[(2,6-Dideoxy-4-O-methyl-3-O-methyloxymethyl-β-D-allopyranosyloxy) methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester To a solution of Intermediate 10 (200 mg) in diisopropylethylamine (4 ml) at 0° C. under nitrogen was added a large excess of methyloxymethyl chloride (0.2 to 1 ml). The mixture was stirred for 1 hour at 0° C. and 24 hours at room temperature. The reaction was quenched with the addition of methanol, 10% sodium bicarbonate and hydrochloric acid, and stirring was continued for 2 hours. Water (50 ml) and ethyl acetate (50 ml) were added and the organic layer was separated and dried over magnesium sulphate. Removal of the solvent gave the title compound (200 mg).

δ ($^1$H, CDCO$_3$): 9.74 (s, 1H, CHO), 6.98 (s, 1H, CHPh$_2$), 6.04 (dd, 1H, H-2, J=1.5 and 3.6 Hz), 4.74 (AB system, 2H, OCH$_2$OCH$_3$, J=6.6 Hz), 4.61 (dd, 1H, H-1', J=2.1 and 9.3 Hz), 4.20 (m, 1H, H-3'), 4.04 and 3.69 (2d, 2H, 8a-CH$_2$, J=9.6 Hz), 3.81 (m, 1H, H-5'), 3.41 (s, 3H, OCH$_3$), 3.40 (s, 3H, OCH$_3$), 2.88 (dd, 1H, H-4', J=3 and 9.6 Hz), 2.75 (t, 1H, H-11, J=3.9 Hz).

INTERMEDIATE 12

[1R-(1α, 3aβ, 4β, 4aβ, 7β, 7aα, 8aβ)] 8a-[(6-Deoxy-4-O-methyl-β-D-altropyranosyloxy)methyl]-4-(1,3-dioxolan-2-yl)-4,4a,5,6,7,7a,8,8a-octahydro-7-methyl-3-(1-methylethyl)-1,4-methano-s-indacene-3a(1H)-carboxylic acid, diphenylmethyl ester A solution of Intermediate 1 (9.7 mmol) in dry methanol (40 ml) was treated with ethylene glycol (110 ml), trimethylorthoformate (3.25 ml) and a catalytic amount of p-toluenesulfonic acid. The mixture was heated at 40° C. for 3 hours. After cooling, the mixture was poured into ethyl acetate:aqueous sodium hydrogen carbonate (1:1; 500 ml) and the water layer was thoroughly extracted with ethyl acetate. The combined organic layers were washed with water and brine, and dried. After removal of the solvent, the residue was purified by flash chromatography using hexane:ethyl acetate (6:1) as eluent to give the title compound (6.1 g).

δ ($^1$H, CDCl$_3$): 7.43 and 7.30 (m,m, 4H, 6H, 2×Ph), 6.94 (s, 1H, CHPh$_2$), 5.83 (dd, 1H, H-2, J=1.2 and 3.6 Hz), 5.07 (s, 1H, 4-CH), 4.63 (d, 1H, H-1', J=1.5 Hz), 4.20 (t, 1H, H-3', J=3.3 Hz), 4.07 (d, 1H, 8a-CHa, J=9.3 Hz), 3.84 (m, 6H, H-2', 8a-CHb and OCH$_2$CH$_2$O), 3.71 (m, 1H, H-5'), 3.42 (s, 3H, OCH$_3$), 3.21 (dd, 1H, H4', J=3 and 9 Hz), 2.63 (m, 1H, CH(CH$_3$)$_2$), 2.54 (t, 1H, H-1, J=3.9 Hz).

INTERMEDIATE 13

[1R-(1α, 3aβ, 4β, 4aβ, 7β, 7aα, 8aβ)] 8a-[[6-Deoxy-4-O-methyl-2,3-di-O-(p-tolylsulfonyl)-β-D-altropyranosyloxy] methyl]-4-(1,3-dioxolan-2-yl)-4,4a,5,6,7,7a8,8a-octahydro-7-methyl-3-(1-methylethyl)-1,4-methano-s-indacene-3a (1H)-carboxylic acid, diphenylmethyl ester To a solution of Intermediate 12 (3.88 mmol) and 4-dimethylaminopyridine (9 mmol) in dry dichloromethane (15 ml) was added dropwise a solution of p-toluenesulfonyl chloride (8 mmol) in dry dichloromethane (15 ml). After stirring for one day, the mixture was washed with water and the organic layer was evaporated. The residue was purified by flash chromatography using hexane:ethyl acetate (4:1) as eluent. Appropriate fractions were combined and evaporated to dryness to give the title compound (3.1 g).

δ ($^1$H, CDCl$_3$): 7.88 and 7.30 (m,m, 4H, 14H, Ar), 6.90 (s, 1H, CHPh$_2$), 5.64 (dd, 1H, H-2, J=1.2 and 3.6 Hz), 5.01 (s, 1H, 4-CH), 4.98 (dd, 1H, H-3', J=3 and 4.2 Hz), 4.59 (m, 2H, H-1' and H-2'), 3.94 and 3.53 (d,d, 1H, 1H, 8a-CH$_2$, J=9 Hz), 3.82 (m, 4H, OCH$_2$CH$_2$O), 3.68 (m, 1H, H-5'), 3.18 (dd, 1H, H4', J=3 and 9 Hz), 2.83 (s, 3H, OCH$_3$), 2.55 (m, 1H, CH(CH$_3$)$_2$), 2.48 and 2.45 (s,s, 3H, 3H, 2×CH$_3$Ar).

INTERMEDIATE 14

[1R-(1α, 3aβ, 4β, 4aβ, 7β, 7aα, 8aβ)] 8a-[(2,3-Anhydro-6-deoxy-4-O-methyl-β-D-allopyranosyloxy)methyl]-4-(1,3-dioxolan-2-yl)-4,4a,5,6,7,7a,8,8a-octahydro-7-methyl-3-(1-methylethyl)-1,4-methano-s-indacene-3a(1H)-carboxylic acid, diphenylmethyl ester A solution of Intermediate 13 (2.87 mmol) in dry dichloromethane (20 ml), under nitrogen atmosphere at 0° C., was treated with a solution of sodium methoxide (20 mmol) in methanol (20 ml). After three days the solvent was evaporated to dryness and the residue was dissolved in dichloromethane:water (1:1; 100 ml). The organic layer was evaporated and the residue purified by flash chromatography using hexane:ethyl acetate (7:1) as eluent. Appropriate fractions eluting with the higher Rf were combined and evaporated to give the title compound (680 mg).

δ ($^1$H, CDCl$_3$): 7.44 and 7.29 (m,m, 4H, 6H, 2×Ph), 6.93 (s, 1H, CHPh$_2$), 5.86 (dd, 1H, H-2, J=0.9 and 3.3 Hz), 5.08 (s, 1H, 4-CH), 4.59 (s, 1H, H-1'), 4.03 (d, 1H, 8a-CHa, J=9 Hz), 3.83 (m, 5H, 8a-CHb and OCH$_2$CH$_2$O), 3.49 (m, 4H, H4' and OCH$_3$), 3.33 (m, 3H, H-2', H-3' and H-5'), 2.64 (m, 1H, CH(CH$_3$)$_2$), 2.58 (t, 1H, H-1, J=3.9 Hz).

INTERMEDIATE 15

[1R-(1α, 3aβ, 4β, 4aβ, 7β, 7aα, 8aβ)] 8a-[(2,3-Anhydro-6-deoxy-4-O-methyl-β-D-mannopyranosyloxy)methyl]-4-(1, 3-dioxolan-2-yl)-4,4a,5,6,7,7a,8,8a-octahydro-7-methyl-3-(1-methylethyl)-1,4-methano-s-indacene-3a(1H)-carboxylic acid diphenylmethyl ester Appropriate fraction from the Intermediate 14 preparation eluting at the lower, Rf were combined and evaporated to give the title compound (912 mg).

δ ($^1$H, CDCl$_3$): 7.43 and 7.29 (m, m, 4H, 6H, 2×Ph), 6.95 (s, 1H, CHPh$_2$), 5.86 (dd, 1H, H-2, J=1.2 and 3.6 Hz), 5.07 (s, 1H, 4-CH),4.66 (s, 1H, H-1'), 4.11 (d, 1H, 8a-CHa, J=9.3 Hz), 3.82 (m, 5H, 8a-CHb and OCH$_2$CH$_2$O), 3.49 (s, 3H, OCH$_3$), 3.24 (d, 1H, H-2', J=3.9 Hz), 3.16 (m, 1H, H-5'), 3.12 (m, 2H, H-3' and H-4'), 2.62 (m, 2H, H-1 and CH(CH$_3$)$_2$).

INTERMEDIATE 16

[1R-(1α, 3aβ, 4β, 4aβ, 7β, 7aα, 8aβ)] 8a-[(3-Azido-3,6-dideoxy-4-O-methyl-β-D-altropyranosyloxy)methyl]-4-(1, 3-dioxolan-2-yl)-4,4a,5,6,7,7a,8,8a-octahydro-7-methyl-3-(1-methylethyl)-1,4-methano-s-indacene-3a(1H)-carboxylic acid, diphenylmethyl ester A solution of Intermediate 15 (0.7 mmol) and lithium azide (2.9 mmol) in dry dimethylformamide (10 ml) was heated for 45 hours at 100° C. After cooling, the mixture was poured into ethyl acetate:water (1:1;100 ml) and the organic phase was evaporated. The residue was purified by flash chromatography using hexane:ethyl acetate (4:1) as eluent. Appropriate fractions were combined and concentrated to give the title compound (359 mg).

(¹H, CDCl₃): 7.43 and 7.30 (m,m, 4H, 6H, 2×Ph),6.93 (s, 1H, CHPh₂), 5.83 (dd, 1H, H-2, J=1.5 and 3.6 Hz), 5.07 (s, 1H, 4-CH), 4.50 (d, 1H, H-1', J=1.5 Hz), 4.14 (m, 1H, H-2'), 4.03 (d, 1H, 8a-CHa), 3.79 (m, 7H, H-3', H-5', 8a-CHb and OCH₂CH₂O), 3.45 (s, 3H, OCH₃), 3.36 (dd, 1H, H4', J=3.3 and 8.1 Hz), 2.64 (m, 1H, CH(CH₃)₂), 2.49 (t, 1H, H-1, J=4.2 Hz), 2.36 (d, 1H, 2'—OH, J=3.3 Hz).

INTERMEDIATE 17

[1R-(1α, 3aβ, 4β, 4aβ, 7β, 7aα, 8aβ)] 8a-[(3,6-Dideoxy-4-O-methyl-3-methylthio-β-D-altropyranosyloxy)methyl]-4-(1,3-dioxolan-2-yl)-4,4a,5,6,7,7a,8,8a-octahydro-7-methyl-3-(1-methylethyl)-1,4-methano-s-indacene-3a(1H)-carboxylic acid, diphenylmethyl ester A mixture of Intermediate 15 (0.58 mmol) and sodium thiomethoxide (3 mmol) in dry dimethylformamide (5 ml) was stirred for 48 hours and then poured into ethyl acetate:water (1:1;100 ml). The organic phase was evaporated and the residue purified by flash chromatography using hexane:ethyl acetate (4:1) as eluent. Appropriate fractions were combined and evaporated to give a mixture which was dissolved in dry dichloromethane (10 ml) and treated with 4-dimethylaminopyridine (0.7 mmol). After stirring for 20 minutes at −20° C. under nitrogen atmosphere, trichloroethoxycarbonyl chloride (0.35 mmol) was added. After 90 minutes, the mixture was washed with water, the organic phase was evaporated and the residue was purified by flash chromatography using hexane:ethyl acetate (4:1) as eluent to give a solid which was dissolved in tetrahydrofuran (10 ml) and treated with 1M aqueous potassium phosphate (0.3 ml) and zinc (4.6 mmol). The mixture was stirred overnight at room temperature, filtrated and washed with water. The organic phase was evaporated and the residue purified by flash chromatography using hexane:ethyl acetate (5:1) as eluent to give the title compound (40 mg).

δ (¹H, CDCl₃): 7.44 and 7.30 (m, m, 4H and 6H, 2×Ph), 6.94 (s, 1H, CHPh₂), 5.85 (dd, 1H, H-2, J=0.9 and 3.3 Hz), 5.07 (s, 1H, 4-CH), 4.69 (d, 1H, H-1', J=1.5 Hz), 4.04 (d, 1H, 8a-CHa, J=9Hz), 3.94 (m, 1H, H-2'), 3.82 (m, 5H, 8a-CHb and OCH₂CH₂O), 3.73 (m, 1H, H-5'), 3.47 (dd, 1H, H-4', J=4.2 and 8.4 Hz), 3.40 (s, 3H, OCH₃), 3.33 (t, 1H, H-3', J=4.2 Hz), 2.63 (m, 1H, CH(CH₃)₂), 2.52 (t,1 H, H-1, J=4.2 Hz), 2.44 (d,1H, 2'—OH, J=3.6 Hz), 2.23 (s, 3H, SCH₃).

INTERMEDIATE 18

[1R-(1α, 3aβ, 4β, 4aβ, 7β, 7aα, 8aβ)] 8a-[(3-Azido-3,6-dideoxy-4-O-methyl-β-D-glucopyranosyloxy)methyl]-4-(1,3-dioxolan-2-yl)-4,4a,5,6,7,7a,8,8a-octahydro-7-methyl-3-(1-methylethyl)-1,4-methano-s-indacene-3a(1H)-carboxylic acid, diphenylmethyl ester A solution of Intermediate 14 (0.2 mmol) and lithium azide (0.7 mmol) in dry dimethylformamide (5 ml) was heated for 48 hours at 100° C. After cooling, the mixture was poured into ethyl acetate:water. (1:1;50 ml). The organic phase was evaporated and the residue purified by flash chromatography using hexane:ethyl acetate (3:1) as eluent. Appropriate fractions were combined and concentrated to give the title compound (71 mg).

δ (¹H, CDCl₃): 7.31 (m, 10H, 2×Ph), 6.92 (s, 1H, CHPh₂), 5.84 (dd, 1H, H-2, J=1.2 and 3.3 Hz), 5.08 (s, 1H, 4-CH), 4.04 (m, 2H, H-1' and 8a-CHa), 3.84 (m, 5H, 8a-CHb and OCH₂CH₂O), 3.32 (m, 3H, H-2', H-3' and H-5'), 2.74 (t, 1H, H-4', J=9 Hz), 2.66 (m, 1H, CH(CH₃)₂), 2.54 (t 1H, H-1, J=3.6 Hz), 2.30 (d, 1H, 2'—OH, J=1.8 Hz).

INTERMEDIATE 19

[1R-(1α, 3aβ, 4β, 4aβ, 7β, 7aα, 8aβ)] 8a-[(3,6-Dideoxy-4-O-methyl-3-methylthio-β-D-glucopyranosyloxy)methyl]-4-(1,3-dioxolan-2-yl)-4,4a,5,6,7,7a,8,8a-octahydro-7-methyl-3-(1-methylethyl)-1,4-methano-s-indacene-3a(1H)-carboxylic acid, diphenylmethyl ester A solution of Intermediate 14 (0.3 mmol) and sodium thiomethoxide (1 mmol) in dry dimethylformamide (5 ml) was stirred for 26 hours and then poured into ethyl acetate:water (1:1;100 ml). The organic phase was evaporated and the residue purified by flash chromatography using hexane:ethyl acetate (4:1) as eluent to give the title compound (134 mg).

δ (¹H, CDCl₃): 7,33 (m,10H, 2×Ph), 6.93 (s, 1H, CHPh₂), 5.86 (dd, 1H, H-2, J=1.2 and 3.6 Hz), 5.08 (s, 1H, 4-CH), 4.10 (m, 2H, H-1', and 8a-CHa), 3.84 (m, 5H, 8a-CHb and OCH₂CH₂O), 3.60 (s, 3H, OCH₃), 3.30 (m, 3H, H-2', H-3' and H-5'), 2.80 (m, 1H, H-4'), 2.65 (m, 2H, H-1 and CH(CH₃)₂), 2.21 (s, 3H, SCH₃).

INTERMEDIATE 20

[1R-(1α, 3aβ, 4β, 4aβ, 7β, 7aα, 8aβ)] 8a-[(2-O-Acetyl-3-acetylamino-3,6-dideoxy-4-O-methyl-β-D-glucopyranosyloxy)methyl]-4-formyl-4,4a,5,6,7,7a,8,8a-octahydro-7-methyl-3-(1-methylethyl)-1,4-methano-s-indacene-3a(1H)-carboxylic acid To a mixture of Intermediate 18 (0.4 mmol) in methanol (40 ml) and 1N hydrochloric acid (10 ml) was added 10% palladium on charcoal (70 mg) under nitrogen. The mixture was shaken in a Parr apparatus under 20 psi of hydrogen for 2 hours at room temperature. The catalyst was filtered off and the solvent evaporated to dryness. The residue was dissolved in dichloromethane (5 ml) and treated with pyridine (3 ml) and acetic anhydride (0.6 mmol). The mixture was heated for 48 hours at 40° C. and then cooled and washed with water. The organic phase was evaporated and the residue purified by flash chromatography using dichloromethane:methanol (20:1) as eluent to give the title compound (167 mg).

δ (¹H, CDCl₃): 9.73 (s, 1H, CHO), 6.00 (dd, 1H, H-2, J=1.2 and 3.3 Hz), 5.55 (d, 1H, NH, J=9.3 Hz), 4.66 (dd, 1H, H-2', J=7.8 and 10.5 Hz), 4.28 (m, 2H, H-1' and H-3'), 4.06 and 3.54 (d,d, 1H, 1H, 8a-CH₂, J=9.6 Hz), 3.49 (m, 4H, OCH₃ and H-5'), 2.82 (t, 1H, H4', J=9.6 Hz), 2.58 (t, 1H, H-1, J=4.2 Hz), 2.32 (m, 1H, CH(CH₃)₂), 2.01 and 1.99 (s,s, 3H, 3H, 2×CH₃CO).

INTERMEDIATE 21

[1R(1α, 3aβ, 4β, 4aβ, 7β, 7aβ, 8aβ)] 8a-[(2,3,6-Trideoxy-3-iodo-β-D-glucopyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester Intermediate 9 (2.0 g), triphenylphosphine (3.4 g) and imidazole (186 mg) were refluxed in toluene (50 ml) with stirring and then treated with iodine (610 mg), added in small portions. Refluxing was continued for 4 hours. The reaction mixture was cooled, decanted into excess aqueous sodium hydrogen carbonate and sodium thiosulfate in a separating funnel. The mixture was shaken until the iodine was consumed. The toluene phase was washed with water, dried over magnesium sulfate and concentrated. The residue was purified by flash column chromatography eluting with hexane:ethyl acetate (15:1) and (5:1) to give the title compound (1.65 g).

δ (¹H, CDCl₃): 9.73 (s, 1H, CHO), 7.26–7.44 (m, 10H, 2Ph), 6.98 (s, 1H, CHPh₂), 6.04 (dd, 1H, H-2, J-1.2 and 3.3 Hz), 4.25 (dd, 1H, H-1', J=1.8 and 9.3 Hz), 4.08 (m, 1H, H-4'), 3.67 and 4.01 (2d, 2H, 8aCH₂, J=9 Hz), 3.40 (m, 1 H, H-3'), 3.32 (m 1H, H-5'), 2.74 (t, 1H, H-1, J=4.2 Hz), 2.32 and 2.53 (2m, 2H, 2H-240 ).

INTERMEDIATE 22

[1R-(1α, 3aβ, 4β, 4aβ, 7β, 7aα, 8aβ)]-[(3-Azido-2,3,6-trideoxy-β-D-allopyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester A stirred solution of Intermediate 21 (300 mg) in dry dimethylformamide was treated with lithium azide (60 mg). The reaction mixture was heated at 70° C. for 18 hours. The solvent was removed under reduce pressure and the residue was purified by flash column chromatography eluting with hexane:ethyl acetate (4:1) to afford the title compound (246 mg) as a pale yellow syrup.

δ ($^1$H, CDCl$_3$): 9.74 (s, 1H, CHO), 7.25–7.45 (m, 10H, 2Ph$_2$), 6.97 (s, 1H, CHPh$_2$), 6.07 (dd, 1H, H-2, J=1.5 and 3.6 Hz), 4.52 (dd, 1H, H-1', J=1.4 and 9.3 Hz), 4.07 (q, 1H, H-3', J=3.6 Hz), 3.68 and 4.02 (2d, 2H, 8aCH$_2$, J=9.3 Hz), 3.59 (dq, 1H, H-5', J=6.3 and 9 Hz), 3.40 (dd, 1H, H4', J=3.6 and 9 Hz), 2.74 (t, 1H, H-1, J=3.6 Hz), 2.06–2.12 and 1.73–4.82 (2m, 2H, 2H-2').

INTERMEDIATE 23

[1R-(1α, 3aβ, 4β, 4aβ, 7β, 7aα, 8aβ)] 8a-[(3-Azido-4-Azido-4-O-methyl-2,3,6-trideoxy-β-D-allopyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester To a stirred solution of Intermediate 22 (140 mg) in dry tetrahydrofuran (10 ml) at 0° C. was added sodium hydride (97%, 6 mg). The mixture was stirred for 30 minutes under nitrogen, before methyl iodide (0.7 ml) was added. Stirring was continued for a further 5 hours at which time the reaction was quenched with methanol (3 ml). The solvent was evaporated to dryness under reduce pressure and the residue was purified by flash column chromatography eluting with hexane:ethyl acetate (6:1) to afford the title compound (56 mg).

δ ($^1$H, CDCl$_3$): 9.73 (s, 1H, CHO), 7.44-7.26 (m, 10H, 2Ph), 6.98 (s, 1H, CHPh$_2$), 6.06 (dd, 1H, H-2, J=1.5 and 3.6 Hz), 4.50 (dd, 1H, H-1', J=2.1 and 9.3 Hz), 4.22 (m, 1H, H-3'), 3.67 and 4.03 (2d, 2H, 8aCH$_2$, J=9.3 Hz), 3.76 (dq, 1H, H-5', J=6 Hz and 9 Hz), 3.44 (s, 3H, 4'—OMe), 3.01 (dd,1H, H-4', J=3.3 and 9 Hz).

INTERMEDIATE 24

[1R-(1α, 3aβ, 4β, 4aβ, 7β, 7aα, 8aβ)] 8a-[(2-O-Benzyloxycarbonyl-6-deoxy-4-O-methyl-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester To a solution of Intermediate 1 (3 mmol) in dry dichloromethane (15 ml) at 0° C. under nitrogen atmosphere was added 4-dimethylaminopyridine (6.3 mmol). After stirring for 15 minutes, the mixture was cooled to −20° C. and a solution of benzylchloroformate (3.6 mmol) in dry dichloromethane (15 ml) was added dropwise. The solvent was evaporated and the residue purified by flash chromatography using hexane:ethyl acetate (3:1) as eluent to give the title compound (1.2 g).

δ ($^1$H, CDCl$_3$): 9.70 (s, 1H, CHO), 7.35 (m, 15H, 3×Ph), 6.96 (s, 1H, CHPh$_2$), 5.99 (dd, 1H, H-2, J=1.5 and 3.6 Hz), 5.18 (AB system, 2H, OCH2Ph, J=12 Hz), 5.00 (dd, 1H, H-2', J=1.5 and 4.2 Hz), 4.70 (d, 1H, H-1', J=1.8 Hz), 4.13 (m, 1H, H-3'), 4.01 and 3.66 (d,d, 1H, 1H, 8a-CH$_2$, J=9 Hz), 3.75 (m, 1H, H-5'), 3.40 (s, 3H, OMe), 3.17 (dd, 1H, H4', J=3.3 and 8.4 Hz), 2.62 (t, 1H, H-1, J=3.6 Hz), 2.43 (d, 1H, OH, J=2.4 Hz), 2.21 (m, 1H, CH(CH$_3$)$_2$).

INTERMEDIATE 25

[1R-(1α, 3aβ, 4β, 4aβ, 7β, 7aα, 8aβ)] 8a-[(2-O-Benzyloxycarbonyl-6-deoxy-4-O-methyl-3-O-(2-tetrahydropyranyl)-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester A mixture of Intermediate 24 (0.300 g) and 2,3-dihydropyran (0.138 ml) in dichloromethane (10 ml) containing pyridinium p-toluenesulphonate (0.019 g) was stirred at room temperature for 20 hours. After removal of the solvent in vacuo, the residue was chromatographed on silica gel flash column eluting with 1% dichloromethane in methanol to afford the title compound (0.208 g) as a 3:2 diastereomeric mixture.

δ ($^1$H, CDCl$_3$) only major diastereomer: 9.72 (s, 1H, CHO), 7.43 to 7.25 (m, 15H, 3'Ph), 6.97 (s, 1H, Ph$_2$CH), 6.00 (dd, 1H, H-2, J=1.2 and 3.0 Hz), 5.16 (sist AB, 2H, PhCH$_2$OCO), 5.04 (dd, 1H, H-2', J=1.2 and 4.2 Hz), 4.80 (m, 1H, H-1"), 4.68 (brs, 1H, H-1'), 4.21 (dd, 1H, H-3', J=3.0 and 4.5 Hz).

INTERMEDIATE 26

[1R-(1α, 3aβ, 4β, 4aβ, 7β, 7aα, 8aβ)] 8a-[(2,3,6-Trideoxy-2,3-difluoro-4-O-methyl-β-D-glucopyranosyloxy)methyl]-4-(1,3-dioxolan-2-yl)-4,4a,5,6,7,7a,8,8a-octahydro-7-methyl-3-(1-methylethyl)-1,4-methano-s-indacene-3a(1H)-carboxylic acid, diphenylmethyl ester A solution of Intermediate 12 (500 mg) in anhydrous dichloromethane (8 ml) at −40° C. was treated with diethylaminosulfur trifluoride (DAST, 0.35 ml). The cooling bath was removed and the mixture was stirred overnight at room temperature. The mixture was cooled to −20° C., the reaction quenched by addition of methanol (2 ml) and then concentrated under reduced pressure. Flash chromatography on silica gel eluting with hexane:ethyl acetate (20:1), (10:1) and (4:1) gave the title compound (140 mg) as a white foam.

δ ($^1$H, CDCl$_3$): 7.26–7.46 (m, 10H, 2Ph), 6.89 (s, 1H, CHPh$_2$), 5.87 (dd, 1H, H-2, J=1.2 and 3.6 Hz), 5.07 (s, 1H, CH-dioxolane), 4.58–4.70 and 4.41–4.52 (2m, 1H, H-2', J$_{HF}$=53.1 and 17.1, J$_{HH}$=8.7 and 8.1 Hz), 4.23 (d, 1H, H-1', J=8.4 Hz), 4.30–4.40 and 4.12–4.21 (2m, 1H, H-3', J$_{HF}$=53.1 and 15.3 Hz, J$_{HH}$=8.1 Hz), 4.05 (d, 1H, 8aCH$_2$, J=9.3 Hz), 3.77–3.89 (m, 4H, of 2CH$_2$ in dioxolane protecting group and 1H of 8aCH$_2$), 3.55 (d, 3H, 4'—OCH$_3$, J$_{HF}$=1.2 Hz), 3.20–3.30 (m, 1H, H-5'), 2.96–3.07 (dq, 1H, H4', J$_{HF}$=13.2 Hz, J$_{HH}$=8.4 and 9.6 Hz), 2.60–2.70 (m, 2H, H-1 and 2CH isopropyl).

INTERMEDIATE 27

[1R-(1α, 3aβ, 4β, 4aβ, 7β, 7aα, 8aβ)] 8a-[(2,3,6-Trideoxy-4-O-methyl-3-oxo-β-D-allopyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester A solution of trifluoroacetic anhydride (0.1 ml) in dry dichloromethane (5 ml) at −60° C. under nitrogen was treated with dimethylsulfoxide (0.06 ml). After 10 minutes, a solution of Intermediate 10 (0.39 mmol) in dry dichloromethane (5 ml) was added followed, after 60 minutes, by triethylamine (0.24 ml). The mixture was stirred at −60° C. to −20° C. for 2 hours and washed with water. After removal of the solvent, the residue was purified by flash chromatography using hexane:ethyl acetate (3:1) as eluent to give the title compound (131 mg).

δ ($^1$H, CDCl$_3$): 9.72 (s, 1H, CHO), 7.35 (m, 10H, 2×Ph), 6.97 (s, 1H, CHPh$_2$), 6.03 (dd, 1H, H-2, J=1.5 and 3.6 Hz), 4.46 (dd, 1H, H-1', J=2.7 and 8.9 Hz), 4.07 and 3.71 (d,d, 1H, 1H, 8a-CH$_2$, J=9 Hz), 3.42 (m, 2H, H4' and H-5'), 2.70 (m, 3H, H-1 and CH$_2$—2'), 2.25 (m, 1H, CH(CH$_3$)$_2$), 1.43 (d, 3H, CH$_3$—6', J=5.7 Hz).

INTERMEDIATE 28

[1R-(1α, 3aβ, 4β, 4aβ, 7β, 7aα, 8aβ)] 8a-[(3,6-Dideoxy-2-O-benzyloxycarbonyl-4-O-methyl-3-oxo-β-D-allopyranosyloxy)methyl]-4-formyl-4,4a,5,6,7,7a,8,8a-octahydro-7-methyl-3-(1-methylethyl)- 1,4-methano-s-indacene-3a(1H)-carboxylic acid, diphenylmethyl ester To a solution of trifluoroacetic anhydride (65 μl) in dry dichloromethane (2 ml) under nitrogen atmosphere at −60° C. were added dropwise dimethylsulphoxide (33 μl) and a solution of Intermediate 24 (250 mg) in dichloromethane. The resulting solution was stirred for 40 minutes, triethylamine (0.20 ml) was added and the reaction mixture kept at −20° C. overnight. The mixture was then poured into water, the aqueous phase extracted with dichloromethane, the organic phase washed with brine, dried (magnesium sulphate) and evaporated to dryness. Flash chromatography on silica gel eluting with ethyl acetate:hexane (2:8) afforded the title compound (152 mg) as a foam.

δ ($^1$H, CDCl$_3$): 9.69 (s, 1H, CHO), 7.43-7.25 (m, 10H, 2Ph), 6.95 (s, 1H, CHPh$_2$), 5.91 (dd, 1H, H-2, J=1.5 and 3.3 Hz), 5.27 (d, 1H, PhCH$_2$O, J=12.0 mHz), 5.20 (d, 1H, PhCH$_2$O, J=12.0 Hz), 4.99 (dd, 1H, H-2', J=1.2 and 7.8 Hz), 4.37 (d, 1H, H-1', 7.8 Hz), 4.07 (d, 1H, 8aCH$_2$, J=9.0 Hz), 3.71 (d, 1H, 8aCH$_2$, J=12.0 Hz), 3.53 (s, 3H, 4'—O—CH$_3$), 3.51 (dd, 1H, H-4', J=1.2 and 9.6 Hz), 3.42 (dq, 1H, H-5', J$_d$=9.6 Hz, J$_q$=6.0 Hz), 2.62 (t, 1H, H-1, J=3.9 Hz).

INTERMEDIATE 29

[1R(1α, 3aβ, 4β, 4aβ, 7β, 7aα, 8aβ)] 8a-[(6-Deoxy-2-O-benzyloxycarbonyl-4-O-methyl-β-D-altropyranosyloxy)methyl]-4-(1,3-dioxolan-2-yl)-4,4a,5,6,7,7a,8,8a-octahydro-7-methyl-3-(1-methylethyl)-1,4-methano-s-indacene-3a(1H)-carboxylic acid, diphenylmethyl ester To a solution of Intermediate 24 (2.03 g) in methanol (18 ml) were added ethylene glycol (30 ml), methyl orthoformate (2.5 ml) and p-toluensulphonic acid (31 mg), and the resulting solution was stirred under nitrogen atmosphere at 35° C. for 3 hours. The solution was then partitioned between 10% sodium bicarbonate and ethyl acetate (100 ml), and the aqueous phase was extracted with more ethyl acetate (2×100 ml), washed with brine, dried (magnesium sulphate) and evaporated to dryness. The residue was flash chromatographed on silica gel eluting with hexane:ethyl acetate (6:4) to yield the title compound (2.3 g).

δ ($^1$H, CDCl$_3$): 7.46-7.20 (m, 10H, 2Ph), 6.92 (s, 1H, CHPh$_2$),5.97 (dd, 1H, H-2, J=1.2 and 3.6 Hz), 5.22 (d, 1H, BnCH$_2$O, J=12.3 Hz), 5.14 (d, 1H, BnCH$_2$O, J=12.3 Hz), 5.05 (s, 1H, OCHO), 4.99 (dd, 1H, H-2', J=1.8 and 4.5 Hz), 4.69 (d, 1H, H-1', J=1.8 Hz), 4.19-4.15 (m, 1H, H-3'), 4.01 (d, 1H, 8aCH$_2$, J=9.0 Hz), 3.89-3.74 (m, 5H, H-5', 2CH$_2$O), 3.71 (d, 1H, 8aCH$_2$, J=9.0 Hz), 3.40 (s, 3H, 4—O—CH$_3$), 3.17 (dd, 1H, H4', J=3.3 and 8.4 Hz).

INTERMEDIATE 30

[1R-(1α, 3aβ, 4β, 4aβ, 7β, 7aα, 8aβ)] 8a-[(3,6-Dideoxy-2-O-benzyloxycarbonyl-4-O-methyl-3-oxo-β-D-allopyranosyloxy)methyl]-4-(dioxolan-2-yl)-4,4a,5,6,7,7a,8,8a-octahydro-7-methyl-3-(1-methylethyl)-1,4-methano-s-indacene-3a(1H)-carboxylic acid, diphenylmethyl ester To a solution of trifluoroacetic anhydride (0.64 ml) in dry dichloromethane (5 ml) under nitrogen atmosphere at −60° C. were added dropwise dimethylsulphoxide (0.35 ml) and a solution of Intermediate 29 (1.9 g) in dry dichloromethane (10 ml). The resulting solution was stirred for 1 hour, triethylamine (1.24 ml) was added and stirring was continued for 2 hours allowing the temperature to reach −20° C. The reaction mixture was partitioned between water and dichloromethane (100 ml), and the organic phase was washed with brine and dried (magnesium sulphate). The solution was then concentrated to 40 ml, triethylamine (2 ml) was added and the solution stirred for 2 hours at room temperature. The solvent was then evaporated off and the residue flash chromatographed on silica gel eluting with ethyl acetate:hexane (2:8) to obtain the title compound (1.6 g).

δ ($^1$H, CDCl$_3$): 7.45-7.22 (m, 10H, CHPh$_2$), 5.73 (dd, 1H, H-2, J=1.5 and 3.9 Hz), 5.28-5.19 (m, 2H, AB system, OCH$_2$Ph), 5.08 (s, 1H, OCHO), 4.99 (dd, 1H, H-2', J=1.2 and 8.1 Hz), 4.37 (d, 1H, H-1', J=8.1 Hz), 4.06 (d, 1H, 8aCH$_2$, J=9.0 Hz), 3.88-3.78 (m, 4H, 2×CH$_2$O), 3.52 (s, 3H, 4—O—CH$_3$), 3.76 (d, 1H, BaCH$_2$, J=9.0 Hz), 3.46-3.39 (m, 1H, H-5').

INTERMEDIATE 31

[1R-(1α, 3aβ, 4β, 4aβ, 7β, 7aα, 8aβ)] 8a-[(3,6-Dideoxy-2-O-benzyloxycarbonyl-3-allyloxyimine-4-O-methyl-β-D-allopyranosyloxy)methyl]-4-(1,3-dioxolan-2-yl)-4,4a,5,6,7,7a,8,8a-octahydro-7-methyl-3-(1-methylethyl)-1,4-methano-s-indacene-3a(1H)-carboxylic acid, diphenylmethyl ester A mixture of Intermediate 30 (250 mg) and O-allylhydroxylamine hydrochloride (109 mg) in dry pyridine (5 ml) was stirred at 80° C. for 4 hours. The solvent was evaporated to dryness and the residue flash chromatographed on silica gel eluting with hexane:ethyl acetate (85:15) to obtain the title compound (193 mg) as a mixture of Z:E isomers in a 3:1 ratio.

δ ($^1$H, CDCl$_3$): 7.43-7.21 (m, 10H, 2Ph), 6.91 (s, 1H, CHPh$_2$), 6.0-5.8 (m, 1H, HC=C), 5.67 (d, 1H, H-2, J=6.6 Hz), 5.63 (dd, 1H, H-2, J=1.2 and 2.4 Hz), 5.30-5.06 (m, 5H,2×H—C=C, OCHO, OCH$_2$Ph), 4.74 (d, 1H, H-1', J=6.6 Hz), 4.68-4.58 (m, 2H, OCH$_2$C=C), 4.04-3.75 (m, 6H, H-4', H-5' 2×OCH$_2$), 3.97 (d, 1H, 8aCH$_2$, J=9.0 Hz), 3.66 (d, 1H, 8aCH$_2$, J=9.0 Hz), 3.26 (s, 3H, 4—O—CH$_3$).

INTERMEDIATE 32

[1R-(1α, 3aβ, 4β, 4aβ7β, 7aα, 8aβ)] 8a-[(3-O-Benzoyl-6-deoxy-4-O-methyl-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester A stirred solution of Intermediate 1 (500 mg) and dibutyltin oxide (246 mg) in dry toluene (15 ml) was refluxed for 2 hours in a flask fitted with a Dean-Stark condenser under nitrogen atmosphere. The reaction mixture was allowed to cool to room temperature and then treated with benzoyl chloride (95 μl) and triethylamine (0.32 ml). After stirring for 2 hours under reflux, the reaction mixture was concentrated under reduced pressure and the residue purified by flash column chromatography eluting with hexane:ethyl acetate (8:1 to 3:1). The appropriate fractions were combined and the solvents evaporated to yield the the title compound (300 mg) as a white foam.

δ ($^1$H, CDCl$_3$): 9.73 (s, 1H, CHO), 8.05 and 7.26–7.59 (2m, 2H and 13H, 3Ph), 6.99 (s, 1H, CHPh$_2$), 6.30 (dd, 1H, H-2, J=3.3 and 1.2 Hz), 5.73 (dd, 1H, H-3', J=3 and 0.9 Hz), 4.69 (d, 1H, H-1', J=1.2 Hz), 3.79 and 4.10 (2d, 2H, 8aCH$_2$, J=9 Hz), 3.94-3.85 (m, 2H, H-2' and H-5'), 3.38 (s, 3H, 4'OMe), 3.41 (dd, 1H, H-4', J=3 and 9 Hz), 2.73 (t, 1H, H-1, J=3.9 Hz), 2.38 (d, 1H, 2'—OH, J=3.3 Hz).

INTERMEDIATE 33

[1R-(1α, 3aβ, 4β, 4aβ, 7β, 7aα, 8aβ)] 8a-[(3-O-Benzyloxycarbonyl-6-deoxy-4-O-methyl-β-D-altropyranosyloxy)methyl]-4-formyl-4,4a,5,6,7,7a,8,8a- octahydro-7-methyl-3-(1-methylethyl)-1,4-methano-s-indacene-3a(1H)-carboxylic acid diphenylmethyl ester A mixture of Intermediate 1 (3 mmol) and dibutyltin oxide (3.9 mmol) in dry toluene (40 ml) was stirred under reflux in a flask fitted with a Dean-Stark condenser for 2 hours. The mixture was cooled and 4-dimethylaminopyridine (3.2 mmol) and benzyloxycarbonyl chloride (3.3 mmol) were added. After 30 minutes, the solvent was evaporated and the residue purified by flash column chromatography on silica gel eluting with hexane-:ethyl acetate (15:1 to 3:1). Appropriate fractions were combined and concentrated to give the title compound (356 mg).

δ ($^1$H, CDCl$_3$): 9.73 (s, 1H, CHO), 7.36 (m, 15H, 3×Ph), 6.98 (s, 1H, CHPh$_2$), 6.03 (dd, 1H, H-2, J=1.5 and 3.6 Hz), 5.32 (dd, 1H, H-3', J=3 and 3.9 Hz), 5.22 and 5.15 (d,d, 1H, 1H, OCH$_2$Ph, J=12 Hz), 4.61 (d, 1H, H1', J=1.5 Hz), 4.07 and 3.73 (d,d, 1H, 1H, 8a-CH$_2$, J=9.3 Hz), 3.85 (m, 1H, H-2'), 3.75 (m, 1H, H-5'), 3.27 (dd, 1H, H4', J=3.3 and 9.3 Hz), 2.71 (t, 1H, H-1, J=3.9 Hz), 2.32 (d 1H, OH, J=3 Hz), 2.22 (m,1H, CH(CH$_3$)$_2$).

INTERMEDIATE 34

[1R-(1α, 3aβ, 4β, 4aβ, 7β, 7aα, 8aβ)] 8a-[(6-Deoxy-4-O-methyl-2-O-(2,2,2-trichloethoxycarbonyl)-β-D-altropyranosyloxy)methyl]-4-formyl-4,4a,5,6,7,7a8,8a-octahydro-7-methyl-3-(1-methylethyl)-1,4-methano-s-indacene-3a(1H)-carboxylic acid, diphenylmethyl ester To a cold (0° C.) solution of Intermediate 1 (200 mg) and 4-dimethylaminopyridine (100 mg) in acetonitrile (10 ml) was added dropwise a solution of 2,2,2-trichloroethyl chloroformate (50 μl) in acetonitrile (10 ml), and the mixture was stirred at 0° C. until all the starting material was consumed (tlc analysis 2:1 hexane:ethyl acetate). The solvent was removed under vacuum and the residue partitioned between ethyl acetate (50 ml) and 1N aqueous hydrochloric acid (50 ml). The organic layer was washed successively with water and brine, then dried over sodium sulphate, filtered and concentrated. The residue was purified by flash chromatography on silica gel eluting with hexane:ethyl acetate (3:1) to give the title compound (175 mg) as a colourless gum which was triturated with hexane to afford a white solid.

δ ($^1$H, CDCl$_3$): 9.71 (s, 1H, CHO), 7.45-7.2 (m, 10H, 2Ph), 6.97 (s, 1H, CHPh$_2$), 6.04 (dd, 1H, H-2, J=1.2 and 3.6 Hz), 5.03 (dd, 1H, H-2', J=1.5 and 4.2 Hz), 4.84, 4.75 (2d, 2H, Cl$_3$CCH$_2$O, J$_{AB}$=12 Hz), 4.72 (d, 1H, H-1'), 4.2 (m, 1H, H-3'), 4.05, 3.68 (2d, 2H, 8aCH$_2$, J$_{AB}$=9 Hz), 3.82-3.71 (m, 1H, H-5'), 3.43 (s, 31H, OCH$_3$), 3.21 (dd, 1H, H4', J=3 and 8.4 Hz), 2.70 (m, 1H, H-1), 2.47 (d, 1H, OH3', J=2.1 Hz), 2.28-2.16 (m, 1H, CH(CH$_3$)$_2$).

INTERMEDIATE 35

[1R-(1α, 3aβ, 4β, 4aβ, 7β, 7aα, 8aβ)] 8a-[(2-O-Benzyloxycarbonyl-3-O-butoxyacetyl-6-deoxy-4-O-methyl-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester To a solution of Intermediate 24 (400 mg) in dry dichloromethane (15 ml) at room temperature were added 4-dimethylaminopyridine (67 mg) and a solution of butoxyacetyl chloride (0.1 ml) in dichloromethane (5 ml). After stirring for 1 hour the solvent was removed and the residue purified by flash column chromatography eluting with hexane:ethyl acetate (5:1) to give the title compound (350 mg).

δ ($^1$H, CDCl$_3$): 9.71 (s, 1H, CHO), 7.25–7.43 (m, 15H, 3Ph), 6.96 (s, 1H, CHPh$_2$), 5.97 (dd, 1H, H-2, J=3.3 and 0.9 Hz), 5.53 (dd, 1H, H-3', J=4.8 and 3.3 Hz), 5.18 (AB system, 2H, CH$_2$—Ph, J=12 Hz), 4.93 (dd, 1H, H-2', J=1.5 and 4.8 Hz), 4.63 (d, 1H, H-1', J=1.5 Hz), 4.13 (AB system, 2H, OCH$_2$CO$_2$, J=14 Hz), 3.66 and 3.99 (2d, 2H, 8aCH$_2$, J=9 Hz), 3.73 (m, 1H, H-5'), 3.53 (m, 2H, CH2O), 3.32 (s, 3H, 4'—OCH$_3$), 3.24 (dd, 1H, H-4', J=8.4 and 3 Hz).

INTERMEDIATE 36

[1R-(1α, 3aβ, 4β, 4aβ, 7β, 7aα, 8aβ)] 8a-[(2-O-Benzyloxycarbonyl-6-deoxy-4-O-methyl-3-O-octanoyl-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester To a solution of Intermediate 24 (600 mg) and 4-dimethylaminopyridine (276 mg) in dry dichloromethane (30 ml) at room temperature was added octanoyl chloride (170 μl) and the mixture was stirred for 3 hours. The solution was washed with water (2×50 ml), dried over magnesium sulfate and concentrated under reduced pressure. The residue was purified by flash cromatography eluting with hexane:ethyl acetate (4:1) to give the title compound (490 mg) as a white foam.

δ ($^1$H, CDCl$_3$): 9.71 (s, 1H, CHO), 7.45-7.25 (m, 15H, 3Ph), 6.97 (s, 1H, CHPh$_2$), 5.97 (dd, 1H, H-2, J=1.5 and 3.6 Hz), 5.46 (dd, 1H, H-3', J=3 and 4.5 Hz), 5.18 (AB system 2H, CH$_2$Ph, J=12 Hz), 4.90 (dd, 1H, H-2', J=1.5 and 4.8 Hz), 4.63 (d, 1H, H-1', J=1.8), 3.98 and 3.67 (2d, 2H, 8aCH$_2$, J=8.7 Hz), 3.74 (m, 1H, H-5'), 3.32 (s, 3H, OCH$_3$), 3.22 (dd, 1H, H4', J=3 and 8.1 Hz), 2.57 (t, 1H, H-1, J=3.9 Hz), 2.37 (dt, 2H, CH$_2$CO, J=1.8 and 7.5 Hz), 1.4-1.2 (m, 5CH$_2$ and 6'CH$_3$).

INTERMEDIATE 37

[1R-(1α, 3aβ, 4β, 4aβ, 7β, 7aα, 8aβ)] 8a-[(2-O-Benzyloxycarbonyl-6-deoxy-3-O-methoxyacetyl-4-O-methyl-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester To a solution of Intermediate 24 (400 mg) in dry dichloromethane (15 ml) at room temperature were added 4-dimethylaminopyridine (70 mg) and methoxyacetyl chloride (51 μl) in dichloromethane (5 ml). After stirring for 2 hours the solvent was removed and the residue purified by flash column chromatography eluting with hexane:ethyl acetate (5:1) to give the title compound (352 mg).

δ ($^1$H, CDCl$_3$): 9.71 (s, 1H, CHO), 7.20–7.42 (m, 15H, 3Ph), 6.96 (s, 1Ha, CHPh$_2$), 5.97 (dd, 1H, H-2, J=3.3 and 0.39 Hz), 5.54 (dd, 1H, H-3', J=4.5 and 3 Hz), 5.18 (AB system, 2H, CH2Ph, J=12 Hz), 4.93 (dd, 1H, H-2', J=4.5 and 1.5 Hz), 4.63 (d, 1H, H-1', J=1.5 Hz), 4.10 (AB system, 2H, OCH$_2$CO$_2$, J=12 Hz), 3.66 and 3.98 (2d, 2H, 8aCH$_2$, J=9 Hz), 3.72 (dq, 1H, H-5', J=9 and 6 Hz), 3.34 (s, 3H, 4'OCH$_3$), 3.45 (s, 3H, CH$_3$OCH$_2$CO$_2$), 3.24 (dd, 1H, H-4', J=9 and 3 Hz), 2.57 (t, 1H, H-1, J=3.9 Hz).

INTERMEDIATE 38

[1R-(1α, 3aβ, 4β, 4aβ, 7β, 7aα, 8aβ)] 8a-[(6-Deoxy-4-O-methyl-3-O-((E)-2-methyl-2-hexenoyl)-2-O-(2,2,2-trichloroethoxycarbonyl)-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester A mixture of trans-2-methyl-2-hexenoic acid (61 mg), triethylamine (167 ml), Intermediate 34 (227 mg), 2-chloro-1-methylpyridinium iodide (123 mg) and a catalytic amount of 4-dimethylaminopyridine in dry dichloromethane (10 ml) was refluxed for 10 minutes. A further quantity of 4-dimethylaminopyridine (88 mg) was added and reflux continued for 2.5 hours. The solvent was removed in vacuo and the residue partitioned between ethyl acetate (50 ml) and water (50 ml). The organic layer was washed successively with aqueous hydrochloric acid (1N, 30 ml), saturated aqueous sodium hydrogen carbonate solution (30 ml) and brine (30 ml), then dried ($Na_2SO_4$), filtered and concentrated in vacuo. The residue was flash chromatographed over silica gel eluting with hexane:ethyl acetate (8:1) and the required fractions combined and evaporated to give the title compound (205 mg) as a white foam.

($^1$H, $CDCl_3$): 9.72 (s, 1H, CHO), 7.46–7.22 (m, 10H, 2Ph), 6.98 (s, 1H, $CHPh_2$), 6.82 (m, 1H, $RO_2C(CH_3)=CH—R$), 6.03 (m, 1H, H-2), 5.54 (m, 1H, H-3'), 5.0 (m, 1H, H-2'), 4.84, 4.76 (2d, 2H, $Cl_3CCH_2$, $J_{AB}$=12 Hz), 4.67 (d, 1H, H-1', J=1.5 Hz), 4.05, 3.71 (2d, 2H, $8aCH_2$, $J_{AB}$=9 Hz), 3.8 (m, 1H, H-5'), 3.37 (s, 3H, —$OCH_3$), 3.32 (m, 1H, H4'), 2.68 (bt, 1H, H-1, J=3.6 Hz), 2.3-2.12 (m, 3H, $CHMe_2$ and $RO_2CC(CH_3)=CH—CH_2—R$).

INTERMEDIATE 39

[1R-(1α, 3aβ, 4β, 4aβ7β, 7aα, 8aβ)] 8a-[(6-Deoxy-4-O-methyl-3-O-((E)-2-methyl-2-hexenoyl)-2-O-(2,2,2-trichloroethoxycarbonyl)-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid A solution of Intermediate 38 (194 mg) in a (20:1) trifluoroacetic acid:water mixture (5 ml) at 0° C. was stirred for 45 minutes. The solvent was removed in vacuo and the residue co-evaporated with toluene (2×10 ml) to a yellow oil. This was purified by preparative tlc (Merck 5717) eluting with dichloromethane:methanol (20:1) and washing the product off the silica gel with ethyl acetate:methanol (6:1). Removal of solvent gave the title compound (138 mg) as a white foam.

δ ($^1$H, $CDCl_3$): 9.73 (s, 1H, CHO), 6.81 (m, 1H, $RO_2CC(CH_3)=CH—R$), 6.05 (dd, 1H, H-2, J=1.5 and 3.6 Hz), 5.55 (dd, 1H, H-3', J=3 and 4.5 Hz), 5.02 (dd, 1H, H-2', J=1.5 and 4.5 Hz), 4.81 (m, 2H, $Cl_3CCH_2$), 4.70 (d, 1H, H-1', J=1.5 Hz), 4.17, 3.57 (2d, 2H, $8aCH_2$, $J_{AB}$=9 Hz), 3.8 (m, 1H, H-5'), 3.36 (s, 3H, —$OCH_3$), 3.31 (m, 1H, H-4'), 2.59 (m, 1H, H-1), 2.32 (m, 1H, $CHMe_2$), 2.17 (m, 2H, $RO_2C—C(CH_3)=CH—CH_2—R$).

INTERMEDIATE 40

[1R-(1α, 3aβ, 4β, 4aβ, 7β, 7aα, 8aβ)] 8a-[(2-O-Benzyloxycarbonyl-3-O-(4-chlorobutyryl)-6-deoxy-4-O-methyl-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester To a solution of Intermediate 24 (500 mg) and 4-dimethylaminopyridine (457 mg) in dry dichloromethane (25 ml) at room temperature was added 4chlorobutyryl chloride (141 μl) and the mixture was stirred for 24 hours. The solution was washed with water (2×50 ml), dried over magnesium sulfate, and concentrated under reduced pressure. The residue was purified by flash cromatography eluting with hexane:ethyl acetate (3:2) to give the title compound (360 mg) as a white foam.

δ ($^1$H, $CDCl_3$): 9.7 (s, 1H, CHO), 7.45-7.24 (m, 15H, 3Ph), 6.97 (s, 1H,$CHPh_2$), 5.97 (dd, 1H, H-2, J=1.5 and 3.6 Hz), 5.46 (dd, 1H, H-3', J=3 and 4.5 Hz), 5.18 (AB system, 2H, $CH_2Ph$, J=12 Hz), 4.91 (dd, 1H, H-2', J=1.5 and 4.5 Hz), 4.64 (d,1 H, H-1', J=1.8 Hz), 3.99 and 3.67 (2d, 2H, $8aCH_2$, J=8.7 Hz), 3.75 (dd, 1H, H-5', J=6.3 and 8.4 Hz), 3.60 (t, 2H, $CH_2CO$, J=6.6 Hz), 3.26 (s, 3H, $OCH_3$), 3.22 (dd, 1H, H-4', J=3.0 and 8.4 Hz), 2.58 (m, 3H, 1 H, H-1 and 2H, $CH_2Cl$).

INTERMEDIATE 41

[1R-(1α, 3aβ, 4β, 4aβ, 7β, 7aβ, 8aβ)] 8a-[(2-O-Benzyloxycarbonyl-6-deoxy-4-O-methyl-3-O-(2-methylpropanoyl)-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester A solution of isobutyryl chloride (0.054 ml) in dichloromethane (5 ml) was added to a mixture of Intermediate 24 (0.415 g) and 4-dimethylaminopyridine (0.064 g) in dichloromethane (10 ml). The reaction mixture was stirred for 20 hours. Water (15 ml) was added into the mixture and the organic layer was separated. The solvent was removed in vacuo and the residue was chromatographed on silica gel flash column eluting with hexane:ethyl acetate (3:1) to give the title compound (0.276 g).

δ ($^1$H, $CDCl_3$): 9.71 (s, 1H, CHO), 7.30 (m, 15H, 3×Ph), 6.97 (s, 1H, $Ph_2CH$), 5.97 (dd, 1H, H-2, J=1.2 and 3.6 Hz), 5.40 (dd, 1H, H-3', J=3.0 and 4.5 Hz), 5.18 (AB system, 2H, $PhCH_2OCO$), 4.90 (dd, 1H, H-2', J=1.5 and 4.8 Hz), 4.62 (d, 1H, H-1, J=1.8 Hz), 3.98 (d, 1H, $8aCH_2$, $J_{AB}$=9.0 Hz), 3.75 (m, 1H, H-5'), 3.67 (d, 1H, $8aCH_2$, $J_{AB}$=9.0 Hz), 3.32 (s, 3H, OMe), 3.22 (dd, 1H, H-4', J=3.0 and 8.1 Hz), 2.62 (m, 2H, H-1 and $(CH_3)_2CHCO_2$).

INTERMEDIATE 42

[1R-(1α, 3aβ, 4β, 4aβ, 7β, 7aα, 8β)] 8a-[(2-O-Benzyloxycarbonyl-6-deoxy-4-O-methyl-3-O-propionyl-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester Propionic acid (54 μl), 2-chloro-1-methylpyridinium iodide (184 mg), triethylamine (250 μl), Intermediate 24 (285 mg), 4-dimethylaminopyridine (132 mg) and dry dichloromethane (20 ml) were mixed and stirred at room temperature for 18 hours. The solvent was removed in vacuo and the residue chromatographed on silica gel eluting with hexane:ethyl acetate (4:1). The appropriate fractions were combined and the solvent was evaporated to give the title compound (285 mg) as a white foam.

δ ($^1$H, $CDCl_3$): 9.71 (s, 1H, CHO), 7.44-7.22 (m, 15H, 3Ph), 6.96 (s, 1H, $CHPh_2$), 5.97 (dd, 1H, H-2, J=1.5 and 3.3 Hz), 5.46 (dd, 1H, H-3', J=3 and 4.8 Hz), 5.22, 5.14 (2d, 2H, PhCH2O, $J_{AB}$=12 Hz), 4.91 (dd, 1H, H-2', J=1.5 and 4.8 Hz), 4.63 (d, 1H, H-1', J=1.5 Hz), 3.99, 3.67 (2d, 2H, $8aCH_2$, $J_{AB}$=8.7 Hz), 3.75 (m, 1H, H-5'), 3.33 (s, 3H, —$OCH_3$), 3.23 (dd, 1H, H-4', J=3 and 8.4 Hz), 2.57 (m, 1H, H-1), 2.4 (dq, 2H, $RO_2CCH_2$—Me, J=7.5 Hz (q) and 1.2 Hz (d)), 2.22 (m, 1H, $CHMe_2$),1.16 (t, 3H, $RO_2CCH_2CH_3$, J=7.5 Hz).

INTERMEDIATE 43

[1R-(1α, 3aβ, 4β, 4aβ, 7β, 7aα, 8aβ)] 8a-[(2-O-Benzyloxycarbonyl-6-deoxy-4-O-methyl-3-O-(trans-4-methyl-1-cyclohexanecarbonyl)-β-D-altropyranosyloxy) methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester A mixture of trans-4-methyl-1-cyclohexanecarboxylic acid (102 mg), 2-chloro-1-methylpyridinium iodide (184 mg), triethylamine (250 μl), Intermediate 24 (285 mg) and 4-dimethylaminopyridine (132 mg) in dry dichloromethane (20 ml) was stirred at room temperature for 15 hours. The solvent was removed in vacuo and the residue purified by column chromatography on silica gel eluting with hexane- :ethyl acetate (4:1). The required fractions were combined and evaporated to give the title compound (310 mg) as a white foam.

δ ($^1$H, CDCl$_3$): 9.71 (s, 1H, CHO), 7.44-7.22 (m, 15H, 3Ph), 6.97 (s, 1H, CHPh$_2$), 5.97 (dd, 1H, H-2, J=1.2 and 3.3 Hz), 5.43 (dd, 1H, H-3', J=3.3 and 4.8 Hz), 5.21, 5.14 (2d, 2H, Ph-CH$_2$—O, J$_{AB}$=12 Hz), 4.89 (dd, 1H, H-2', J=1.8 and 4.8 Hz), 4.62 (d, 1H, H-1', J=1.8 Hz), 3.99, 3.68 (2d, 2H, 8aCH$_2$, J$_{AB}$=9 Hz), 3.75 (m, 1H, H-5'), 3.31 (s, 3H, OCH$_3$), 3.21 (dd, 1H, H4', J=3.3 and 8.4 Hz), 2.57 (m, 1H, H-1), 2.34-2.16 (m, 2H, CHMe$_2$+RO$_2$C—CH— (cyclohexane)), 0.89 (d, 3Haprox, H$_3$C-cyclohexane-CO$_2$R).

INTERMEDIATE 44

[1R-(1α, 3aβ, 4β, 4aβ, 7β, 7aα, 8aβ)] 8a-[(3-O-trans-Cinnamoyl-6-deoxy-4-O-methyl-2-O-(2,2,2-trichloroethoxycarbonyl)-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester A cold (0° C.) solution of Intermediate 34 (75 mg) in dry dichloromethane (4 ml) under nitrogen was treated with 4-dimethylaminopyridine (50 mg) and trans-cinnamoyl chloride (30 mg). The mixture was stirred at room temperature until all the starting material was consumed (5 hours). The reaction was quenched with water and the mixture stirred for 15 minutes and then partitioned between ethyl acetate (50 ml) and 1N aqueous hydrochloric acid (50 ml). The organic layer was washed successively with water and brine, then dried (Na$_2$SO$_4$), filtered and concentrated. The residue material was flash chromatographed using hexane to 3:1 hexane:ethyl acetate as eluent to give the title compound (90 mg).

δ ($^1$H, CDCl$_3$): 9.72 (s, 1H, CHO), 7.74 (d, 1H, PhCH=CH—CO$_2$R, J=15.9 Hz), 7.6-7.2 (m, 15H, 3Ph), 6.98 (s, 1H, CHPh$_2$), 6.49 (d, 1H, PhCH=CH—CO$_2$R), 6.04 (dd, 1H, H-2, J=1.2 and 3.6 Hz), 5.60 (dd, 1H, H-3', J=3.3 and 4.5 Hz), 5.06 (dd, 1H, H-2', J=1.5 and 4.5 Hz), 4.9-4.7 (m, 3H, Cl$_3$CCH$_2$O, H-1'), 4.07, 3.72 (2d, 2H, 8aCH$_2$, J$_{AB}$=9 Hz), 3.94-3.82 (m, 1H, H-5'), 3.44-3.32 (m, 4H, —OCH$_3$, H4'), 2.7 (t, 1H, H-1, J=3.6 Hz), 2.3–2.18 (m, 1H, —CHMe$_2$).

INTERMEDIATE 45

[1R-(1α, 3aβ, 4β, 4aβ, 7β, 7aα, 8aβ)] 8a-[(3-O-trans-Cinnamoyl-6-deoxy-4-O-methyl-2-O-(2,2,2-trichlorethoxycarbonyl)-62-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid A suspension of Intermediate 44 (295 mg) in trifluoroacetic acid:water (4:1;10 ml) at 0° C. was stirred for 1.5 hours. The solvent was removed in vacuo and the crude co-evaporated with toluene (3×5 ml). The residue was flash chromatographed on silica gel eluting with dichloromethane:methanol (99:1 to 95:5) and appropriate fractions were combined and concentrated to give the title compound (200 mg).

δ ($^1$H, CDCl$_3$): 9.73 (s, 1H, CHO), 7.74 (d, 1H, Ph—CH=CH—CO$_2$R, J=15.9 Hz), 7.6–7.36 (m, 5H, Ph), 6.48 (d, 1H, Ph—CH=CH—CO$_2$R, J=15.9 Hz), 6.06 (dd, 1H, H-2, J=1.5 and 3.6 Hz), 5.61 (dd, 1H, H-3', J=3.3 and 4.5 Hz), 5.07 (dd, 1H, H-2', J=1.5 and 4.5 Hz), 4.82 (s, 2H, Cl$_3$CCH$_2$O), 4.77 (d, 1H, H-1', J=1.5 Hz), 4.15, 3.61 (2d, 2H, 8aCH$_2$, J$_{AB}$=9 Hz), 3.95-3.80 (m, 1H, H-5'), 3.40 (s, 3H, —OCH$_3$), 3.35 (dd, 1H, H-4', J=3.3 and 8.4 Hz), 2.62 (m, 1H, H-1), 2.32 (m, 1H, —CHMe$_2$).

INTERMEDIATE 46

[1R-(1α, 3aβ, 4β, 4aβ, 7β, 7aα, 8aβ)] 8a-[(6-Deoxy-3-Omethacryloyl-4-O-methyl-2-O-(2,2,2-trichloroethoxycarbonyl)-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester A mixture of Intermediate 34 (100 mg), triethylamine (80 μl), methacrylic acid (21 μl), 2-chloro-1-methylpyridinium iodide (68 mg) and a catalytic amount of 4-dimethylaminopyridine in dry dichloromethane (10 ml) was refluxed under nitrogen for 5 minutes. A further quantity of 4-dimethylaminopyridine (45 mg) was added and reflux was continued until all the starting material was consumed (tlc control 4:1 hexane:ethyl acetate). The solvent was removed in vacuo and the residue partitioned between ethyl acetate (50 ml) and 1N aqueous hydrochloric acid (50 ml). The organic layer was washed successively with saturated aqueous sodium hydrogen carbonate solution, water and brine, then dried (Na$_2$SO$_4$), filtered and concentrated in vacuo. The residue was purified by flash chromatography eluting with hexane:ethyl acetate (4:1) to give the title compound (60 mg).

δ ($^1$H, CDCl$_3$): 9.72 (s, 1H, CHO), 7.46-7.22 (m, 10H, 2Ph), 6.98 (s, 1H, Ph$_2$CH—), 6.16 (bs, 1H, Ha—C=C), 6.03 (m, 1H, H-2), 5.65 (m, 1H, Hb—C=), 5.53 (dd, 1H, H-3', J=3 and 4.8 Hz), 5.01 (dd, 1H, H-2', J=1.5 and 4.8 Hz), 4.84, 4.76 (2d, 2H, Cl$_3$CCH$_2$, J$_{AB}$=11.7 Hz), 4.67 (d, 1H, H-1', J=1.5 Hz), 4.04, 3.7 (2d, 2H, 8aCH$_2$, J$_{AB}$=9 Hz), 3.8 (m, 1H, H-5'), 3.36 (s, 3H, —OCH$_3$), 3.31 (dd, 1H, H4', J=3.3 and 8.4 Hz), 2.68 (m, 1H, H-1), 2.23 (m, 1H, CHMe$_2$), 1.97 (s, 3H, H$_3$C—C=).

INTERMEDIATE 47

[1R-(1α, 3aβ, 4β, 4aβ, 7β, 7aα, 8aβ)] 8a-[(6-Deoxy-3-O-methacryloyl-4-O-methyl-2-O-(2,2,2-trichloroethoxycarbonyl)-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid A suspension of Intermediate 46 (150 mg) in trifluoroacetic acid:water (4:1;7 ml) at 0° C. was stirred for 1.5 hours. The solvent was removed in vacuo and the residue co-evaporated with toluene (3×3 ml). The residue was flash chromatographed on silica gel eluting with dichloromethane:methanol (25:1) and appropriate fractions were combined and evaporated to give the title compound (115 mg) as a white foam.

δ ($^1$H, CDCl$_3$): 9.72 (s, 1H, CHO), 6.15 (m, 1H, Ha—C=C), 6.05 (dd, 1H, H-2, J=1.5 and 3.6 Hz), 5.65 (m, 1H, Hb—C=C), 5.54 (dd, 1H, H-3', J=3 and 4.5 Hz), 5.02 (dd, 1H, H-2', J=1.8 and 4.5 Hz), 4.81 (s, 2H, Cl$_3$CCH$_2$), 4.70 (d, 1H, H-1', J=1.8 Hz), 4.1, 3.59 (2d, 2H, 8aCH$_2$, J$_{AB}$=9 Hz), 3.81 (m, 1H, H-5'), 3.36 (s, 3H, —OCH$_3$), 3.31 (dd, 1H, H4', J=3 and 8.4 Hz), 2.62 (m, 1H, H-1), 2.31 (m, 1H, CHMe$_2$), 1.97 (s, 3H, H$_3$C—C=C).

INTERMEDIATE 48

[1R-(1α, 3aβ, 4β, 4aβ, 7β, 7aα, 8aβ)] 8a-[(2-O-Benzyloxycarbonyl-6-deoxy-4-O-methyl-3-O-octyloxycarbonyl-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester To a solution of Intermediate 24 (400 mg) and 4-dimethylaminopyridine (238 mg) in dry dichloromethane (50 ml) at room temperature was added octyl chloroformate (127 μl) and the mixture was stirred for 3 hours. The solution was washed with water (2×50 ml), dried over magnesium sulfate, and concentrated under reduced pressure. The residue was purified by flash chromatography eluting with hexane:ethyl acetate (4:1) to give the title compound (320 mg) as a white foam.

δ ($^1$H, CDCl$_3$): 9.71 (s, 1H, CHO), 7.45-7.20 (m, 15H, 3Ph), 6.96 (s, 1H, CHPh$_2$), 5.97 (dd, 1H, H-2, J=1.2 and 3.3 Hz), 5.26 (dd, 1H, H-3', J=3 and 4.2 Hz), 5.18 (AB system, 2H, CH$_2$—Ph, J=12 Hz), 5.00 (dd, 1H, H-2', J=1.5 and J=4.2 Hz), 4.69 (d, 1H, H-1', J=1.5 Hz), 4.15 (t, 2H, CH$_2$OCO, J=6.6 Hz), 4.00 and 3.66 (2d, 2H, 8aCH$_2$, J=8.7 Hz), 3.78 (dd, 1H, H-5', J=6 and 9 Hz), 3.37 (s, 3H, OCH$_3$), 3.30 (dd, 1H, H4', J=3 and 8.4 Hz).

INTERMEDIATE 49

[1R-(1α, 3aβ, 4β, 4aβ, 7β, 7aα, 8aβ)] 8a-[(6-Deoxy-2-O-benzyloxycarbonyl-4-O-methyl-3-O-octylaminocarbonyl-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester To a solution of Intermediate 24 (250 mg) and octyl isocyanate (62 mg) in dry toluene (10 ml) was added a catalytic amount (5 drops) of dibutyltin diacetate, and the mixture was refluxed under nitrogen for 1 hour. The solvent was evaporated to dryness and the residue chromatographed on a silica gel flash column using hexane:ethyl acetate (7:3) as eluent to give the title compound (280 mg) as a white foam.

δ ($^1$H, CDCl$_3$): 9.70 (s, 1H, CHO), 6.96 (s. 1H, CHPh$_2$), 5.96 (dd, 1H, H-2, J=1.5 and 3.6 Hz), 5.32 (m, 1H, H-3'), 5.17 (AB system, 2H, —CH$_2$OPh, J=12.0 Hz), 4.98 (dd, 1H, H-2', J=1.8 and 5.1 Hz), 4.75 (t, 1H, —NH—C=O—), 4.62 (d, 1H, HI-1', J=1.8 Hz), 3.98 and 3.65 (2d, 2H, 8a-CH2, J=9 Hz), 3.74 (m, 1H, H-5'), 3.37 (s, 3H, 4'—OCH3), 3.25 (dd, 1H, H-4', J=3 and 8.1 Hz), 3.18 (m, 2H, —CH$_2$—NH—CO$_2$), 2.58 (t, 1H, H-1').

INTERMEDIATE 50

[1R-(1α, 3aβ, 4β, 4aβ, 7β, 7aα, 8aβ)] 8a-[(6-Deoxy-3-O-benzylaminocarbonyl-2-O-benzyloxycarbonyl-4-O-methyl-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester To a solution of Intermediate 24 (240 mg) and benzyl isocyanate (54 mg) in dry toluene (10 ml) was added a catalytic amount of dibutyltin diacetate, and the stirred mixture was refluxed under nitrogen for 6 hours. The solvent was evaporated to dryness and the residue chromatographed on a silica gel flash column eluting with hexane:ethyl acetate (5:1) to give the title compound (140 mg) as a white foam.

δ ($^1$H, CDCl$_3$): 9.70 (s, 1H, CHO), 6.95 (s, 1H, CHPh$_2$), 5.96 (dd, 1H, H-2, J=0.6 and 2.7 Hz), 5.37 (dd, 1H, H-3', J=3 and 4.8 Hz), 5.18 (AB system, 2H, O—CHPh$_2$, J=12 Hz), 5.12 (t, 1H, CH$_2$—NH—CO$_2$), 4.98 (dd, 1H, H-2', J=0.3 and 1.2 Hz), 4.61 (d, 1H, H-1', J=1.2 Hz), 4.38 (m, 2H, NH—CH$_2$—Ph), 3.98 and 3.64 (2d, 2H, 8a-CH$_2$, J=9 Hz), 3.74 (m, 1H, H-5'), 3.38 (s, 3H, 4'—OCH), 3.26 (dd, 1H, H-4', J=3 and 8.1 Hz), 2.57 (t, 1H, H-1).

INTERMEDIATE 51

[1R-(1α, 3aβ, 4β, 4aβ, 7β, 7aα, 8aβ)] 8a-[(2-O-Benzyloxycarbonyl-6-deoxy-3-O-dimethylaminocarbonyl-4-O-methyl-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester A solution of Intermediate 24 (0.500 g) in tetrahydrofuran (10 ml) was added via cannula to a solution of lithium diisopropylamide solution in tetrahydrofuran (5 ml) [prepared from duisopropylamine (0.115 ml) and 2.5M n-butyllithium in hexane (0.33 ml) at 0° C.]. Dimethylaminocarbonyl chloride (0.06 ml) was then added and the reaction mixture was stirred at 0° C. for 1 hour and then maintained at room temperature for 18 hours. The mixture was diluted with ethyl acetate (20 ml) and water (10 ml) and the organic layer was separated and dried (sodium sulfate). The solvent was evaporated in vacuo and the residue was chromatographed on a silica gel flash column eluting with hexane:ethyl acetate (2:1) to give the title compound (0.171 g).

δ ($^1$H, CDCl$_3$): 9.71 (s, 1H, CHO), 7.43 to 7.26 (m,15H, 3×Ph), 6.96 (s, 1H, Ph$_2$CH), 5.97 (dd, 1H, H-2, J=1.5 and 3.6 Hz), 5.35 (dd, 1H, H-2', J=3.0 and 4.8 Hz), 5.17 (m, 2H, PhCH$_2$OCO), 4.98 (dd, 1H, H-3', J=1.5 and 4.8 Hz), 4.61 (d, 1H, H-1', J=1.8 Hz), 3.97 (d, 1H, 8aCH$_2$, J$_{AB}$=9.0 Hz), 3.75 (m, 1H, H-5'), 3.66 (d, 1H, 8aCH$_2$, J$_{AB}$=9.0 Hz), 3.36 (s, 3H, OMe), 3.25 (dd, 1H, H4', J=5.1 and 3.0 Hz), 2.93 (s, 3H, CH$_3$N), 2.91 (s, 3H, CH$_3$N), 2.58 (m, 1 H, H-1).

INTERMEDIATE 52

(a) [1R-(1α, 3aβ, 4β, 4aβ, 7β, 7aα, 8aβ)] 8a-[(2,3,6,-Trideoxy-2,3-didehydro-4-O-methyl-β-D-allopyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester and (b) [1R-(1α, 3aβ, 4β, 4aβ, 7β7aα, 8aβ)] 8a-[(3,6-Dideoxy-3-iodo-4-O-methyl-β-altro and mannopyranosyloxy) methyl]-4-formyl-4,4a,5,6,7,7a,8,8a-octahydro-7-methyl-3-(1-methylethyl)-1,4-methano-s-indacene-3a(1H)-carboxylic acid, diphenylmethyl esters Intermediate 1 (1.5 g), triphenylphosphine (2.4 g) and imidazole (640 mg) were refluxed in toluene (50 ml) with stirring and zinc (40 mg) was added. Then, iodine (1.75 g) was added in small portions. The reaction mixture was refluxed for 4 hours, cooled, decanted into 10% aqueous sodium hydrogen carbonate (50 ml) and 5% aqueous sodium thiosulfate (20 ml) and then shaken until the iodine was consumed. The toluene phase was extracted with water, dried over sodium sulfate and concentrated. The residue was purified by flash column chromatography eluting with hexane:ethyl acetate (10:1 to 6:1) to afford title compound (a) with the higher Rf as a colourless syrup (185 mg) and title compound (b) (as a mixture of 3'-iodo isomers) with the lower Rf as a pale yellow foam (375 mg).

(a) δ ($^1$H, CDCl$_3$): 9.73 (s, 1H, CHO), 7.24–7.45 (m, 10H, 2Ph), 6.99 (s, 1H, CHPh$_2$), 6.01–6.09 (m, 2H, H-2 and H-3'), 4.97 (dd, 1H, H-1', J=1.8 and 3.6 Hz), 3.74 and 4.00 (2d, 2H, 8aCH$_2$, J=9.3 Hz), 3.64 (m, 1H, H-5'), 3.49 (m, 1H, H4'), 3.40 (s, 3H, 4'—OCH$_3$).

(b) δ ($^1$H, CDCl$_3$): 9.73 (s, 1H, CHO), 7.26–7.45 (m, 10H, 2Ph), 6.98 and 6.99 (2s, 1H, CHPh$_2$ of both isomers), 6.03 and 6.08 (2dd, 1H, H-2 of both isomers), 4.35 and 4.99 (2s, 1H, H-1' of each isomer), 4.75 (t, 1H, H-3' of isomer B), 4.14 (m, 1H, H-2' of isomer B), 4.06 (m, 1H, Ha-8aCH$_2$ of both isomers and 1H, H3' of isomer A), 3.75 (m, 1H, Hb-8aCH$_2$ of both isomers), 3.72 (m, 1H, H-5' of isomer B), 3.34 and 3.56 (2s, 3H, 4'—OCH$_3$), 3.30 (m, 2H, H-4' and H-5' of isomer A), 2.57 (m, 1H, H4' of isomer B).

INTERMEDIATE 53

[1R-(1α, 3aβ, 4β, 4aβ, 7β, 7aα, 8aβ)] 8a-[(3,6-Dideoxy-4-O-methyl-β-D-altropyranosyloxy)methyl]-formyl-4,4a,5,6, 7,7a,8,8a-octahydro-7-methyl-3-(1-methylethyl)-1,4-methano-s-indacene-3a(1H)-carboxylic acid, diphenylmethyl ester To a degassed solution of Intermediate 52(b) (115 mg) in toluene (15 ml) under nitrogen, tributyltin hydride (0.08 ml) and azobis(isobutyronitrile) (15 mg) were added. After 1 hour under reflux, the solvent was removed in vacuo to give a syrup, which was purified by flash chromatography eluting with hexane:ethyl acetate (6:1) to yield the title compound (62 mg).

δ ($^1$H, CDCl$_3$): 9.74 (s, 1H, CHO), 7.26–7.44 (m, 10H, 2Ph), 6.99 (s, 1H, CHPh$_2$), 6.04 (dd, 1 H, H-2, J=1.2 and 3.3 Hz), 4.32 (d, 1H, H-1', J=1.2 Hz), 3.76 and 4.08 (2d, 2H, 8aCH$_2$, J=9 Hz), 3.87 (m, 1H, H-2'), 3.36 (s, 3H, 4'—O—CH$_3$), 3.34 (m, 1H, H-5'), 3.21 (dq, 1H, H4', J=13.2 and 4.5 Hz), 2.74 (t, 1H, H-1, J=3.6 Hz), 2.38–2.45 (m, 1H, H-3'a), 2.23 (m, 2H, CHMe$_2$ and 2'—OH).

INTERMEDIATE 54

[1R-(1α, 3aβ, 4b, 4aβ, 7β, 7aα, 8aβ)] 8a-(((2,3,6-Trideoxy-4-O-acetyl-3-acetylthio-β-D-allopyranosyl)oxy)methyl)-4-formyl-4,4a,5,6,7,7a,8,8a-octahydro-7-methyl-3-(1-methylethyl)-1,4-methano-s-indacene-3a(1H)-carboxylic acid, diphenylmethyl ester Cesium thioacetate (1.4 mmol) was prepared in situ, by addition of cesium carbonate (494 mg) to a solution of thioacetic acid (0.1 ml) in dry methanol (5 ml). After 30 minutes, the solvent was stripped off and the crude product was dissolved in dry dimethylformamide (5 ml). The intermediate 21 (500 mg) was added to this solution, dissolved in 3 ml of dimethylformamide. The reaction mixture was stirred at room temperature for 2 days, and after this time, the solvent was evaporated in vacuo, and the crude product purified by flash column chromatography on silica gel, eluting with hexane:ethyl acetate 3:1 to give pure title compound (100 mg).

δ ($^1$H, CDCl$_3$): 9.73 (s, 1H, CHO), 7.33 (m, 10H, 2Ph), 6.98 (s, 1H, CH—Ph$_2$), 6.05 (d, 1 H, H-2, J=2.4 Hz), 4.75 (dd, 1H, H-1', J=8.1 and 3.9 Hz), 4.43 (dd, 1H, H-3', J=5.1 and 3.9 Hz), 4.31 (dd, 1H, H4', J=8.7 and 4.5 Hz), 3.99 (d, 1H, H-8a, J=9.3 Hz), 3.72 (dq, 1H, H-5', J=8.1 and 6.0 Hz), 3.67 (d, 1H, H-8a, J=9.3 Hz), 2.72 (t, 1H, H-1, J=3.9 Hz), 2.35 (s, 3H$_3$), 2.24 (m, 1H, —CH(CH$_3$)$_2$), 2.00 (s, 3H, CH$_3$).

INTERMEDIATE 55

[1R-(1α, 3aβ, 4b, 4aβ, 7β, 7aα, 8aβ)] 8a-[(3-)-benzoyl-2,6-dideoxy-4-O-methyl-β-allopyranosyloxy) methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester Intermediate 10 (200 mg) and dimethylaminopyridine (126 mg) were solved in 20 ml of dry dichloromethane. Benzoyl chloride (146 mg) in 5 ml of dry dichloromethane was added dropwise and the reaction mixture was refluxed for 6 hours. The mixture of reaction was washed with a saturated solution of sodium bicarbonate (50 ml), water (50 ml) and brine (50 ml), dried over magnesium sulphate and evaporated to dryness. The residue was chromatographied with mixtues of hexane:ethyl acetate to give the title compound (180 mg, 78% yield) as a white foam.

δ (1H, CDCl$_3$): 9.72 (s, 1H, CHO), 8.07, 7.6-7.2 (dd, m, 2H, 13H, Ph—CO+, PL2—CH), 6.99 (s, 1H, Ph$_2$CH), 6.02 (dd, 1H, H-2, J-3.6 and 1.9 Hz), 5.7 (c, 1H, H-3'), 4.7 (dd, 1H, H-1'), 4.04, 3.71 (dd, 1H, 1H, 8aCH$_2$, 8bCH$_2$, J=10 Hz), 3.9-3.8 (m, 1H, H-5'), 3.36 (s, 3H, OCH$_3$), 3.04 (dd, 1H, H4', J=3.6 and 7.5 Hz), 2.7 (t, 1H, H-1).

INTERMEDIATE 56

[1R-(1α, 3aβ, 4b, 4aβ, 7β, 7aα, 8aβ)] 8a-[(3-O-acetyl-2,6-dideoxy-4-O-methyl-β-allopyranosyloxy) methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester Intermediate 10 (150 mg), acetic anhydre (0.12 ml, 120 mg) and dimethylaminopyridine (141 mg) were solved in dry dichloromethane (25 ml) and stirred overnight at room temperature under nitrogen atmosphere. The solvent was eliminated and the residue purified by flash chromatography with hexane:ethyl acetate 9:1, to give the title compound (140 mg, 85% yield) as a white foam.

δ ($^1$H, CDCl$_3$): 9.74 (s, 1H, CHO), 7.45, 7.24 (m, 10H, (Ph)$_2$CH)), 6.98 (s, 1H, (Ph)$_2$CH)), 6.05 (dd, 1H, H-2, J=1.8 and 2.16 Hz), 5.51 (c, 1H, H-3'), 4.55 (dd, 1H, H-1', J=0.6 and 7.2 Hz), 4.02, 3.6 (d, d, 1H, 1H, 8aCH$_2$, J=10.8 Hz), 3.72 (m, 1H, H-5'), 3.34 (s, 3H, OCH$_3$), 2.90 (dd, 1H, H4'), 2.73 (t, 1H, H-1), 2.11 (s, 3H, CH$_3$CO).

EXAMPLE 1

[1R-(1α, 3aβ, 4β, 4aβ, 7β, 7aα, 8aβ)] 8a-[(6-Deoxy-4-O-methyl-3-O-(3-phenylprop-2(E)-enyl)-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid A solution of sordarin (1 mmol) in dry tetrahydrofuran (20 ml) under nitrogen was treated with sodium hydride (3.8 mmol). After 30 minutes, a solution of cinnamyl bromide (1.1 mmol) in dry tetrahydrofuran (5 ml) was added. The mixture was stirred for 3 days, and then diluted with ethyl acetate and washed with water. The organic phase was evaporated and the residue purified by flash chromatography eluting with dichloromethane:methanol (30:1) to give the title compound (73 mg).

δ ($^1$H, CDCl$_3$): 9.80 (s, 1H, CHO), 7.33 (m, 5H, Ph), 6.58 (d, 1H, H-3", J=15.9 Hz), 6.31 (m, 1H, H-2"), 6.00 (dd, 1H, H-2, J=1.2 and 3.3 Hz), 4.66 (d, 1H, H-1', J=1.2 Hz), 4.36 (m, 2H, CH$_2$—1"), 4.24 and 3.47 (d,d 1H, 1H, 8a-CH$_2$, J=9.3 Hz), 4.17 (t, 1H, H-3', J=3.9 Hz), 3.68 (m, 1H, H-2'), 3.65 (m, 1H, H-5'), 3.19 (dd, 1H, H4', J=3.3 and 9.3 Hz); δ ($^{13}$C, CDCl$_3$): 204.7 (CHO), 175.1 (CO$_2$H), 148.3 (C-3), 136.6, 133.0, 128.6, 128.5, 127.7, 126.5 and 126.2 (Ph, C-2" and C-3"), 130.4 (C-2), 98.8 (C-1'), 80.0 (C-4'), 75.8 (C-5'), 74.3 (8a-CH$_2$), 73.3 (C-3a), 73.0 (C-2"), 68.5 (C-3'), 66.5 (C-2').

EXAMPLE 2

[1R-(1α, 3aβ, 4β, 4aβ, 7β, 7aα, 8aβ)] 8a-[(3-O-Benzyl-6-deoxy-4-O-methyl-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid A stirred solution of Intermediate 2 (0.3mmol) in water (3 ml) at 0° C. was treated with trifluoroacetic acid (7 ml). The mixture was stirred for 30 minutes and then poured into water:ether (1:1; 50 ml). The organic phase was evaporated and the residue purified by flash chromatography using dichloromethane:methanol (20:1) as eluent to give the title compound (115 mg).

δ ($^1$H, CDCl$_3$): 9.81 (s, 1H, CHO), 7.36 (m, 5H, Ph), 6.03 (dd, 1H, H-2, J=1.2 and 3.6 Hz), 4.86 and 4.59 (AB system, 1H, 1H, CH$_2$Ph, J=12.6 Hz), 4.66 (d, 1H, H-1', J=0.9 Hz), 4.21 and 3.50 (d,d, 1H, 1H, 8a-CH$_2$, J=9 Hz), 4.05 (t, 1H, H-3', J=3.6 Hz), 3.65 (m, 2H, H-2' and H-5'), 3.19 (dd, 1H, H-4', J=3.3 and 9.3 Hz), 2.57 (t, 1H, H-1, J=3.6 Hz), 2.32 (m, 1H, CH(CH$_3$)$_2$); δ ($^{13}$C, CDCl$_3$): 204.7 (CHO), 175.1 (CO$_2$H), 148.4 (C-3), 138.2 (Cipso), 130.3 (C-2), 128.2, 127.9, 127.6 (Ph), 98.7 (C-1'), 79.8 (C-4'), 75.8 (C-5'), 74.3 and 74.1 (8a-CH$_2$ and CH$_2$Ph), 65.6 (C-8a), 66.3 (C-3'), 65.3 (C-2'), 57.3 (OCH$_3$).

EXAMPLE 3

[1R-(1α, 3aβ, 4β4aβ, 7β, 7aα, 8aβ)] 8a-[(6-Deoxy-3-O-hexyl-4-O-methyl-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid To a solution of Intermediate 3 (0.14 mmol) in methanol (20 ml) was added 10% palladium on charcoal (20 mg) under nitrogen. The mixture was shaken in a Parr apparatus under 6 psi of hydrogen for 30 minutes at room temperature. The catalyst was filtered off and the solvent evaporated to dryness. The residue was purified by flash chromatography using dichloromethane:methanol (25:1) as eluent to give the title compound (64 mg).

δ ($^1$H, CDCl$_3$): 9.83 (s, 1H, CHO), 6.03 (d, 1H, H-2, J=3 Hz), 4.64 (d, 1H, H-1', J=1.2 H), 4.28 and 3.41 (d,d, 1H, 1H, 8a-CH$_2$, J=9.3 Hz), 4.14 (t, 1H, H-3', J=3.6 Hz), 3.64 (m, 2H, H-2' and H-5'), 3.52 (m, 2H, OCH$_2$CH$_2$), 3.15 (dd, 1H, H4', J=3 and 9.3 Hz), 2.52 (m, 1H, H-1), 2.31 (m, 11H, CH(CH$_3$)$_2$); δ ($^{13}$C, CDCl$_3$): 204.7 (CHO), 174.3 (CO$_2$H), 148.7 (C-3), 130.2 (C-2), 98.4 (C-1'), 80.0 (C-4'), 76.9 (C-5'), 73.9 (8a-CH$_2$), 72.9 (OCH$_2$CH$_2$), 68.5 (C-3'), 66.3 (C-2'), 65.0 (C-8a), 59.0 (OCH$_3$).

EXAMPLE 4

[1R-(1α, 3aβ, 4β, 4aβ, 7β, 7aα, 8aβ)] 8a-[(6-Deoxy-2,3,4-tri-O-methyl-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid To a solution of Intermediate 4 (0.26 mmol) in methanol (20ml) was added 10% palladium on charcoal (20 mg) under nitrogen. The mixture was shaken in a Parr apparatus under 8 psi of hydrogen for 30 minutes at room temperature. The catalyst was filtered off and the solvent evaporated to dryness. The residue was purified by flash chromatography using dichloromethane:methanol (20:1) as eluent to give the title compound (98 mg).

δ ($^1$H, CDCl$_3$): 9.85 (s, 1H, CHO), 6.04 (dd, 1H, H-2, J=1.2 and 3.3 Hz), 4.60 (d, 1H, H-1', J=1.5 Hz), 4.33 (d, 1H, 8a-CHa, J=9.3 Hz), 3.71 (m, 2H, H-2', and H-3'), 3.52 (s, 3H, 2'—OCH$_3$), 3.50 (s, 3H, 3'—OCH$_3$), 3.41 (m, 5H, 4'—OCH$_3$, H-5' and 8a-CHb), 3.16 (dd, 1H, H-4', J=3 and 9.3 Hz), 2.50 (t, 1H, H-1, J=3.9 Hz), 2.32 (m, 1H, CH(CH$_3$)$_2$).

EXAMPLE 5

[1R-(1α, 3aβ, 4β, 4aβ, 7β, 7aα, 8aβ)] 8a-[(2,6-Dideoxy-3,4-O-dimethyl-β-D-allopyranosyloxy)methyl]-4-formyl-4,4a,5,6,7,7a,8,8a-octahydro-7-methyl-3-(1-methylethyl)-1,4-methano-s-indacene-3a(1H)-carboxylic acid Sodium hydride (24 mg) was added portionwise to a solution of Intermediate 10 (150 mg) in anhydrous tetrahydrofuran (3 ml) under nitrogen atmosphere at 0° C. The resulting suspension was stirred for 15 minutes and methyl iodide (125 μl) was added. After 2 hours of stirring 1N ammonium chloride (10 ml) and ethyl acetate (20 ml) were added. The aqueous phase was extracted with ethyl acetate (2×20 ml) and the organic phase was washed with brine, dried (magnesium sulphate) and evaporated to dryness. The residue was dissolved in ethyl acetate (10 ml) and 10% palladium on charcoal (100 mg) was added. The mixture was stirred under 30 psi of hydrogen for 45 minutes. The catalyst was filtered off and the residue flash chromatographed eluting with dichloromethane:methanol (30:1) to obtain the title compound (78 mg).

δ ($^1$H, CDCl$_3$): 9.86 (s, 1H, CHO), 6.04 (dd, 1H, H-2, J=1.5 and 3.6 Hz), 4.65 (dd, 1 H, H-1', J=1.8 and 9.6 Hz), 4.41 (d, 1H, 8a-CH$_2$, J=9.3 Hz), 3.83-3.70 (m, 2H, H-3' and H-4'), 3.44 (s, 3H, CH$_3$O), 3.39 (s, 3H, CH$_3$O), 3.30 (d, 1H, 8aCH$_2$, J=9.3 Hz), 2.85 (dd, 1H, H-4', J=3.9 and 9.3 Hz), 2.45 (t, 1H, H-1, J=3.6 Hz); δ ($^1$H, CDCl$_3$): 204.5 (CHO), 173.8 (CO$_2$H), 184.4 (C-3), 130.5 (C-2), 97.5 (C-1'), 82.4 (C-4'), 73.3 (8aCH$_2$), 73.0 (C-3'), 69.5 (C-5'), 65.0 (C8a), 59.0 (C-4), 57.8 (CH$_3$O), 57.1 (CH$_3$O).

EXAMPLE 6

[1R-(1α, 3aβ, 4β, 4aβ, 7β, 7aα, 8aβ)] 8a-[(2,6-Dideoxy-3-O-ethyl-4-O-methyl-62-D-allopyranosyloxy)methyl]-4-formyl-4,4a,5,6,7,7a,8,8a-octahydro-7-methyl-3-(1-methylethyl)-1,4-methano-s-indacene-3a(1H)-carboxylic acid Sodium hydride (24 mg) was added portionwise to a solution of Intermediate 10 in anhydrous tetrahydrofuran under nitrogen atmosphere at 0° C. The resulting suspension was stirred for 15 minutes and ethyl iodide (160 μl) was added. After 2 hours of stirring 1N ammonium chloride (10 ml) and ethyl acetate (20 ml) were added. The aqueous phase was extracted with ethyl acetate (2×20 ml) and the organic phase was washed with brine, dried (magnesium sulphate) and evaporated to dryness. The residue was dissolved in ethyl acetate (10 ml) and 10% palladium on charcoal (100 mg) was added. The mixture was stirred under 30 psi of hydrogen for 45 minutes. The catalyst was filtered off and the residue flash chromatographed eluting with dichloromethane:methanol (30:1) to obtain the title compound (57 mg).

δ ($^1$H, CDCl$_3$): 9.88 (s, 1H, CHO), 6.04 (dd, 1H, H-2, J=1.5 and 3.6 Hz), 4.69 (dd, 1H, H-1', J=2.1 and 9.6 Hz), 4.46 (d, 1H, 8aCH$_2$, J=9.3 Hz), 3.93-3.90 (m, 1H, H-3'), 3.81 (dq, 1H, H4', J$_d$=9.6 Hz, J$_q$=6.6 Hz), 3.61 (t, 2H, 3'—O—CH$_2$, J=7.2 Hz), 3.75 (s, 3H, 4—O—CH$_3$), 3.29 (d, 1H, 8aCH$_2$, J=9.3 Hz), 2.84 (dd, 1H, H4', J=3.3 and 9.6 Hz), 2.43 (t, 1H, H-1, J=3.9 Hz); δ ($^{13}$C, CDCl$_3$): 204.5 (CHO), 173.6 (CO$_2$H), 148.5 (C-3), 130.4 (C-2), 97.7 (C-1'), 82.5 (C-4'), 74.9 (C3a), 73.1 (8aCH$_2$), 70.9 (C-3'), 69.4 (C-4'), 65.4 (C8a), 64.9 (3'—O—CH$_2$), 59.0 (C-4), 57.1 (4'—O—CH$_3$).

EXAMPLE 7

[1R-(1α, 3aβ, 4β, 4aβ, 7β, 7aα, 8aβ)] 8a-[(2,6-Dideoxy-4-O-3-O-propyl-β-D-alopyranosyloxy)methyl]-4-formyl-4,4a,5,6,7,7a,8,8a-octahydro-7-methyl-3-(1-methylethyl)-1,4-methano-s-indacene-3a(1H)-carboxylic acid Sodium hydride (24 mg) was added portionwise to a solution of Intermediate 10 (142 mg) in anhydrous tetrahydrofuran (5 ml) under nitrogen atmosphere at 0° C. The resulting suspension was stirred for 15 minutes and allyl bromide (173 μl) was added. After 2 hours of stirring 1N ammonium chloride (10 ml) and ethyl acetate (20 ml) were added. The aqueous phase was extracted with ethyl acetate (2×20 ml) and the organic phase was washed with brine, dried (magnesium sulphate) and evaporated to dryness. The residue was dissolved in ethyl acetate (10 ml) and 10% palladium on charcoal (100 mg) was added. The mixture was stirred under 30 psi of hydrogen for 45 minutes. The catalyst was filtered off and the residue flash chromatographed eluting with dichloromethane:methanol (30:1) to obtain the title compound (90 mg).

δ ($^1$H, CDCl$_3$): 9.87 (s, 1H, CHO), 6.04 (dd, 1H, H-2, J=1.5 and 3.6 Hz), 4.68 (dd, 1H, H-1', J=2.1 and 9.6 Hz), 4.44 (d, 1H, 8aCH$_2$, J=9.6 Hz), 3.93-3.85 (m, 1H, H-3'), 3.81 (dq, 1H, H-5', J$_d$=9.3 Hz and J$_q$=6.3 Hz), 3.49 (t, 2H, 3'—O—CH$_2$, J=6.6 Hz), 3.70 (s, 3H, 4'—O—CH$_3$), 3.29 (d, 1H, 8aCH$_2$, J=9.6 Hz), 2.84 (dd, 1H, H4', J=2.7 and 9.3 Hz), 2.43 (t, 1H, H-1, J=4.2 Hz); δ ($^{13}$C, CDCl$_3$): 204.5 (CHO), 173.6 (CO$_2$H), 148.5 (C-3), 130.4 (C-2), 97.8

(C-1'), 82.6 (C4'), 74.8 (C3a), 73.2 (8a-CH$_2$), 71.8 (3'—O—CH$_2$), 71.0 (C-3'), 69.4 (C-5'), 65.0 (C-8a), 59.0 (C-4), 57.0 (4—O—CH$_3$).

EXAMPLE 8

[1R-(1α, 3aβ, 4β, 4aβ, 7β, 7aα, 8aβ)] 8a-[(2,6-Dideoxy-4-O-methyl-3-O-methyloxymethyl-β-D-allopyranosyloxy)methyl]-4-formyl-4,4a,5,6,7,7a,8,8a-octahydro-7-methyl-3-(1-methylethyl)-1,4-methano-s-indacene-3a(1H)-carboxylic acid To a solution of Intermediate 11 (180 mg) in ethyl acetate (20 ml) was added 10% palladium on charcoal (100 mg) under nitrogen. The mixture was shaken in a Parr apparatus under 20 psi of hydrogen for 40 minutes at room temperature. The catalyst was filtered off and the solvent evaporated to dryness. The residue was purified by flash column chromatography on silica gel eluting with methylene chloride:methanol (20:1) to give the title compound (100 mg).

δ ($^1$H, CDCl$_3$): 9.83 (s, 1H, CHO), 6.04 (dd, 1H, H-2, J=1.2 and 3.3 Hz), 4.72 (AB system, 2H, OCH$_2$OCH$_3$, J$_{AB}$=6.9 Hz), 4.68 (dd, 1H, H-1', J=2.1 and 9 Hz), 4.33 and 3.36 (2d, 2H, 8a-CH$_2$, J=9.6 Hz), 4.21 (m, 1H, H-3'), 3.79 (m, 1H, H-5'), 3.39 (s, 3H, OCH$_3$), 3.38 (s, 3H, OCH$_3$), 2.84 (dd, 1H H4', J=2.7 and 9.3 Hz), 2.49 (t, 1H, H-1); δ ($^{13}$C, CDCl$_3$): 204.5 (CHO), 173.8 (COOH), 148.4 (C-3), 130.4 (C-2), 97.8 (C-1'), 95.9 (OCH$_2$OCH$_3$), 82.4 (C4'), 73.3 (8a-CH$_2$), 69.2 (C-3'), 68.8 (C-5'), 65.0 (C-8a), 57.3 (OCH$_2$OCH$_3$), 55.5 (C-7), 47.2 (C-1), 41.6 (C4), 35.8 (C-2'), 18.0 (C6').

EXAMPLE 9

[1R-(1α, 3aβ, 4β, 4aβ, 7β, 7aα, 8aβ)] 8a-[(2,6-Dideoxy-3-O-methyl-4-O-propyl-β-D-allopyranosyloxy)methyl]-4-formyl-4,4a,5,6,7,7a,8,8a-octahydro-7-methyl-3-(1-methylethyl)-1,4-methano-s-indacene-3a(1H)-carboxylic acid To a solution of the 3-O-methyl compound from Intermediate 10 (120 mg) in dry tetrahydrofuran (20 ml) at 0∨ C. was added sodium hydride (9 mg). The suspension was stirred for 0.5 hours and allyl bromide (10 equivalents) and a catalytic amount of tetrabutylammonium iodide were added. The mixture was stirred for 2 days at room temperature. The reaction was quenched with 1N ammonium chloride and the mixture extracted with ethyl acetate. The organic layer was concentrated to 15 ml and 10% palladium on charcoal was added (100 mg) under nitrogen. The mixture was shaken in a Parr apparatus under 15 psi of hydrogen for 30 minutes at room temperature. The catalyst was filtered off and the solvent evaporated to dryness. The residue was purified by flash column chromatography on silica gel eluting with methylene chloride:methanol (20:1) to give the title compound (60 mg).

δ ($^1$H, CDCl$_3$): 9.86 (s, 1H, CHO), 6.04 (dd, 1H, H-2, J=0.9 and 3.0 Hz), 4.65 (dd, 1H, H-1, J=2.1 and 9.9 Hz), 4.42 and 3.80 (2d, 2H, 8a-CH$_2$, J=9.6 Hz), 3.76 (m, 1H, H-3'), 3.60-3.50 (m, 1H, H5'), 3.45 (s, 3H, OCH3), 3.38 -3.27 (m, 2H, OCH$_2$CH$_2$CH$_3$), 2.93 (dd, 1H, H-4', J=2.8 and 9.6 Hz), 2.44 (t, 1H, H-1); δ ($^{13}$C, CDCl$_3$): 204.5 (CHO), 173.2 (COOH), 148.5 (C-3), 130.3 (C-2), 97.5 (C-1'), 81.2 (C-4'), 73.8 (C-3'), 69.4 (C-5'), 64.9 (C-8a), 34.4 (C-2), 18.0 (C-6').

EXAMPLE 10

[1R-(1α, 3aβ, 4β, 4aβ, 7β, 7aα, 8aβ)] 8a-[(3-Azido-3,6-dideoxy-4-O-methylβ-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid A stirred solution of Intermediate 16 (0.29 mmol) in water (4 ml) at 0° C. was treated with trifluoroacetic acid (6 ml). After 90 minutes, the mixture was poured into ether:water (1:1; 50 ml). The organic phase was evaporated and the residue purified by flash column chromatography using dichloromethane:methanol (50:1) as eluent to give the title compound (98 mg).

δ ($^1$H, CDCl$_3$): 9.68 (s, 1H, CHO), 6.07 (dd, 1H, H-2, J-=1.2 and 3.3 Hz), 4.52 (d, 1H, H1', J=1.2 Hz), 4.18 (t, 1H, H-2', J=4.2 Hz), 4.02 and 3.65 (m,m, 1H, 1H, 8a-CH$_2$), 3.78 (m, 2H, H-3' and H-5'), 3.46 (s, 3H, OCH$_3$), 3.37 (dd, 1H, H4', J=3.3 and 8.7 Hz), 2.67 (sbr, 1H, OH), 2.34 (m, 1H, CH(CH$_3$)$_2$); δ ($^{13}$C, CDCl$_3$): 204.9 (CHO), 130.5 (C-2), 97.8 (C-1'), 79.8, 69.7, 69.4 and 59.2 (C-2', C-3', C-4' and C-5'), 74.4 (8a-CH$_2$), 65.6 (C-8a).

EXAMPLE 11

[1R-(1α, 3aβ, 4β, 4aβ, 7β, 7aα, 8aβ)] 8a-[(3,6-Dideoxy-4-O-methyl-3-methylthio-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid A stirred solution of Intermediate 17 (0.2 mmol) in water (4 ml) at 0° C. was treated with trifluoroacetic acid (6 ml). After 90 minutes, the mixture was poured into ether:water (1:1; 50 ml). The organic phase was evaporated and the residue purified by flash column chromatography using dichloromethane:methanol (50:1) as eluent to give the title compound (68 mg).

δ ($^1$H, CDCl$_3$): 9.73 (s, 1H, CHO), 6.08 (dd,1H, H-2, J=1.2 and 3.3 Hz), 4.74 (d, 1H, H-1', J=1.5 Hz), 4.09 and 3.64 (d,d, 1H, 1H, 8a-CH$_2$, J=9.6 Hz), 3.96 ((dd, 1H, H-2', J=1.2 and 4.2 Hz), 3.72 (m, 1H, H-5'), 3.45 (dd, 1 H, H-4', J=4.2 and 8.1 Hz), 3.40 (s, 3H, OCH$_3$), 3.33 (t, 1H, H-3', J=4.2 Hz), 2.66 (t, 1H, H-1, J=3.9 Hz), 2.34 (m, 1H, CH(CH$_3$)$_2$); δ ($^{13}$C, CDCl$_3$): 204.5 (CHO), 176.6 (CO$_2$H), 148.2 (C-3), 130.7 (C-2), 97.8 (C-1'), 79.5, 70.9, 70.4 and 57.4 (C-2', C-3', C4' and C-5'), 74.0 (8a-CH$_2$), 72.3 (C-3a), 65.6 (C-8a), 58.8 (C-4).

EXAMPLE 12

[1R-(1α, 3aβ, 4β, 4aβ, 7β, 7aα, 8aβ)] 8a-[(3-Azido-3,6-dideoxy-4-O-methyl-β-D-glucopyranosyloxy)methyl]-4-formyl-4,4a,5,6,7,7a,8,8a-octahydro-7-methyl-3-(1-methylethyl)-1,4-methano-s-indacene-3a(1H)-carboxylic acid A stirred solution of Intermediate 18 (0.37 mmol) in water (4 ml) at 0° C. was treated with trifluoroacetic acid (6 ml). After 90 minutes, the mixture was poured into ether:water (1:1; 50 ml). The organic phase was evaporated and the residue purified by flash column chromatography using dichloromethane:methanol (50:1) as eluent to give the title compound (119 mg).

δ ($^1$H, CDCl$_3$): 9.71 (s, 1H, CHO), 6.04 (dd, 1H,H-2, J=1.2 and 3.3 Hz), 4.07 (d, 1H, H-1', J=7.5 Hz), 3.99 and 3.66 (d,d, 1H, 1H, 8a-CH$_2$, J=9.6 Hz), 3.55 (s, 3H, OCH$_3$), 3.30 (m, 3H, H-2', H-3' and H-5'), 2.71 (m, 3H, H4', H-1 and 2'—OH), 2.31 (m, 1H, CH(CH$_3$)$_2$); δ ($^{13}$C, CDCl$_3$): 204.9 (CHO), 174.3 (CO$_2$H), 148.6 (C-3), 130.3 (C-2), 102.7 (C-1') 84.2, 72.9, 72.2 and 67.7 (C-2', C-3', C4' and C-5'), 75.2 (8a-CH$_2$).

EXAMPLE 13

[1R-(1α, 3aβ, 4β, 4aβ, 7β, 7aα, 8aβ)] 8a-[(3,6-Dideoxy-4-O-methyl-3-methylthio-β-D-glucopyranosyloxy)methyl]-4-formyl-4,4a,5,6,7,7a,8,8a-octahydro-7-methyl-3-(1-methylethyl)-1,4-methano-s-indacene-3a(1H)-carboxylic acid A stirred solution of Intermediate 19 (0.17 mmol) in water (4 ml) at 0° C. was treated with trifluoroacetic acid (6 ml). After 90 minutes, the mixture was poured into ether:water (1:1; 50 ml). The organic phase was evaporated and the residue purified by flash column chromatography using dichloromethane:methanol (50:1) as eluent to give the title compound (69 mg).

δ ($^1$H, CDCl$_3$): 9.74 (s, 1H, CHO), 6.09 (dd, 1H, H-2, J=1.2 and 3.3 Hz), 4.14 (m, 2H, H-1' and 8a-CHa), 3.62 (m, 4H, 8a-CHb and OCH$_3$), 3.33 (m, 1H, H-5'), 3.24 (dd, 1H, H-2', J=7.5 and 10.8 Hz), 2.80 (dd, 1H, H4, J=9 and 10.2 Hz), 2.71 (t, 1H, H-1, J=3.6 Hz), 2.48 (t, 1H, H-3', J=10.5 Hz), 2.33 (m, 1H1, CH(CH$_3$)$_2$), 2.20 (s, 3H, SCH$_3$); δ ($^{13}$C, CDCl$_3$): 204.7 (CHO), 175.8 (CO$_2$H), 148.3 (C-3), 130.7 (C-2), 103.7 ( C-1'), 83.2 (OCH$_3$), 74.7 (C-3a), 74.3, 70.9, 60.8 and 55.3 (C-2', C-3', C4' and C-5'), 73.0 (8a-CH$_2$), 65.6 (C-8a), 59.0 (C-4).

EXAMPLE 14

[1R-(1α, 3aβ, 4β, 4aβ, 7β, 7aα, 8aβ)] 8a-[(3-Acetylamino-3,6-dideoxy-4-O-methyl-β-D-glucopyranosyloxy)methyl]-4-formyl-4,4a,5,6,7,7a,8,8a-octahydro-7-methyl-3-(1-methylethyl)-1,4-methano-s-indacene-3a(1H)-carboxylic acid A solution of Intermediate 20 (0.26 mmol) and sodium methoxide (0.6 mmol) in dry methanol (3 ml) was stirred for 90 minutes at room temperature. The solvent was evaporated and the residue purified by flash chromatography using dichloromethane:methanol (13:1) as eluent to give the title compound (75 mg).

δ (hu 1H, CDCl$_3$): 9.74 (s, 1H, CHO), 6.09 (m, 2H, H-2 and NH), 4.17 (d, 1H, H-1', J=7.5 Hz), 4.13 (t, 1H, H-3', J=7.2 Hz), 3.87 (m, 1H, H-2'), 3.60 (d, 1H, 8a-CHa, J=9.6 Hz), 3.40 (m, 5H, H-5', 8a-CHb and OCH$_3$), 2.96 (t, 1H, H4', J=9.6 Hz), 2.68 (t, 1H, H-1, J=3.9 Hz), 2.32 (m, 1H, CH(CH$_3$)$_2$), 2.07 (s, 3H, CH$_3$CO); δ ($^{13}$C, CDCl$_3$): 204.7 (CHO), 174.9 (CO$_2$H), 172.5 (CO$_2$CH$_3$), 148.3 (C-3), 130.7 (C-2), 103.6 (C-1'), 82.0 (OCH$_3$), 74.8 (8a-CH$_2$), 73.5, 72.0, 58.8 and 56.7 (C-2', C-3', C-4' and C-5'), 73.2 (C-3a), 65.0 (C-8a), 58.9 (C-4).

EXAMPLE 15

[1R-(1α, 3aβ, 4β, 4aβ, 7β, 7aα, 8aβ)] 8a-[(3-Azido-4-O-methyl-2,3,6-trideoxy-β-D-allopyranosyloxy)methyl]-4-formyl-4,4a,5,6,7,7a,8,8a-octahydro-7-methyl-3-(1-methylethyl)-1,4-methano-s-indacene-3a(1)-carboxylic acid Trifluoroacetic acid (0.1 ml) was added to Intermediate 23 (120 mg) in dichloromethane (10 ml) at 0° C. After being stirred for 40 minutes the mixture was quenched with a 5% aqueous sodium hydrogen carbonate solution to pH7. The organic phase was dried and concentrated to give an oil, which was purified by flash column chromatography eluting with hexane:ethyl acetate (10:1) and dichloromethane:methanol (20:1) afforded the title compound (68 mg) as a white foam.

δ ($^1$H, CDCl$_3$): 9.80 (s, 1H, CHO), 6.05 (dd, 1H, H-2, J=1.2 and 3.6 Hz), 4.55 (dd, 1H, H-1', J=1.8 and 9.3 Hz), 3.41 and 4.22 (m and d, 3H, 8aCH$_2$ and H-3'), 3.75 (dq, 1H, H-5', J=6.3 and 9 Hz), 3.44 (s, 3H, 4'—OMe), 3.00 (dd, 1H, H4', J=3 and 9 Hz); δ ($^{13}$C, CDCl$_3$): 204.5 (CHO), 174 (CO$_2$H), 148 (C-3), 130.6 (C-2), 97.3 (C-1'), 82.6 (C4'), 69.3 (C-5'), 59.1 (C-3'), 57.6 (4'O—CH$_3$), 35.2 (C-2'), 17.9 (C-6').

EXAMPLE 16

[1R-(1α, 3aβ, 4β, 4aβ, 7β, 7aα, 8aβ)] 8a-[(6-Deoxy-4-O-methyl-3-O-(2-tetrahydropyranl)-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid To a solution of Intermediate 25 (0.300 g) in ethyl acetate (20 ml) was added 10% palladium on charcoal (26 mg) under nitrogen. The mixture was shaken in a Parr apparatus under 20 psi of hydrogen for 2 hours at room temperature. The catalyst was filtered off and the solvent evaporated to dryness. The residue was purified on a silica gel flash column eluting with 5% dichloromethane in methanol to afford the title compound (0.027 g) as a 3:2 mixture of diastereomers.

δ (1H, CDCl$_3$) only major diastereomer: 9.75 (s, 1H, CHO), 6.07 (m, 1H, H-1"), 4.74 (m, 1H, H-2), 4.55 (m, 1H, H-1'); δ ($^{13}$C, CDCl$_3$): 206.6 (CHO), 175.9 (CO$_2$H), 150.1 (C-3), 131.6 (C-2), 102.1, 100.5 (C-1"), 98.6 (C-1'), 81.3, 80.6 (C-3', C-4'), 76.4, 76.1 (8aCH$_2$, C-6).

EXAMPLE 17

[1R-(1α, 3aβ, 4β, 4aβ, 7β, 7aα, 8aβ)] 8a-[(2,3,6-Trideoxy-2,3-difluoro-4-O-methyl-β-D-glucopyranosyloxy)methyl]-4-formyl-4,4a,5,6,7,7a,8,8a-octahydro-7-methyl-3-(1-methylethyl)-1,4-methano-s-indacene-3a(1H)-carboxylic acid To a solution of Intermediate 26 (95 mg) in ethyl acetate (25 ml) was added 10% palladium on charcoal (120 mg) under nitrogen. The mixture was shaken in a Parr apparatus under 20 psi of hydrogen for 2 hours. The catalyst was filtered off and a mixture of 2N hydrochloric acid (1 ml) and methanol (5 ml) was added to the filtrate. The mixture was stirred at room temperature for 6 hours and then neutralized with a 5% aqueous sodium hydrogen carbonate solution. The solvent was evaporated to dryness and the residue was flash chromatographed on silica gel eluting with dichloromethane:methanol (20:1) to give the title compound (42 mg) as a white foam.

δ ($^1$H, CDCl$_3$): 9.69 (s, 1H, CHO), 5.87 (dd, 1H, H-2, J=1.2 and 3.6 Hz), 4.58–4.70 and 4.41–4.52 (2m, 1H, H-2', J$_{FH}$=52.8 and 17.1 Hz, J$_{HH}$=8.4 Hz), 4.25 (d, 1H, H-1', J=9 Hz), 4.30–4.40 and 4.10–4.23 (2m, 1H, H-3', J$_{FH}$=52.5 and 14.1 Hz, J$_{HH}$=7.8 and 8.1 Hz), 3.69 and 4.01 (2d, 2H, 8aCH$_2$, J=9.3 Hz), 3.55 (s, 3H, 4'—OCH$_3$), 3.21–3.31 (m, 1H, H-5'), 2.97–3.07 (dq, 1H, H-4', J$_{FH}$=13.2 Hz, J$_{HH}$=8.4 and 8.7 Hz), 2.81 (t, 1H, H-1); δ ($^{13}$C, CDCl$_3$): 204.7 (CHO), 177.1 (CO$_2$), 147.9 (C-3), 131.2 (C-2), 100.0 (dd, C-1', J$_{CF}$=11 and 22 Hz), 96.7 and 97.3 (dd, C-2', J$_{CF}$=18 and 185 Hz), 91.5 and 89.1 (dd, C-3', J$_{CF}$=18 and 189 Hz), 83.0 (dd, C-4', J$_{CF}$=6 and 16 Hz), 75.4 (8aCH$_2$), 72.1 (C-8a), 70.0 (d, C-5', J$_{CF}$=9 Hz), 65.8 (C-3a), 60.6 (4'OMe), 58.4 (C-4).

EXAMPLE 18

[1R-(1α, 3aβ, 4β, 4aβ, 7β, 7aα, 8aβ)] 8a-[(2,3,6-Trideoxy-4-O-methyl-3-oxo-β-D-glucopyranosyloxy)methyl]-4-formyl-4,4a,5,6,7,7a,8,8a-octahydro-7-methyl-3-(1-methylethyl)-1,4-methano-s-indacene-3a(1H)-carboxylic acid To a solution of Intermediate 27 (0.17 mmol) in ethyl acetate (20 ml) was added 10% palladium on charcoal (50 mg) under nitrogen. The mixture was shaken in a Parr apparatus under 20 psi of hydrogen for 1 hour at room temperature. The catalyst was filtered off and the solvent evaporated to dryness. The residue was purified by flash chromatography using dichloromethane:methanol (20:1) as eluent to give the title compound (63 mg).

δ ($^1$H, CDCl$_3$): 9.72 (s, 1H, CHO), 6.06 (dd, 1H, H-2, J=1.2 and 3.3 Hz), 4.48 (dd, 1H, H-1', J=2.7 and 9 Hz), 4.05 and 3.62 (d,d, 1H, 1H, 8a-CH$_2$, J=9 Hz), 3.43 (m, 2H, H-4' and H-5'), 2.65 (m, 3H, CH$_2$—2' and H-1), 2.32 (m, 1H, CH(CH$_3$)$_2$), 1.42 (d, 3H, CH$_3$—6', J=5.7 Hz); δ ($^{13}$C, CDCl$_3$): 204.5 (CHO), 204.0 (CO-3'), 176.6 (CO$_2$H), 148.2 (C-3), 130.8 (C-2), 100.3 (C-1'), 87.0 (C-4'), 74.6 (8a-CH$_2$), 71.4 (C-5'), 48,4 (C-2').

EXAMPLE 19

[1R-(1α, 3aβ, 4β, 4aβ, 7β, 7aα, 8aβ)] 8a-[(3,6-Dideoxy-4-O-methyl-3-oxo-β-D-allopyranosyloxy)methyl]-4-formyl-4,4a,5,6,7,7a,8,8a-octahydro-7-methyl-3-(1-methylethyl)-1,4-methano-s-indacene-3a(1H)-carboxylic acid To a suspension of 10% palladium on charcoal (100 mg) in ethyl acetate (10 ml) was added a solution of Intermediate 28 (141 mg) in ethyl acetate (5 ml) and the mixture was hydrogenated at room temperature under 30 psi of hydrogen for 45 minutes. The catalyst was filtered off and the solvent evaporated to dryness. The residue was flash chromatographed on silica gel eluting with dichloromethane and dichloromethane:methanol (30:1) to obtain the title compound (83 mg).

δ ($^1$H, CDCl$_3$): 9.71 (s, 1H, CHO), 6.11 ( dd, 1H, H-2, J=1.5 and 3.6 Hz), 4.16-4.11 (m, 2H, H-1, H-2'), 3.55 (s, 3H, 4'—O—CH$_3$), 3.57 (dd, 1H, H4', J=1.5 and 9.6 Hz), 3.40 (dq, 1 H, H4', J$_d$=9.6 Hz, J$_q$=6.0 Hz), 2.82 (t, 1H, H-1, J=3.4 Hz); δ ($^{13}$C, CDCl$_3$): 205.0 (CHO), 204.6 (C-3'), 175.6 (CO$_2$H), 148.0 (C-3), 131.2 (C-2), 104.8 (C-1'), 86.1 (C4'), 75.3 (8aCH$_2$), 72.3 (C3a), 71.7 (C-5'), 65.4 (C8a), 59.6 (CH$_3$O).

EXAMPLE 20

[1R-(1α, 3aβ, 4β, 4aβ, 7β, 7aα, 8aβ)] 8a-[(3,6-Dideoxy-4-O-methyl-3-propyloxyimino-β-D-allopyranosyloxy)methyl]-4-formyl-4,4a,5,6,7,7a,8,8a-octahydro-7-methyl-3-(1-methylethyl)-1,4-methano-s-indacene-3a(1H)-carboxylic acid Intermediate 31 (180 mg) was dissolved in ethyl acetate (15 ml) and 10% palladium on charcoal (100 mg) was added. The mixture was stirred under 30 psi of hydrogen atmosphere for 3 hours. The catalyst was filtered off and the solvent evaporated to dryness. The residue was dissolved in tetrahydrofuran (5 ml) and 1N hydrochloric acid (3 ml) was added. The mixture was stirred for 4 hours at room temperature, diluted with water and extracted with ethyl acetate (3×25 ml). The organic phase was washed with brine, dried (magnesium sulphate) and evaporated to dryness. The residue was flash chromatographed on silica gel eluting with dichloromethane and dichloromethane:methanol (30:1) to obtain the title compound (107 mg) as a mixture of Z:E isomers in a 3:1 ratio.

δ ($^1$H, CDCl$_3$) peaks of the major component: 9.75 (s, 1H, CHO), 6.08 (dd, 1H, H-2, J=1.5 and 3.6 Hz), 4.79 (d, 1H, H-1', J=5.1 Hz), 4.59 (dd, 1H, H-2', J=0.6 and 5.1 Hz), 4.17-4.08 (m, 5H, OCH$_2$, H-4', H-5', 8aCH$_2$), 3.55 (d, 1H, 8aCH$_2$, J=9.3 Hz), 3.33 (s, 3H, 4—O—CH$_3$); δ ($^{13}$C, CDCl$_3$) peaks of the major component: 204.6 (CHO), 175.9 (CO$_2$H), 151.1 (C=N), 148.0 (C-3), 130.9 (C-2), 101.9 (C-1), 81.6 (C-4'), 76.3, 76.0 (C3a), 74.9 (C-5'), 74.2 (8aCH$_2$), 65.8 (NOCH$_2$), 65.7 (C8a), 59.0 (CH$_3$O).

EXAMPLE 21

[1R-(1α, 3aβ, 4β, 4aβ, 7β, 7aα, 8aβ)] 8a-[(3-O-Benzoyl-6-deoxy-4-O-methyl-β-D-altropyranosyloxy)methyl]-4-formyl-4,4a,5,6,7,7a,8,8a-octahydro-7-methyl-3-(1-methylethyl)-1,4-methano-s-indacene-3a-(1H)-carboxylic acid To a solution of Intermediate 32 (250 mg) in methanol (30 ml), was added 10% palladium on charcoal (120 mg) under nitrogen. The mixture was shaken in a Parr apparatus under 10 psi of hydrogen for 1.5 hours at room temperature. The catalyst was filtered off and the solvent evaporated to dryness. The residue was purified by flash chromatography eluting with hexane:ethyl acetate (4:1) and dichloromethane:methanol (15:1) to give the title compound (140 mg) as a white foam.

δ ($^1$H, CDCl$_3$): 9.71 (s, 1H, CHO), 8.04 and 7.61-7.43 (2m, 2H and 3H, Ph), 6.05 (dd, 1H, H-2, J=3.3 and 1.2 Hz), 5.72 (dd, 1H, H-3', J=3 and 0.9 Hz), 4.71 (s, 1H, H-1'), 3.72 and 4.06 (2d, 2H, 8aCH$_2$, J=9 Hz), 3.87–3.94 (m, 2H, H-2' and H-5'), 3.38 (s, 3H, 4'—OMe), 3.41 (m, 1H, H-4'), 2.73 (t, 1H, H-1, J=3.9 Hz.); δ ($^{13}$C, CDCl$_3$): 204.8 (CHO), 175.8 (CO$_2$H), 165.3 (CO$_2$ of 3'OBz), 148.2 (C-3), 133.3, 129.6 and 128.4 (CH of Ph), 130.8 (C-2), 129.8 (quartemary of PH), 98.3 (C-1'), 78.3 (C4'), 74.3 (8aCH$_2$), 72.2 (C-3a), 69.8 (C-3'), 69.2 (C-5'), 68.0 (C-2'), 65.6 (C-8a), 58.9 (4'—OMe), 57.7 (C4), 46.1 (C-1).

EXAMPLE 22

[1R-(1α, 3aβ, 4β, 4aβ, 7β, 7aα, 8aβ)] 8a-[(3-O-Benzyloxycarbonyl-6-deoxy-4-O-methyl-β-D-altropyranosyloxy)methyl]-4-formyl-4,4a,5,6,7,7a,8,8a,-octahydro-7-methyl-3-(1-methylethyl)-1,4-methano-s-indacene-3a(1H)-carboxylic acid A stirred solution of Intermediate 33 (0.4 mmol) in water (4 ml) at 0° C. was treated with trifluoroacetic acid (6 ml). After 30 minutes, the solution was poured into water:ether (1:1;50 ml). The organic phase was evaporated and the residue purified by flash column chromatography using hexane:ethyl acetate (1:2) as eluent to give the title compound (143 mg).

δ ($^1$H, CDCl$_3$): 9.69 (s, 1H, CHO), 7.37 (m, 5H, Ph), 6.04 (dd, 1H, H-2, J=1.2 and 3.3 Hz), 5.32 (t, 1H, H-3', J=3.3 Hz), 5.21 and 5.14 (AB sistem, 1H, 1H, CH$_2$Ph, J=11.7 Hz), 4.62 (d, 1H, H-1', J=0.9 Hz), 4.03 and 3.65 (d,d, 1H, 1H, 8a-CH$_2$, J=9 Hz), 3.87 (d, 1H, H-2', J=4.5 Hz), 3.74 (m, 1H, H-5'), 3.28 (dd, 1H, H4', J=3 and 9 Hz), 2.67 (sbr, 1H, H-1), 2.33 (m, 1H, CH(CH$_3$)$_2$); δ ($^{13}$C, CDCl$_3$): 204.9 (CHO), 154.4 (CO3), 134.9 (Cipso), 130.6 (C-2), 128.64, 128.60 and 128.41 (Ar), 98.0 (C-1'), 78.2 (C-4'), 74.3 (8a-CH$_2$), 71.5 (C-5'), 70.0 (OCH$_2$Ph), 69.3 (C-2'), 69.0 (C-3').

EXAMPLE 23

[1R-(1α, 3aβ, 4β, 4aβ, 7β, 7aα, 8aβ)] 8a-[(6-Deoxy-3-O-butoxyacetyl-4-O-methyl-β-D-altropyranosyl-oxy)methyl]-4-formyl-4,4a,5,6,7,7a,8,8a-octahydro-7-methyl-3-(1-methylethyl)-1,4-methano-s-indacene-3a(1H)-carboxylic acid To a solution of Intermediate 35 (300 mg) in ethanol (50 ml) was added 10% palladium on charcoal (220 mg) under nitrogen. The mixture was shaken in Parr apparatus under 15 psi of hydrogen for 1 hour at room temperature. The catalyst was filtered off and the solvent evaporated to dryness. The residue was purified by flash column chromatography eluting with hexane:ethyl acetate (1:1) and dichloromethane:methanol (10:1) to yield the title compound (160 mg).

δ ($^1$H, CDCl$_3$): 9.71 (s, 1H, CHO), 6.07 (d, 1H, H-2, J=3.3 Hz), 5.55 (dd, 1H, H-3', J=4.2 and 3.3 Hz) 4.57 (d, 1H, H-1', J=0.6 Hz), 4.12 (AB system, 2H, OCH$_2$CO$_2$, J=12 Hz), 3.68 and 4.01 (2d, 2H, 8aCH$_2$, J=9.3 Hz), 3.80 (d, 1H, H-2', J=3.9 Hz), 3.68 (m, 1H, H-5'), 3.53 (t, 2H, CH$_2$O, J=6.6 Hz), 3.35 (s, 3H, 4'—OCH$_3$), 3.24 (dd, 1H, H-4', J=9 and 3 Hz), 2.70 (m, 1H, H-1); δ ($^{13}$C, CDCl$_3$): 204.6 (CHO), 176.4 (CO$_2$H), 169.6 ( 3'—CO$_2$), 148.2 (C-3), 130.7 (C-2), 98.1 (C-1'), 78.2 (C-4'), 74.2 (8aCH$_2$), 72.1 (C-3a), 71.7 (OCH$_2$CO$_2$), 69.5 (C-5'), 69.0 (C-3'), 68.0 (CH$_2$CH$_2$O), 67.9 (C-2'), 65.6 (C-8a); 58.8 (C-4), 57.7 (4'—OCH$_3$), 46.1 (C-1).

EXAMPLE 24

[1R-(1α, 3aβ, 4β, 4aβ, 7β, 7aα, 8aβ,)] 8a-[(6-Deoxy-4-O-methyl-3'-O-octanoyl-β-D-altropyranosyloxy)methyl]-4- formyl-4,4a,5,6,7,7a,8,8a-octahydro-7-methyl-3-(1-methylethyl)-1,4-methano-s-indacene-3a(1H)-carboxylic acid To a solution of Intermediate 36 (400 mg) in methanol (75 ml) was added 10% palladium on charcoal (275 mg) under nitrogen. The mixture was shaken in a Parr apparatus under 15 psi of hydrogen for 1.5 hours at room temperature. The catalyst was filtered and the solvent evaporated to dryness. The residue was purified by flash chromatography on silica gel eluting with dichloromethane:methanol (20:1). The appropriate fractions were combined and the solvent removed to give the title compound (200 mg).

δ ($^1$H, CDCl$_3$): 9.68 (s, 1H, CHO), 6.06 (dd, 1H, H-2, J=1.2 and 3.3 Hz), 5.48 (dd, 1H, H-3', J=3 and 4.5 Hz), 4.57 (d, 1H, H-1', J=1.5 Hz), 4.02 (d, 1H, H-8aCH$_2$, J=9.3 Hz), 3.72 (m, 3H, H-5', H-2' and H-8aCH$_2$), 3.28 (s, 3H, OCH$_3$), 3.26 (dd, 1H, H-4', J=3 and 9 Hz), 2.68 (t, 1H, H-1, J=3.3 Hz), 2.36 (m, 3H, H-14 and CH$_2$CO), 1.36-1.22 (m, 13H, 5CH$_2$ and 6'CH$_3$); δ ($^{13}$C, CDCl$_3$): 205.0 (CHO), 177.1 (COOH), 172.6 (COOR), 148.5 (C-3), 130.5 (C-2), 98.4 (C-1'), 78.2 (C-4'), 74.5 (C8aCH$_2$), 69.6 (C-2'), 69.2 (C-3'), 67.2 (C-5'), 65.6 (CH$_2$CO), 57.6 (OCH$_3$), 34.2, 28.8, 24.9, 22.5 (5CH$_2$), 18.1 (C-6'), 14.0 (CH$_3$).

EXAMPLE 25
[1R-(1α, 3aβ, 4β, 4aβ, 7β, 7aα, 8aβ)] 8a-[(6-Deoxy-4-O-methyl-3-O-(2-methylhexanoyl)-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid A solution of α-methylhexanoic acid (0.133 ml) and triethylamine (0.313 ml) was added to a solution of Intermediate 24 (0.371 g) and 2-chloro-1-methyl pyridinium iodide (0.267 g). The mixture was refluxed for 2 hours. After cooling, the solvent was evaporated and the residue was chromatographed on a silica gel column eluting with hexane:ethyl acetate (5:1) to afford the 3'-O-acyl derivative (0.43 g), which was dissolved in ethyl acetate (20 ml) and hydrogenated in a Parr apparatus using 10% palladium on charcoal (100 mg). After filtering off the palladium catalyst the solvent was removed and the residue was chromatographed on a silica gel flash column eluting with 5% dichloromethane:methanol to give the title compound (0.235 g) as a 1:1 mixture of diastereoisomers.

δ ($^1$H, CDCl$_3$): 9.70 (s, 1H, CHO), 6.05 (m, 1H, H-2), 5.47 (m, 1H, H-3'), 4.56 (brs, 1H, H-1'), 4.01 (brd, 1H, 8aCH$_2$), 3.73 (m, 3H, H-2', 5' and 8aCH$_2$), 3.32 (1, 3H, OMe), 3.26 (m, 1H, H4'), 2.70 (m, 1H, H-1), 2.05 (sext., 1H, CHCO$_2$), δ ($^{13}$C, CDCl$_3$): 204.7 (CHO), 176.9 and 175.6 (CO$_2$H and CO$_2$C), 148.4 (C-3), 130.5 (C-2), 98.4 (C-1'), 78.1 (C4), 74.5 (8aCH$_2$), 72.4 (C-3a), 69.7, 69.3 and 66.9 (C-2', C-3' and C-5'), 65.6 (C-8a), 58.8 (C4).

EXAMPLE 26
[1R-(1α, 3aβ, 4β, 4aβ, 7β, 7aα, 8aβ)] 8a-[(6-Deoxy-3-O-methoxyacetyl-4-O-methyl-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid To a solution of Intermediate 37 (200 mg) in ethanol (30 ml) was added 10% palladium on charcoal (170 mg) under nitrogen. The mixture was shaken in Parr apparatus under 15 psi of hydrogen for 1 hour at room temperature. The catalyst was filtered off and the solvent evaporated to dryness. The residue was purified by flash column chromatography eluting with hexane:ethyl acetate (3:1) and dichloromethane:methanol (15:1) to yield the title compound (120 mg).

δ ($^1$H, CDCl$_3$): 9.71 (s, 1H, CHO), 6.07 (dd, 1H, H-2, J=3.6 and 1.2 Hz), 5.56 (dd, 1H, H-3', J=4.2 and 3.3 Hz), 4.57 (d, 1H, H-1', J=1.5 Hz), 4.08 (AB system, 2H, OCH$_2$CO$_2$, J=12 Hz), 3.68 and 4.02 (2d, 2H, 8aCH$_2$, J=9 Hz), 3.80 (dd, 1H, H-2', J=1.2 and 4.5 Hz), 3.71 (m, 1H, H-5'), 3.35 (s, 3H, 4'—OCH$_3$), 3.45 (s, 3H, CH$_3$CH$_2$CO$_2$), 3.24 (dd, 1H, H4', J=9 and 3 Hz), 2.57 (t, 1H, H-1, J=3.9 Hz); δ ($^{13}$C, CDCl$_3$): 204.7 (CHO), 175.9 (CO$_2$H), 169.2 (3'—CO$_2$), 148.2 (C-3), 130.7 (C-2), 98.0 (C-1'), 78.2 (C4'), 74.1 (8aCH$_2$), 72.1 (C-3a), 69.5 (OCH$_2$CO,), 69.4 (C-5'), 68.9 (C-3'), 67.9 (C-2'), 65.6 (C-8a), 59.3 (CH$_2$OCH$_3$), 58.9 (C-4), 57.7 (4'—OCH$_3$), 46.0 (C-1).

EXAMPLE 27
[1R-(1α, 3aβ, 4β, 4aβ, 7β, 7aα, 8aβ)] 8a-[(6-Deoxy-4-O-methyl-3-O-((E)-2-methyl-2-hexenoyl)-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid Zinc dust (300 mg) followed by 1M aqueous potassium dihydrogen phosphate (1 ml) were added to a rapidly stirred solution of Intermediate 39 (131 mg) in tetrahydrofuran (5 ml) at room temperature. The resultant slurry was stirred for, 3 days at room temperature and the solids were removed by filtration and washed with a (5:1) mixture of tetrahydrofuran:water (20 ml). The filtrate and washings were combined, the solvent was removed in vacuo and the residue evaporated twice from toluene. The resulting colourless gum was purified by preparative tlc (Merck 5717) eluting with dichloromethane:methanol (10:1) and washing the product off the silica gel with ethyl acetate:methanol (8:1). Removal of the solvent gave the title compound (51 mg) as a white foam.

δ ($^1$H, CDCl$_3$): 9.72 (s, 1H, CHO), 6.8 (m, 1H, RO$_2$CC(CH$_3$)=CH—R'), 6.06 (m, 1H, H-2), 5.54 (m, 1H, H-3'), 4.60 (d, 1H, H-1', J=1.2 Hz), 4.09, 3.67 (2d, 2H, 8aCH$_2$, J$_{AB}$=9.6 Hz), 3.84 (m, 1H, H-2'), 3.77 (m, 1H, H-5'), 3.35 (s, 3H, —OCH$_3$), 3.3 (m, 1H, H4'), 2.68 (m, 1H, H-1), 2.34 (m, 1H, CHMe$_2$).

EXAMPLE 28
[1R-(1α, 3aβ, 4β, 4aβ, 7β, 7aα, 8aβ)] 8a-[(3-O-(4-Chlorobutyryl)-6-deoxy-4-O-methyl-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid To a solution of Intermediate 40 (250 mg) in methanol (10 ml) was added 10% palladium on charcoal (165 mg) under nitrogen. The mixture was shaken in a Parr apparatus under 18 psi of hydrogen for 1 hour at room temperature. The catalyst was filtered and the solvent evaporated to dryness. The residue was purified by flash chromatography on silica gel, eluting with dichloromethane:methanol (20:1). The appropriate fractions were combined and the solvent removed to give the title compound (138 mg) as a white foam.

δ ($^1$H, CDCl$_3$): 9.69 (s, 1H, CHO), 6.07 (dd, 1H, H-2, J=1.2 and 3.3 Hz), 5.49 (dd, 1H, H-3', J=3.6 and 4.5 Hz), 4.57 (d, 1H, H-1', J=1.5 Hz), 4.00 (d, 1H, H-8aCH$_2$, J=9.3 Hz), 3.77 (dd, 1H, H-2', J=1.2 and 4.5 Hz), 3.71 (m, 1H, H-5'), 3.69 (d, 1H, H-8aCH$_2$, J=9.3 Hz), 3.6 (t, 2H, CH$_2$O, J=6.3 Hz), 3.33 (s, 3H, OCH$_3$), 3.25 (dd, 1H, H4', J=3 and 9 Hz), 2.69 (m, 1H, H-1), 2.56 (t, 2H, CH$_2$Cl, J=7.2 Hz); δ ($^{13}$C, CDCl$_3$): 204.4 (CHO), 177.1 (CO$_2$H), 171.5 (COO), 148.3 (C-3), 130.0 (C-2), 98.2 (C-1'), 78.2 (C4'), 74.5 (C8aCH$_2$), 72.2 (C-3a), 69.5 (C-2'), 69.1 (C-3'), 67.6 (C-5'), 65.6 (CH$_2$CO), 58.6 (C-4), 57.7 (OCH$_3$), 46.0 (C-1), 43.6 (CH$_2$Cl), 31.9 (COCH$_2$CH2CH$_2$Cl), 18.1 (C-6')).

EXAMPLE 29

[1R-(1α, 3aβ, 4β, 4aβ, 7β, 7aα, 8aβ)] 8a-[(6-Deoxy-4-O-methyl-3-O-(2-methylpropanoyl)-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid To a solution of Intermediate 41 (0.270 g) in ethyl acetate (25 ml) was added 10% palladium on charcoal (25 mg) under nitrogen. The mixture was shaken in a Parr apparatus under 25 psi of hydrogen for 2 hours at room temperature. The catalyst was filtered off and the solvent evaporated to dryness. The residue was purified on a silica gel flash column eluting with hexane:ethyl acetate (3:1) to afford the title compound (0.119 g).

δ ($^1$H, CDCl$_3$): 9.71 (s, 1H, CHO), 6.06 (dd, 1H, H-2, J=0.9 and 3.3 Hz), 5.46 (dd, 1H, H-3', J=3.0 and 4.5 Hz), 4.56 (d, 1H, H-1', J=1.5 Hz), 4.00 (brd, 1H, 8aCH$_2$), 3.74 (m, 3H, H-2', 5' and 8aCH$_2$), 3.32 (s, 3H, OMe), 3.26 (dd, 1H, H-4', J=3.0 and 9.0 Hz), 2.70 (m, 1H, H-1), 2.61 (sept, 1H, (CH$_3$)$_2$CHCO$_2$); δ ($^{13}$C, CDCl$_3$): 204.6 (CHO), 177.0 and 175.9 (CO$_2$H and CO$_2$—C), 148.4 (C-3), 130.5 (C-2), 98.4 (C-1'), 78.2 (C-4'), 74.5 (8aCH$_2$), 72.4 (C-3a), 69.6, 69.2 and 67.1 (C-2', C-3' and C-5'), 58.7 (C-4).

EXAMPLE 30

[1R-(1α, 3aβ, 4β, 4aβ, 7β, 7aα, 8aβ)] 8a-[(6-Deoxy-4-O-methyl-3-O-propionyl-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid A solution of Intermediate 42 (274 mg) in ethyl acetate (20 ml) was hydrogenated in a Parr shaker at room temperature for 1.5 hours over 10% palladium on charcoal (150 mg). The catalyst was removed by filtration and the filtrate evaporated to a colourless gum. This was purified by preparative tlc (Merck 5717) eluting with dichloromethane:methanol (20:1). The product was washed off the silica gel with ethyl acetate:methanol (5:1) and the solvent removed in vacuo to give the title compound (123 mg) as a white foam.

δ ($^1$H, CDCl$_3$): 9.72 (s, 1H, CHO), 6.07 (dd, 1H, H-2, J=1.2 and 3.6 Hz), 5.48 (dd, 1H, H-3', J=3 and 4.5 Hz), 4.58 (d, 1H, H-1', J=1.2 Hz), 4.01 (d, 1H, A part of 8aCH$_2$, J$_{AB}$=9.3 Hz), 3.81-3.66 (m, 3H, H-2', H-5' and B part of 8aCH$_2$ (d)), 3.35 (s, 3H, OCH$_3$), 3.26 (dd, 1H, H-4', J=3 and 9 Hz), 2.7 (bt, 1H, H-1, J=3.6 Hz), 2.46-2.26 (m, 3H, RO$_2$CCH$_2$Me and CHMe$_2$), 1.16 (t, 3H, RO$_2$CCH$_2$CH$_3$, J=7.5 Hz); δ ($^{13}$C, CDCl$_3$): 204.6 (CHO), 176.4 (CO$_2$H), 173.3 (CO$_2$R), 148.2 (C-3), 130.7 (C-2), 98.3 (C-1'), 78.3, 69.6, 69.2, 67.4 (C-2', C-3', C-4', C-5'), 74.2 (8aCH$_2$), 72.2 (C-3a), 65.6 (C-8a), 58.8 (C4), 57.7 (OCH$_3$), 46.1 (C-1).

EXAMPLE 31

[1R-(1α, 3aβ, 4β, 4aβ, 7β, 7aα, 8aβ)] 8a-[(6-Deoxy-4-O-methyl-3-O-(trans-4-methyl-1-cyclohexanecarbonyl)-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid To a solution of Intermediate 43 (297 mg) in ethyl acetate (20 ml) was added 10% palladium on charcoal (150 mg) under nitrogen. The mixture was shaker in a Parr apparatus for 0.5 hours at room temperature. The catalyst was filtered off and the filtrate evaporated to dryness. The residue was purified by preparative tlc (silica gel, Merck 5717) eluting with dichloromethane:methanol (20:1) and extracted from the silica gel using ethyl acetate:methanol (5:1). The solvent was removed in vacuo to give the title compound (149 mg) as a white foam.

δ ($^1$H, CDCl$_3$): 9.71 (s, 1H, CHO), 6.06 (dd, 1H, H-2, J=1.2 and 3.3 Hz), 5.45 (dd, 1H, H-3', J=3.3 and 4.5 Hz), 4.56 (d, 1H, H-1', J=1.5 Hz), 4.01 (d, 1H, A part of 8aCH$_2$, J$_{AB}$=9.3 Hz), 3.8–3.64 (m, 3H, H-2', H-5' and B part of 8aCH$_2$), 3.32 (s, 3H, —OCH$_3$), 3.25 (dd, 1H, H4', J=3.3 and 8.7 Hz), 2.69 (bt, 1H, H-1, J=3.3 Hz), 2.4-2.2 (m, 2H, CHMe$_2$ and RO$_2$C—CH(cyclohexane)), 0.88 (d, 3H, H$_3$C-cyclohexane-CO$_2$R, J=6.3 Hz); δ ($^{13}$C, CDCl$_3$): 234.7 (CHO), 176.6 (CO$_2$H), 175 (RO$_2$C-cyclohexane), 148.3 (C-3), 130.6 (C-2), 98.4 (C-1'), 78.2, 69.7, 69.2, 67 (C-2', C-3', C-4', C-5'), 74.4 (8aCH$_2$), 72.3 (C-3a), 65.6 (C8a), 58.8 (C-4), 57.5 (OCH$_3$), 46.2 (C-1), 43.1 (RO$_2$C—CH(cyclohexane).

EXAMPLE 32

[1R-(1α, 3aβ, 4β, 4aβ, 7β, 7aα, 8aβ)] 8a-[(3-O-trans-Cinnamoyl-6-deoxy-4-O-methyl-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid Zinc dust (400 mg) followed by 1M aqueous potassium dihydrogen phosphate (0.4 ml) were added to a vigorously stirred solution of Intermediate 45 (170 mg) in tetrahydrofuran (4 ml) at room temperature. The resultant slurry was stirred for 2 days at room temperature and the solids were removed by filtration and washed with ethyl acetate. The filtrate and washings were combined, the solvent was removed under vacuum and the residue material partitioned between ethyl acetate (50 ml) and 1N aqueous hydrochloric acid (50 ml). The organic layer was washed with water and brine, then dried (Na$_2$SO4), filtered and evaporated. The residue was filtered through Dowex 50X8-200 ion-exchange resin using methanol as the eluent. The filtrate was concentrated in vacuo and the residue flash chromatographed on silica gel eluting with dichloromethane:methanol (97:3) to give the title compound (105 mg) as a white foam.

δ ($^1$H, CDCl$_3$): 9.71 (s, 1H, CHO), 7.72 (d, 1H, Ph—CH=C—CO$_2$R, J=15.9 Hz), 7.58-7.36 (m, 5H, Ph), 6.48 (d, 1H, Ph—C=CH—CO$_2$R), 6.08 (dd, 1H, H-2, J=1.5 and 3.6 Hz), 5.60 (dd, 1H, H-3', J=3 and 4.5 Hz), 4.66 (d, 1H, H-1', J=1.2 Hz), 4.08, 3.7 (2d, 2H, 8aCH$_2$, J$_{AB}$=9 Hz), 3.92-3.78 (m, 2H, H-2', H-5'), 3.39 (s, 3H, —OCH$_3$), 3.35 (dd, 1H, H-4', J=3 and 8.7 Hz), 2.7 (t, 1H, H-1), 2.4–2.26 (m, 1H, CHMe$_2$); δ ($^{13}$C, CDCl$_3$): 204.8 (CHO), 176 (—CO$_2$H), 165.8 (RO$_2$C—C=C), 148.2 (C-3), 145.8 (Ph—C=C), 130.7 (C-2), 117.3 (RO$_2$C—C=C), 98.3 (C-1'), 78.3, 69.7, 69.2, 67.8 (C-2', C-3', C-4', C-5'), 74.2 (8aCH$_2$), 72 (3a), 65.6 (8a), 58.9 (C-4), 57.7 (OCH$_3$), 46.1 (C-1).

EXAMPLE 33

[1R-(1α, 3aβ, 4β, 4aβ, 7β, 7aα, 8aβ)] 8a-[(6-Deoxy-3-O-methacryloyl-4-O-methyl-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid Zinc dust (300 mg) followed by 1M aqueous potassium dihydrogen phosphate (0.3 ml) were added to a rapidly stirred solution of Intermediate 47 (95 mg) in tetrahydrofuran (4 ml) at room temperature. The resultant slurry was stirred for 2 days at room temperature and the solids were removed by filtration and washed with ethyl acetate. The filtrate and washings were combined, the solvent was removed under vacuum and the residue was partitioned between ethyl acetate (50 ml) and 1N aqueous hydrochloric acid (50 ml). The organic layer was washed successively with water and brine, then dried over sodium sulphate, filtered and evaporated. The residue was filtered through Dowex 50X8-200 ion-exchange resin using methanol as the eluent. The filtrate was concentrated by evaporation and the residue was flash chromatographed on silica gel eluting with dichloromethane:methanol (96:4). Removal of the solvent gave the title compound (60 mg).

δ ($^1$H, CDCl$_3$): 9.72 (s, 1H, CHO), 6.14 (bs, 1H, Ha—C=C), 6.07 (m, 1H, H-2), 5.62 (m, 1H, Hb—C=C), 5.54 (m, 1H, H-3'), 4.60 (d, 1H, H-1', J=0.9 Hz), 4.03,3.69 (2d, 2H, 8aCH$_2$, J$_{AB}$=9.3 Hz), 3.84 (d, 1H, H-2', J=4.5 Hz), 3.76 (m, 1H, H-5'), 3.35 (s, 3H, —OCH$_3$), 3.31 (dd, 1H, H-4', J=3 and 9 Hz), 2.69 (m, 1H, H-1), 2.34 (m, 1H, CHMe$_2$), 1.97 (s, 3H, H$_3$C—C=C); δ ($^{13}$C, CDCl$_3$): 204.8 (CHO), 176 (—CO$_2$H), 166 (R—CO$_2$R'), 148.4 (C-3), 135.9 (—C=CH$_2$), 130.7 (C-2), 126.3 (—C=CH$_2$), 98.4 (C-1'), 78.3, 69.8, 69.2, 67.8 (C-2', C-3', C-4', C-5'), 74.4 (8aCH$_2$), 72 (C3a), 65.7 (C-8a), 58.9 (C4), 57.7 (OCH$_3$), 46.2 (C-1).

EXAMPLE 34

[1R-(1α, 3aβ, 4β, 4aβ, 7β, 7aα, 8aβ)]8a-[(6-Deoxy-4-O-methyl-3'-O-octyloxycarbonyl-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid To a solution of Intermediate 48 (320 mg) in methanol (40 ml) was added 10% palladium on charcoal (175 mg) under nitrogen. The mixture was shaken in a Parr apparatus under 15 psi of hydrogen for 1.5 hours at room temperature. The catalyst was filtered and the solvent evaporated to dryness. The residue was purified by flash chromatography on silica gel, eluting with dichloromethane:methanol (20:1). The appropriate fractions were combined and the solvent removed to give the title compound (168 mg) as a white foam.

δ ($^1$H, CDCl$_3$): 9.66 (s, 1H, CHO), 6.04 (dd, 1H, H-2, J=0.9 and 3.3 Hz), 5.28 (dd, 1H, H-3', J=3 and 3.9 Hz), 4.63 (d, 1H, H-1', J=0.9 Hz) 4.13 (t, 2H, CH$_2$OCO, J=6.6 Hz), 4.02 and 3.66 (2d, 2H, 8aCH$_2$, J=9.6 Hz), 3.86 (dd, 1H, H-2', J=1.2 and 4.2 Hz), 3.74 (m, 1H, H-5'), 3.37 (s, 3H, OCH$_3$), 3.27 (dd, 1H, H-4, J=3 and 9 Hz), 1.4-1.1 (m, 6CH$_2$ and 6'CH$_3$); δ ($^{13}$C, CDCl$_3$): 205.1 (CHO), 177.3 (COOH), 154.5 (OCOO), 148.5 (C-3), 130.5 (C-2), 98.2 (C-1'), 78.2 (C-4'), 74.5 (C8aCH$_2$), 72.6 (C-3a), 71.1 (C-2'), 69.3 (C-3'), 69.1 (C-5'), 68.6 (CH$_2$—OCOO), 57.9 (OCH$_3$), 31.6, 29.1, 29.0, 28.5, 25.5, 22.5 (6CH$_2$—), 17.9 (C-6'), 14.0 (CH$_3$).

EXAMPLE 35

[1R-(1α, 3aβ, 4β, 4aβ, 7β, 7aα, 8aβ) ]8a-[(6-Deoxy-4-O-methyl-3-O-octanoylaminocarbonyl-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid To a solution of Intermediate 49 (200 mg) in ethyl acetate (20 ml) was added 10% palladium on charcoal (100 mg) under nitrogen. The mixture was shaken in a Parr apparatus under 15 psi of hydrogen for 30 minutes at room temperature. The catalyst was filtered off and the solvent evaporated to dryness. The residue was chromatographed on a silica gel flash column eluting with methylene chloride and methylene chloride:methanol (15:1) to give the title compound (135 mg) as a white foam.

δ ($^1$H, CDCl$_3$): 9.72 (s, 1H, CHO), 6.07 (dd, 1H, H2, J=1.2 and 2.4 Hz), 5.32 (m, 1H, H-3'), 4.80 (t, 1H, CH$_2$—NH—CO$_2$), 4.57 (d, 1H, H-1', J=1.2Hz), 4.02 and 3.66 (2d, 2H, 8a-CH2, J=9.6 Hz), 3.74 (m, 1H, H-5'), 3.38 (s, 3H, 4'OCH$_3$), 3.28 (dd, 1H, H-4', J=2.8 and 8.7 Hz), 3.80 (m, 2H, CH$_2$NHCO$_2$), 2.70 (t, 1H, H-1); δ ($^{13}$C, CDCl$_3$): 204.7 (CHO), 175.9 (COOH), 155.5 (OCONH, 148.2 (C-3), 130.7 (C-2), 93.7 (C-1), 78.5 (C-4'), 72.2 (8a-CH$_2$), 69.6 (C-3'), 69.2 (C-5'), 65.6 (C-8a), 58.8 (C-2), 57.7 (C-7'), 18.2 (C-6').

EXAMPLE 36

[1R-(1α, 3aβ, 4β, 4aβ7β, 7aα, 8aβ)] 8a-[(6-Deoxy-3-O-benzylaminocarbonyl-4-O-methyl-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid To a solution of Intermediate 50 (100 mg) in ethyl acetate (15 ml) was added 10% palladium on charcoal (50 mg) under nitrogen. The mixture was shaken in a Parr apparatus under 15 psi of hydrogen for 10 minutes. The catalyst was filtered off and the solvent evaporated to dryness. The residue was chromatographed on a silica gel flash column using methylene chloride and methylene chloride:methanol (20:1) as eluents to give the title compound (56 mg) as a white foam.

δ ($^1$H, CDCl$_3$): 9.70 (s, 1H, CHO), 7.28 (m, 5H, 3'—Ph), 6.06 (d, 1H, H-2, J=3.3 Hz), 5.37 (m, 1H, H-3'), 5.17 (t, 1H, Ph—NH—CO$_2$), 4.55 (s, 1H, H-1'), 4.38 (m, 2H, Ph—CH$_2$—NH), 3.99 and 3.66 (2d, 2H, 8a-CH$_2$, J$_{AB}$=9.3 Hz), 3.87 (d, 1H, H-2', J=4.5 Hz), 3.39 (s, 3H, 4'—OCH$_3$), 3.28 (dd, 1H, H-4', J=2.7 and 8.4 Hz), 2.71 (t, 1H, H-1).

EXAMPLE 37

[1R-(1α, 3aβ, 4β, 4aβ, 7β, 7aα, 8aβ)] 8a-[(6-Deoxy-3-O-dimethylaminocarbonyl-4-O-methyl-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid To a solution of Intermediate 51 (0.165 g) in ethyl acetate (20 ml) was added 10% palladium on charcoal (20 mg) under nitrogen. The mixture was shaken in a Parr apparatus under 20 psi of hydrogen for 2 hours at room temperature. The catalyst was filtered off and the solvent evaporated to dryness. The residue was purified on a silica gel flash column eluting with 5% dichloromethane in methanol to give the title compound (0.060 g).

δ ($^1$H, CDCl$_3$): 9.71 (s, 1H, CHO), 6.07 (dd, 1H, H-2, 1.2 and 3.3 Hz), 5.36 (dd, 1H, H-3', J=3 and 4.5 Hz), 4.57 (d, 1H, H-1', J=1.2 Hz), 4.02 (m, 1H, 8aCH$_2$), 3.85 (m, 1H, H-2'), 3.75 (m, 1H, H-5'), 3.66 (m, 1H, 8aCH$_2$), 3.37 (s, 3H, MeO), 3.28 (dd, 1H, H-4', J=3.3+9.0 Hz), 2.94 (s, 6H, Me$_2$N), 2.70 (m, 1H, H-1); δ ($^{13}$C, CDCl$_3$): 204.9 (CHO), 176.2 (CO$_2$H), 155.5 (CON), 148.4 (C-3), 130.7 (C-2), 98.6 (C-1'), 78.5 (C-4'), 74.3 (8aCH$_2$), 72.4 (C-3a), 69.9, 69.4, 68.7 (C-2', C-3', and C-5'), 65.7 (C-8a), 58.9 (C-4).

EXAMPLE 38

[1R-(1α, 3aβ, 4β, 4aβ, 7β, 7aα, 8aβ)] 8a-[(2,6-Dideoxy-4-O-methyl-β-D-allopyranosyloxy)methyl]-4-formyl-4,4a,5,6,7,7a,8,8a-octahydro-7-methyl-3-(1-methylethyl)-1,4-methano-s-indacene-3a(1H)-carboxylic acid To a solution of Intermediate 33 (200 mg) in dry tetrahydrofuran (10 ml) at 0° C. and under nitrogen atmosphere, sodium hydride (25 mg) and imidazole (2 mg) were added. The solution was stirred for 10 minutes and carbon disulfide (0.12 ml) was added. After 20 minutes methyl iodide (0.25 ml) was added and the stirring continued for 30 minutes. 1N ammonium chloride was added and the reaction mixture extracted with ethyl acetate, the organic phase washed with brine, dried over magnesium sulphate and the solvent evaporated to dryness. The residue was flash chromatographed eluting with hexane:ethyl acetate (4:1) to obtain 214 mg of xanthate. 200 mg of this compound were dissolved in dry toluene (8 ml) under nitrogen atmosphere and heated at 110° C. A solution of tributyltin hydride (0.12 ml) in dry toluene (10 ml) was added dropwise over 2.5 hours with stirring. Methanol was added and the reaction mixture evaporated to dryness. The major compound of the crude was purified by flash chromatography on silica gel eluting with ethyl acetate:hexane (15:85) to obtain a foam. This foam was dissolved in ethyl acetate (10 ml). Palladium on charcoal was added (50 mg) and the suspension stirred under hydrogen atmosphere (30 psi) for 2 hours. The catalyst was filtered off and the solvent removed. The crude was flash chromatographed on silica gel eluting with dichloromethane:methanol (96:4) to yield the title compound (41 mg) as a foam.

δ ($^1$H, CDCl$_3$): 9.82 (s, 1H, CHO), 6.04 (dd, 1H, H-2, J=1.2 and 4.2Hz), 4.71 (dd, 1H, H-1', J=2.4 and 9.9 Hz), 4.32 (d, 1H, 8aCH$_2$, J=9.0 Hz), 4.24 (dd, 1H, H-3', J=3.0 and 6.6 Hz), 3.80-3.60 (m, 1H, H-5'), 3.40 (s, 3H, CH$_3$O), 3.55 (d, 1H, 8aCH$_2$, J=9.0 Hz), 2.85 (dd, 1H, H-4', J=3.0 and 9.3 Hz), 2.49 (t, 1H, H-1, J=3.6 Hz); δ ($^{13}$C, CDCl$_3$): 204.6 (CHO), 173.3 (CO$_2$H), 148.4 (C-3), 130.5 (C-2), 97.6 (C-1'), 82.1 (C-4'), 73.5 (8aCH$_2$), 68.5, 66.1, 63.8, 61.1, 57.3.

EXAMPLE 39

[1R-(1α, 3aβ, 4aβ, 7β, 7aα, 8aβ)] 8a-[(2,3,6-Trideoxy-4-O-methyl-β-D-allopyranosyloxy)methyl]-4-formyl-4,4a,5,6,7,7a,8,8a-octahydro-7-methyl-3-(1-methylethyl)-1,4-methano-s-indacene-3a(1H)-carboxylic acid To a solution of Intermediate 52(a) (180 mg) in ethyl acetate (40 ml) was added 10% palladium on charcoal (150 mg) under nitrogen. The mixture was shaken in a Parr apparatus under 15 psi of hydrogen for 1 hour at room temperature. The catalyst was filtered off and the solvent evaporated to dryness. The residue was purified by flash column chromatography eluting with hexane:ethyl acetate (3:1) and dichloromethane:methanol (10:1) to yield the title compound (82 mg).

δ ($^1$H, CDCl$_3$): 9.84 (s, 1H, CHO), 6.04 (dd, 1H, H-2, J=1.2 and 3.3 Hz), 4.33 (m, 2H, H-1' and H-8aCH$_2$), 3.34 (m, 4H, H-8aCH$_2$ and 4'—OCH$_3$), 3.28 (dq, 1H, H-5', J=6.3 and 9Hz), 2.80 (m, 1 H, H-4'), 2.50 (t, 1H, H-1, J=3.9 Hz); δ ($^{13}$C, CDCl$_3$): 204.6 (CHO), 174.1 (CO$_2$H), 148.4 (C-3), 130.4 (C-2), 101.2 (C-1'), 79.8 (C-4'), 74.8 (C-5'), 73.1 (8aCH$_2$), 65.1 (C-8a), 59.0 (C-4), 56.9 (4'—OCH$_3$), 47.1 (C-1), 41.0 and 41.5 (C-5 and C-6).

EXAMPLE 40

[1R-(1α, 3aβ, 4β, 4aβ, 7β, 7aα, 8aβ)] 8a-[(3,6-dideoxy-4-O-methyl-β-D-altropyranoxyloxy)methyl]-4-formyl-4,4a,5,6,7,7a,8,8a-octahydro-7-methyl-3-(1-methylethyl)-1,4-methano-s-indacene-3a(1H)-carboxylic acid 10% palladium on charcoal (100 mg) was added to a solution of Intermediate 53 (100 mg) in ethyl acetate (30 ml) under nitrogen. The mixture was shaken in a Parr apparatus under 15 psi of hydrogen for 1 hour at room temperature. The catalyst was filtered off and the solvent evaporated to dryness. The residue was purified by flash column chromatography eluting with hexane:ethyl acetate (3:1) and dichloromethane:methanol (15:1) to give the title compound (60 mg) as a white foam.

δ ($^1$H, CDCl$_3$): 9.74 (s, 1H, CHO), 6.06 (dd, 1H, H-2, J=1.2 and 3.3 Hz), 4.35 (s, 1H, H-1'), 3.64 and 4.09 (2brd, 2H, BaCH$_2$, J=9Hz), 3.90 (m, 1H, H-2'), 3.35 (m, 4H, H-5' and 4'—OCH$_3$), 3.21 (m, 1H, H-4'), 2.67 (m, 1H, H-1), 2.41 (m, 1H, H-3'a); δ ($^{13}$C, CDCl$_3$): 204 (CHO), 175.9 (CO$_2$H), 148.4 (C-3), 130.6 (C-2), 100.6 (C-1'), 76.6 (C-4'), 74.4 (C-2'), 74.0 (8aCH$_2$), 67.6 (C-5'), 65.6 (C-8a), 58.8 (C-4), 57.1 (4'—OCH$_3$).

EXAMPLE 41

[1R-(1α, 3aβ, 4β, 4aβ, 7β, 7aα, 8aβ)] 8a-(((2,3,6-Trideoxy-3-(tert-butoxycarbonyl)amino-b-D-allopyranosyl)oxy)methyl)-4-formyl-4,4a,5,6,7,7a,8,8a-octahydro-7-methyl-3-(1-methylethyl)-1,4-methano-s-indacene-3a(1H)-carboxylic acid To a solution of intermediate 22 (100 mg) in ethyl acetate (15 ml), di-tert-butyl dicarbonate (0.04 ml) and palladium (10%) on charcoal (30 mg) were added under nitrogen. The mixture was shaken in a Parr apparatus (PH$_2$=20 psi) for 2 hours at room temperature. The catalyst was filtered and the solvent evaporated to dryness. The residue was purified by flash column chromatography on silica gel eluting with dichloromethane:methanol 20:1 to give pure title compound (20 mg).

δ ($^1$H, CDCl$_3$): 13.20 (br s, 1H, COOH), 9.60 (s, 1H, CHO), 6.53 (br s, 1H, NH), 6.04 (d, 1H, H-2, J=2.7 Hz), 4.82 (br s 1H, OH), 4.48 (d, 1H, H-1', J=6.3 Hz), 3.82 (m, 1H, H-4'), 3.70 (d, 1H, H-8a, J=9.0 Hz), 3.61 (dq, 1H, H-5', J=8.1, 6.6 Hz), 3.48 (d, 1H, H-8a, J=9.0 Hz), 3.17 (m, 1H, H-3'), 2.58 (t, 1H, H-1, J=3.3 Hz), 2.21 (m, 1H, CH(CH$_3$)$_2$); δ ($^{13}$C, CDCl$_3$): 204.8 (CHO), 176.0 (COO—), 175.7 (COOH), 148.1 (C-3), 130.7 (C-2), 97.8 (C-1'), 73.7 (C-8a), 72.0 (C-5')+(C-4'), 46.47 (C-3').

EXAMPLE 42

[1R-(1α, 3aβ, 4β, 4aβ, 7β, 7aα, 8aβ)] 8a-(((2,3,6-Trideoxy-4-O-acetyl-3-acetylthio-b-D-allopyranosyl)oxy)methyl)-4-formyl-4,4a,5,6,7,7a,8,8a-octahydro-7-methyl-3-(1-methylethyl)-1,4-methano-s-indacene-3a(1H)-carboxylic acid A solution of Intermediate 54 (100 mg) in dichloromethane (10 ml) at 0° C. was treated with trifluoroacetic acid (0.1 ml). After 1 hour, the mixture was washed with sodium bicarbonate saturated solution (3 ml). The organic layer was treated with brine (3 ml) and dried over magnesium sulphate, filtered and concentrated. The residue was purified by flash column chromatography on silica gel, using dichlromethane:methanol (20:1), to give pure title compound (18 mg).

δ ($^1$H, CDCl$_3$)- 9.77 (s, 1H, CHO), 6.05 (dd, 1H, H-2, J=3.3 and 1.2 Hz), 4.72 (dd, 1H, H-1', J=8.4 and 4.2 Hz), 4.48 (dd, 1H, H-3', J=6.3 and 4.5 Hz), 4.30 (dd, 1H, H-4', J=8.7 and 4.5 Hz), 4.12 (d, 1H, H-8a, J=9.3 Hz), 3.70 (dq, 1H, H-5', J=8.1 and 6.0 Hz), 3.49 (d, 1H, H-8a, J=9.3 Hz), 2.60 (t, 1H, H-1, J=3.9 Hz), 2.35 (s, 3H, COCH$_3$), 2.33 (m, 1H, CH(CH$_3$)$_2$) 2.00 (s, 3H, COCH$_3$); δ ($^{13}$C, CDCl$_3$): 204.9 (CHO), 193.5 (SCOCH$_3$), 174.7 (COOH), 169.8 (OCOCH$_3$), 148.4 (C-3), 130.6 (C-2), 98.7 (C-1'), 73.7 (C-8a), 72.2 (C-4'), 70.5 (C-5'), 40.4 (C-3'), 30.7 (CH$_3$—COS), 20.8 (CH$_3$—COO).

EXAMPLE 43

[1R-(1α, 3aβ, 4β, 4aβ, 7β, 7aα, 8aβ)] 8a-(3-Acetamido-2,3,6-trideoxy-4-O-methyl-β-D-allopyranosyloxy)methyl-4-formyl-4,4a,5,6,7,7a,8,8a-octahydro-7-methyl-3-(1-methylethyl)-1,4-methano-s-indacene-3a(1H)-carboxylic acid To a solution of intermediate 23 (0.75 mmol) in ethyl acetate (20 ml), palladium (10%) on charcoal was added (75 mg) under nitrogen. The mixture was shaken in a Parr apparatus (PH$_2$=30 psi) for 4 hours at room temperature. The catalyst was filtered and the solution was treated with pyridine (3 ml) and acetic anhydride (0.2 ml) and stirred overnight at room temperature. After this time, was washed with hydrochloric acid (2N), sodium bicarbonate and brine. After removal of the solvent, the residue was purified by flash chromatography using dichloromethane:methanol 20:1 to give the title compound (207 mg).

δ ($^1$H, CDCl$_3$): 9.74 (s, 1H, CHO), 6.04 (dd, 1H, H-2, J=1.5 and 3.6 Hz), 5.85 (d, 1H, NH, J=5.7 Hz), 4.50 (dd, 1H, H-1', J=2.8 and 7.8 Hz), 4.24 (m, 1H, H-3'), 4.08 and 3.45 (d, d, 1H, 1H, 8a-CH$_2$, J=9.1 Hz), 3.87 (m, 1H, H-5'), 3.32 (s, 3H, OMe), 3.04 (dd, 1H, H-4', J=4.2 and 7.5 Hz), 2.60 (t, 1H, H-1, J=3.9 Hz), 2.04 (s, 3H, CH$_3$CO); δ ($^{13}$C, CDCl$_3$): 204.9 (CHO), 174.8 and 170.8 (CO$_2$ and CON), 148.3 (C-3), 130.7 (C-2), 98.2 (C-1'), 79.6 (C-4'), 73.5 (8a-CH$_2$), 69.3 (C-5'), 65.3 (C-8a), 59.0 (C-4).

EXAMPLE 44

[1R-(1α, 3aβ, 4β, 4aβ, 7β, 7aα, 8aβ)] 8a-[(3-O-benzoyl-2,6-dideoxy-4-O-methyl-β-allopyranosyloxy) methyl]-4-formyl-4,4a,5,6,7,7a,8,8a-octahydro-7-methyl-3-(1-methylethyl)-1,4-methano-s-indacene-3a(1H)-carboxylic acid To a solution of Intermediate 55 (180 mg) in ethyl acetate (25 ml), palladium (10%) on charcoal (50 mg) was added. The mixture was shaken in a Parr apparatus (PH$_2$=20 psi) for 1 hour at room temperature. The catalyst was filtered and the solvent evaporated to dryness. The residue was purified by flash chromatography with mixtures of hexane:ethyl acetate to give the title compound (60 mg) as a white foam.

δ ($^1$H, CDCl$_3$): 9.8 (s, 1H, CHO), 8.03-7.5 (m, 5H, arom), 6.04 (dd, 1H, H-2, J=1.4 and 2.5 Hz), 5.7 (c, 1H, H-3'), 4.7 (dd, 1H, H-1'), 4.36, 3.42 (dd, 2H, 8a-CH$_2$, J=10.8 Hz), 3.9 (m, 1H, H-5'), 3.39 (s, 3H, OCH$_3$), 3.00 (dd, 1H, H-4'), 2.50 (t, 1H, H-1); δ ($^{13}$C, CDCl$_3$): 204.7 (CHO), 173.64 (COOH), 165.53 (OCO—Ph), 148.5 (C-3), 130.5 (C-2), 133.2, 130.0, 129.6, 128.4 (Carom), 97.78 8C-1'), 80.87 (C-4'), 73.5 (8a-CH$_2$), 69.9 (C-5'), 66.17 (C-3'), 65.1 (C-8a), 57.5 (C4).

EXAMPLE 45

[1R-(1α, 3aβ, 4β, 4aβ, 7β, 7aα, 8aβ)] 8a-[(3-O-acetyl-2,6-dideoxy-4-O-methyl-β-allopyranosyloxy) methyl]-4-formyl-4,4a,5,6,7,7a,8,8a-octahydro-7-methyl-3-(1-methylethyl)-1,4-methano-s-indacene-3a(1H)-carboxylic acid To a solution of Intermediate 56 (221 mg) in ethyl acetate (20 ml), palladium (10%) on charcoal (50 mg) was added. The mixture was shaken in a Parr apparatus (PH$_2$=20 psi) for 1 hour at room temperature. The catalyst was filtered and the solvent evaporated to dryness. The residue was purified by flash chromatography using hexane:ethyl acetate 3:7 to give the title compound (100 mg) as a colourless oil.

δ (1H, CDCl$_3$): 9.82 (s, 1H, CHO), 6.05 (dd, 1H, H-2, J=1.44 and 2.5 Hz), 5.5 (c, 1H, H-3'), 4.63 (dd, 1H, H-1', J=2.5 and 9.36 Hz), 4.32, 3.39 (d, d, 2H, 8a-CH,2, J=11 Hz), 3.72 (m, 1H, H-5'), 3.39 (s, 3H, OCH$_3$), 2.88 (dd, 1H, H-4', J=3.6 Hz9, 2.5 (t, 1H, H-1), 2.1 (s, 2H, CH$_3$CO); δ (13C, CDCl$_3$): 204.5 (CHO), 174.7 (COOH), 170.143 (COCH$_3$), 148.3 (C-3), 130.56 (C-2), 97.67 (C1'), 80.78 (C4'), 73.8 (8aCH$_2$), 69.5 (C5'), 65.6 (C3'), 65.19 (C8a), 57.56 (C4).

EXAMPLE 46

Characteristics of IMI 362184

IMI 362184 is a mutant of Sordaria araneosa (ATCC 36386, NRRL 3193) isolated following N-methyl-N'-nitro-N-nitrosoguanidine mutagenesis of ascospores of this strain. The characteristics of IMI 362184 are essentially similar to those described in British Patent Specification No. 1,162,027 for NRRL 3196, except that IMI 362184 produces 4'-demethylsordarin as a major product under the same conditions used for sordarin production by NRRL 3196.

EXAMPLE 47

Characteristics of IMI 362947

IMI 362947 is a mutant of Sordaria araneosa (ATCC 36386, NRRL 3193) isolated following N-methyl-N'-nitro-N-nitrosoguanidine mutagenesis of ascospores of this strain. The characteristics of IMI 362947 are essentially similar to those described in British Patent Specification No. 1,162,027 for NRRL 3196, except that IMI 362947 does not produce ascospores readily on agar. The strain also differs from NRRL 3196 in that it produces sordaricin as a major product under the same conditions used for sordarin production by NRRL 3196.

EXAMPLE 48

Characteristics of NCIMB 40675

NCIMB 40675 is an aerobic, Gram-positive, non-motile irregular rod that produces lemon yellow, translucent, round, entire, convex colonies with a diameter of between 0.5–1 mm when grown on tryptic soy agar supplemented with 2% (w/v) yeast extract for 48 hours at 28° C. The organism grows well at temperatures up to 37° C., but not at 45° C. Metachromatic granules were not observed and the strain is catalase positive, oxidase negative and does not metabolise glucose fermentatively. The strain can utilise the following sources of carbon: α-D-glucose, D-fructose, p-hydroxyphenyl-acetic acid, D-mannitol, methylpyruvate, lactamide, D-trehalose and sucrose. The organism can only weakly utilise D-gluconic acid, pyruvic acid and salicin as sole carbon sources. Colony and microscopic morphology resembles that of coryneform bacteria. The genus Corynebacterium was excluded on the grounds that the peptidoglycan of NCIMB 40675 contains ornithine rather than the meso-isomer of 2,6-diaminopimelic acid or diaminobutyric acid. Also, the organism contains a complex mixture of branch chain fatty acids atypical of Corynebacterium species, namely, 12-methyltetradecanoic, 14-methylhexadecanoic and 14-methylpentadecanoic acids. The presence of α-branched-β-hydroxylated fatty acids was not determined. On the basis of these results NCIMB 40675 most closely resembles one of the following actinobacterial genera: Aureobacterium, Curtobacterium or Cellulomonas.

To clarify the taxonomic position of NCIMB 40675, a 1100 base pair partial sequence of the 16S rRNA gene was compared against 24 other species representing a range of actinobacteria and related genera. Results from this analysis indicate a close relationship between NCIMB 40675 and the genera Aureobacterium and Curtobacterium, but not Cellulomonas or Corynebacterium. More precise identification for the strain could be obtained by performing a phylogenetic analysis comparing variable regions of the 16S rRNA gene for a range of Aureobactedum and Curtobacterium species in addition to further chemotaxonomic and physiological tests.

Pharmacy Examples

| 1. Conventional oral tablet | |
|---|---|
| Drug substance | 100 mg |
| Microcrystalline cellulose | 160 mg |
| Crosscarmellose sodium | 20 mg |
| Magnesium stearate | 5 mg |

The drug substance is blended with microcrystalline cellulose, crosscarmellose sodium and magnesium stearate, then compressed into tablets.

| 2. Chewable oral tablet | |
|---|---|
| Drug substance | 100 mg |
| Xylitol | 865 mg |
| Peppermint flavour | 5 mg |
| Aspartame | 10 mg |
| Polyvinylpyrrolidone | 15 mg |
| Magnesium stearate | 5 mg |

The drug substance, xylitol, aspartame and polyvinylpyrrolidone are blended together and granulated with water, then dried. This granule is mixed with the peppermint flavour and magnesium stearate, then compressed into tablets.

| 3. Aqueous Oral Solution | |
|---|---|
| Drug substance | 100 mg |
| Hydroxypropylmethyl cellulose | 150 mg |
| Sodium propylhydroxybenzoate | 1 mg |
| Sodium methylhydroxybenzoate | 2 mg |
| Orange flavour | 10 mg |
| Sodium saccharin | 5 mg |
| Sucrose | 800 mg |
| Suitable buffers | qs |
| Purified water to | 5 mls |

Dissolve the drug substance and all the excipients in most of the purified water and mix. Make to volume and mix. Suitable buffers may be added to control the pH in the region of maximum stability.

| 4. Non-Aqueous Oral Suspension | |
|---|---|
| Drug substance | 100 mg |
| Aspartame | 50 mg |
| Grapefruit flavour | 25 mg |
| Mannitol | 800 mg |
| Colloidal silica | 10 mg |
| Fractionated coconut oil | 5 mls |

Disperse the drug substance and mannitol in the bulk of the fractionated coconut oil by high shear mixing. Add the remaining ingredients and mix. Make to volume with fractionated coconut oil and mix.

| 5. Ointment | |
|---|---|
| Drug substance | 200 mg |
| White Soft Paraffin | 9800 mg |

Melt the white soft paraffin, add the drug and mix. Continue to mix until the ointment starts to congeal.

| 6. | Injection | |
|---|---|---|
| | Drug substance | 40 mg |
| | Suitable buffers | qs |
| | Suitable antioxidants | qs |
| | Suitable chelating agents | qs |
| | Water for injections to | 2 mls |

Dissolve the drug substance in most of the water for injections. Suitable buffering agents may be added to control the pH to the region of optimum stability. Suitable antioxidants and chelating agents may be added to improve the stability of the injection. Make to mark with water for injections. Fill into ampoules or vials, then sterilise by autoclaving. Alternatively, sterilise by filtration and fill aseptically.

Antifungal Activity

Compounds of formula (I) have been tested for anti fungal activity in a standard in vitro screen and the minimum inhibiting concentration (MIC; $\mu$g/ml) determined for each compound against a variety of clinically relevant pathogens. The results obtained with representative compounds of the invention are given below.

The compounds of the invention are essentially non-toxic at therapeutically useful levels. For example the compounds of example 7, 10 and 89 when administered at a dose of 50 mg/kg sc were active in protecting male mice infected with *C. albicans* 4711E. At this dose no adverse effects were observed in the treated mice.

| | MICs $\mu$g/ml Example No. | | | | | | | | | | |
|---|---|---|---|---|---|---|---|---|---|---|---|
| ORGANISM | 3 | 5 | 7 | 8 | 9 | 10 | 11 | 15 | 24 | 39 | 42 |
| *C. albicans* 1208E | 4.000 | ≦0.001 | 0.015 | 0.250 | 8.0 | 1.0 | 1.0 | ≦0.001 | 0.60 | 0.060 | 0.060 |
| *C. albicans* 2005E | 0.250 | ≦0.001 | ≦0.001 | 0.030 | 2.0 | 0.12 | 0.250 | ≦0.001 | ≦0.001 | 0.004 | ≦0.001 |
| *C. albicans* 2402E | 2.00 | ≦0.001 | 0.008 | 0.250 | 8.0 | 1.00 | 1.00 | ≦0.001 | 0.030 | 0.060 | 0.060 |
| *C. albicans* 4711 | — | ≦0.001 | 0.004 | 0.120 | 4.0 | 0.500 | 1.00 | ≦0.001 | — | — | 0.015 |
| *C. tropicalis* 2808E | 1.00 | 0.004 | 0.003 | 2.00 | 16.0 | — | 2.00 | 0.004 | 0.060 | 0.250 | 1.00 |
| *C. psuedotropicalis* 2371E | 0.250 | ≦0.001 | 0.004 | 0.120 | 2.0 | — | 1.00 | ≦0.001 | 0.004 | 0.008 | ≦0.001 |
| *C. glabrata* 2375E | >125 | 1.000 | 8.00 | 16.00 | >125 | 62 | 31.00 | 1.00 | 500 | 8.00 | 31.00 |
| *C. glabrata* 2376E | >125 | 1.00 | 8.00 | 16.00 | >125 | 62 | 31.00 | 1.00 | 500 | 8.00 | 31.00 |
| *C. neoformans* 2867E | 31.00 | 31.00 | 125 | 31.00 | 125 | 4.0 | 0.050 | 31.00 | 0.25 | 62.00 | >125 |

We claim:

1. A compound of the formula (I)

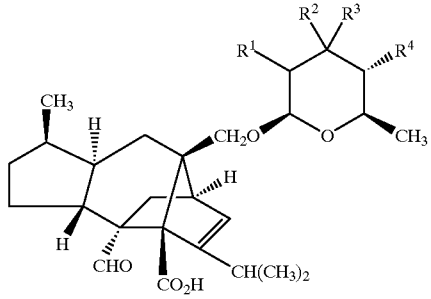

and pharmaceutically acceptable salts and solvates or metabolically labile derivatives thereof, wherein $R^1$ represents hydrogen, halogen, hydroxyl or $C_{1-4}$alkoxy;

$R^2$ represents hydrogen, halogen, hydroxyl, $C_{1-10}$alkoxy, $C_{1-10}$alkylthio, $C_{1-6}$alkoxy$C_{1-4}$alkoxy, aryl$C_{1-6}$alkyloxy, aryl$C_{3-6}$alkenyloxy, azido, $NR^5COR^5$ where each $R^5$ is independently hydrogen or $C_{1-6}$alkyl, $OR^6$ (where $R^6$ is a cyclic ether containing 4 to 8 atoms linked to the oxygen atom via a ring carbon atom adjacent to the ring oxygen atom or a group

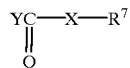

where Y is oxygen, sulphur or NH, X is either a bond, an oxygen atom or a moiety $NR^8$ in which $R^8$ is hydrogen or $C_{1-6}$alkyl, and $R^7$ is $C_{1-10}$alkyl optionally containing one or two double bonds, aryl, aryl$C_{1-4}$alkyl, aryl$C_{2-4}$alkenyl, halo$C_{1-6}$alkyl or $C_{1-6}$alkoxy$C_{1-4}$alkyl, and $R^3$ represents hydrogen, or $R^2$ and $R^3$ may together with the carbon atom to which they are attached represent C=O or C=NOR$^9$ where $R^9$ is $C_{1-6}$alkyl; and $R^4$ represents hydroxyl, $C_{1-6}$alkoxy or

(where $R^7$ is as defined above); with the proviso that when $R^1$ represents a hydroxyl group in the axial configuration and $R^4$ is methoxy then $R^2$ cannot represent a group in the axial configuration selected from hydroxyl and OCOCH=$^Z$CH—CH=$^E$CHCH$_3$.

2. A compound of the general formula (1a)

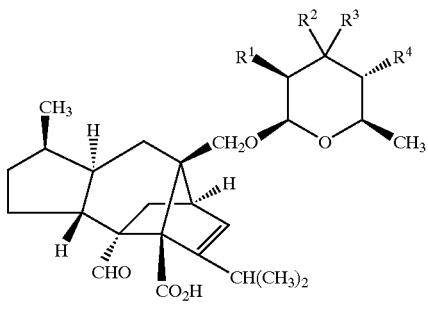

and pharmaceutically acceptable salts and solvates (e.g. hydrates) thereof, wherein $R^1$ to $R^4$ are as defined in formula (I) above.

3. A compound as claimed in claim 1 wherein $R^1$ represents hydrogen or hydroxyl.

4. A compound as claimed in claim 1 wherein $R^2$ is in the axial configuration and $R^3$ is hydrogen.

5. A compound as claimed in claim 1 wherein $R^2$ is $C_{1-6}$alkoxy, $C_{1-6}$alkylthio, azido or OCOR$^7$.

6. A compound as claimed in claim 1 wherein $R^4$ is $C_{1-4}$alkoxy.

7. A method of treatment of the human or non-human animal body to combat fungal diseases which method comprises administering to said body an effective amount of a compound as claimed in claim 1.

8. A pharmaceutical composition comprising a compound as claimed in claim 1 in admixture with one or more physiologically acceptable carriers or excipients.

9. A compound of formula (V)

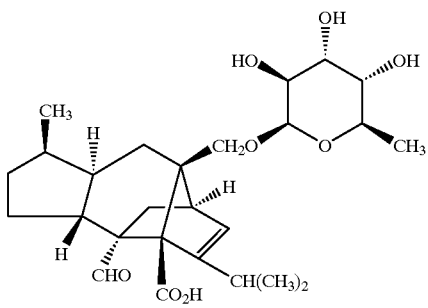

or a protected derivative thereof.

10. A process for the preparation of a compound of formula (V) which comprises
   (a) cultivating a microorganism capable of producing the compound of formula (V) and thereafter isolating the compound of formula (V) from the culture,
   (b) the biotransformation of sordarin.

* * * * *